United States Patent
Tohnishi et al.

(10) Patent No.: US 6,864,289 B1
(45) Date of Patent: Mar. 8, 2005

(54) AROMATIC DIAMIDE DERIVATIVES OR SALTS THEREOF, AGRICULTURAL/HORTICULTURAL CHEMICALS AND METHOD OF USING THE SAME

(75) Inventors: Masanori Tohnishi, Sakai (JP); Hayami Nakao, Kawachinagano (JP); Eiji Kohno, Bisai (JP); Tateki Nishida, Tondabayashi (JP); Takashi Furuya, Izumisano (JP); Toshiaki Shimizu, Kawachinagano (JP); Akira Seo, Hashimoto (JP); Kazuyuki Sakata, Kawachinagano (JP); Shinsuke Fujioka, Kawachinagano (JP); Hideo Kanno, Ibaraki (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 10/088,543

(22) PCT Filed: Sep. 22, 2000

(86) PCT No.: PCT/JP00/06514

§ 371 (c)(1),
(2), (4) Date: Mar. 19, 2002

(87) PCT Pub. No.: WO01/21576

PCT Pub. Date: Mar. 29, 2001

(30) Foreign Application Priority Data

Sep. 24, 1999 (JP) .......................................... 11-270582

(51) Int. Cl.⁷ ..................... C07C 233/83; C07C 237/22; C07D 213/82; A01N 37/22; A01N 37/50
(52) U.S. Cl. ..................... 514/617; 564/156; 546/304
(58) Field of Search ................................ 564/155, 156; 514/617; 546/304

(56) References Cited

FOREIGN PATENT DOCUMENTS

| EP | 0799825 | 10/1997 |
|---|---|---|
| EP | 0919542 | 6/1999 |
| HU | 188209 | 3/1986 |
| HU | P99004549 | 3/1991 |
| HU | P9200891 | 5/1993 |

OTHER PUBLICATIONS

Vatulina, G.G. et al. "Search for radioprotectors in a series of glutamic derivatives" Khim.–Farm. Zh., 1986, vol. 20, No. 9, p. 1078–1083.

*Primary Examiner*—Venkataraman Balasubramanian
(74) *Attorney, Agent, or Firm*—Paul E. White, Jr.; Manelli Denison & Selter PLLC

(57) ABSTRACT

Aromatic diamide derivative represented by the general formula (I) or a salt thereof and agricultural/herticultural composition containing the same as the active ingredient,

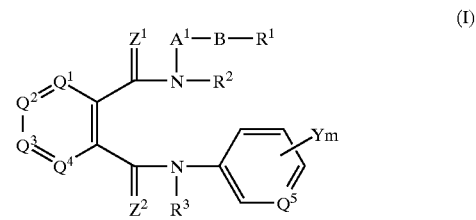

wherein $A^1$ represents alkylene, alkenylene or alkynylene; B represents, CO— or —C(=N—OR⁴)— (wherein $R^4$ represents H, etc.); $R^1$ to $R^3$ represent each H, etc.; $Q^1$ to $Q^5$ represent each N or carbon; Y represents halogeno, etc.; m is from 0 to 5; and $Z^1$ and $Z^2$ represent each O or S.

5 Claims, No Drawings

AROMATIC DIAMIDE DERIVATIVES OR SALTS THEREOF, AGRICULTURAL/HORTICULTURAL CHEMICALS AND METHOD OF USING THE SAME

This application is the national phase of international application PCT/JP00/06514 filed 22 Sep. 2000 which designated the U.S.

TECHNICAL FIELD

The present invention relates to an aromatic diamide derivative or a salt thereof; an agrohorticultural composition, particularly an agrohorticultural insecticide both containing the derivative or the salt as an effective ingredient; and a method for using the same.

BACKGROUND ART

A compound similar to the aromatic diamide derivative represented by the general formula (I) of the present invention is disclosed in EP 919542 A2.

DISCLOSURE OF THE INVENTION

The present inventors made an intensive study in order to develop a novel agrohorticultural composition, particularly an agrohorticultural insecticide and, as a result, found out that an aromatic diamide derivative represented by the general formula (I) or a salt thereof according to the present invention is a novel compound not described in any literature and is useful as an agrohorticultural composition, particularly as an agrohorticultural insecticide. The present invention has been completed based on the above finding.

The present invention relates to an aromatic diamide derivative represented by the following general formula (I) or a salt thereof; an agrohorticultural composition, particularly an agrohorticultural insecticide; and a method for using the insecticide:

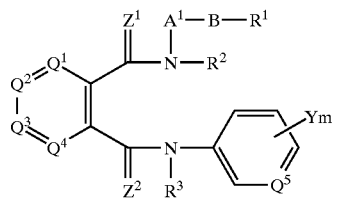
(I)

{wherein $A^1$ is a $(C_1-C_8)$alkylene group; a substituted $(C_1-C_8)$ alkylene group having one or more same or different substituents selected from halogen atoms, cyano group, nitro group, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, $(C_1-C_6)$alkylthio$(C_1-C_6)$alkyl groups, $(C_1-C_6)$alkoxycarbonyl groups and phenyl group; a $(C_3-C_8)$alkenylene group; a substituted $(C_3-C_8)$alkenylene group having one or more same or different substituents selected from halogen atoms, cyano group, nitro group, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo $(C_1-C_6)$alkylsulfonyl groups, $(C_1-C_6)$-alkylthio$(C_1-C_6)$alkyl groups, $(C_1-C_6)$alkoxycarbonyl groups and phenyl group; a $(C_3-C_8)$alkynylene group; or a substituted $(C_3-C_8)$ alkynylene group having one or more same or different substituents selected from halogen atoms, cyano group, nitro group, halo$(C_1-C_6)$alkyl groups, $(C_1-C_6)$alkoxy groups, halo$(C_1-C_6)$alkoxy groups, $(C_1-C_6)$alkylthio groups, halo $(C_1-C_6)$alkylthio groups. $(C_1-C_6)$alkylsulfinyl groups, halo $(C_1-C_6)$alkylsulfinyl groups, $(C_1-C_6)$alkylsulfonyl groups, halo$(C_1-C_6)$alkylsulfonyl groups, $(C_1-C_6)$alkylthio$(C_1-C_6)$ alkyl groups, $(C_1-C_6)$alkoxycarbonyl groups and phenyl group;

in the $(C_1-C_8)$alkylene group, the substituted $(C_1-C_8)$ alkylene group, the $(C_3-C_8)$alkenylene group, the substituted $(C_3-C_8)$ alkenylene group, the $(C_3-C_8)$-alkynylene group or the substituted $(C_3-C_8)$alkynylene group, any saturated carbon atom may be substituted with a $(C_2-C_5)$ alkylene group to form a $(C_3-C_6)$ cycloalkane ring; further in the $(C_1-C_8)$alkylene group, the substituted $(C_2-C_5)$ alkylene group, the $(C_3-C_8)$ alkenylene group or the substituted $(C_3-C_8)$ alkenylene group, any two carbon atoms may be combined with an alkylene group or an alkenylene group to form a $(C_3-C_6)$cycloalkane ring or a $(C_3-C_6)$cycloalkene ring;

B is —CO— or —C(=N—OR$^4$)— (wherein R$^4$ is a hydrogen atom; a $(C_1-C_6)$alkyl group; a halo$(C_1-C_6)$ alkyl group; a $(C_3-C_6)$alkenyl group; a halo$(C_3-C_6)$ alkenyl group; a $(C_3-C_6)$alkynyl group; a $(C_3-C_6)$ cycloalkyl group; a phenyl$(C_1-C_4)$alkyl group; or a substituted phenyl$(C_1-C_4)$alkyl group having, on the ring, one or more same or different substituents selected from halogen atoms, cyano group, nitro group, $(C_1-C_6)$ alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$ alkylsulfinyl groups, halo$(C_1-C_6)$-alkylsulfinyl groups, $(C_1-C_6)$alkylsulfonyl groups, halo$(C_1-C_6)$ alkylsulfonyl groups, mono$(C_1-C_6)$alkylamino groups, di$(C_1-C_6)$alkylamino groups wherein the two alkyl groups may be the same or different, and $(C_1-C_6)$ alkoxycarbonyl groups);

$R_1$ is a hydrogen atom; a $(C_1-C_6)$alkyl group; a halo $(C_1-C_6)$alkyl group; a $(C_2-C_6)$alkenyl group; a halo $(C_2-C_6)$alkenyl group; a $(C_3-C_6)$cycloalkyl group; a halo$(C_3-C_6)$cycloalkyl group; a $(C_1-C_6)$alkoxy group; a halo$(C_1-C_6)$alkoxy group; a $(C_1-C_6)$alkylthio group; a halo$(C_1-C_6)$alkylthio group; a mono$(C_1-C_6)$ alkylamino group; a di$(C_1-C_6)$alkylamino group wherein the two alkyl groups may be the same or different; a phenyl group; a substituted phenyl group having one or more same or different substituents selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$-alkylsulfinyl groups, $(C_1-C_6)$alkylsulfonyl groups, halo$(C_1-C_6)$ alkylsulfonyl groups, mono$(C_1-C_6)$alkylamino groups, di$(C_1-C_6)$alkylamino groups wherein the two alkyl groups may be the same or different, and $(C_1-C_6)$-alkoxycarbonyl groups; a phenylamino group; a substituted phenylamino group having, on the ring, one or more same or different substituents selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$ alkylsulfinyl groups, halo$(C_1-C_6)$alkylsulfinyl groups, $(C_1-C_6)$alkylsulfonyl groups, halo $(C_1-C_6)$ alkylsulfonyl groups, mono($C_1$–$C_6$)alkylamino groups, di($C_1$–$C_6$)alkylamino groups wherein the two alkyl groups may be the same or different, and ($C_1$–$C_6$) alkoxycarbonyl groups; a phenyloxy group; a substituted phenyloxy group having one or more same or different substituents selected from halogen atoms, cyano groups, nitro group, ($C_1$–$C_6$)alkyl groups, halo ($C_1$–$C_6$)alkyl groups, ($C_1$–$C_6$)alkoxy groups, halo ($C_1$–$C_6$)alkoxy groups, ($C_1$–$C_6$)alkylthio groups, halo ($C_1$–$C_6$)alkylthio groups, ($C_1$–$C_6$)alkylsulfinyl groups, halo($C_1$–$C_6$)-alkylsulfinyl groups, ($C_1$–$C_6$) alkylsulfonyl groups, halo($C_1$–$C_6$)alkylsulfonyl groups, mono($C_1$–$C_6$)alkylamino groups, di($C_1$–$C_6$) alkylamino groups wherein the two alkyl groups may be the same or different, and ($C_1$–$C_6$)-alkoxycarbonyl groups; a phenylthio group; a substituted phenylthio group having one or more same or different substituents selected from halogen atoms, cyano group, nitro group, ($C_1$–$C_6$)alkyl groups, halo ($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)-alkylsulfinyl groups, ($C_1$–$C_6$)alkylsulfonyl groups, halo($C_1$–$C_6$) alkylsulfonyl groups, mono($C_1$–$C_6$)alkylamino groups, di($C_1$–$C_6$)alkylamino groups wherein the two alkyl groups may be the same or different, and ($C_1$–$C_6$) alkoxycarbonyl groups; a heterocyclic group; or a substituted heterocyclic group having one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo ($C_1$–$C_6$)alkoxy groups, ($C_1$–$C_6$)alkylthio groups, halo ($C_1$–$C_6$)alkylthio groups, ($C_1$–$C_6$)alkylsulfinyl groups, halo($C_1$–$C_6$)-alkylsulfinyl groups, ($C_1$–$C_6$) alkylsulfonyl groups, halo($C_1$–$C_6$)alkylsulfonyl groups, mono($C_1$–$C_6$)alkylamino groups, di($C_1$–$C_6$) alkylamino groups wherein the two alkyl groups may be the same or different, and ($C_1$–$C_6$)— alkoxycarbonyl groups;

$R^1$ may bond with A' to form a 4- to 7-membered ring which may contain, as a ring-constituting atom(s), one or two same or different atoms selected from oxygen, sulfur and nitrogen atoms;

$R^2$ and $R^3$ may be the same or different and are each a hydrogen atom, a ($C_3$–$C_6$)cycloalkyl group or —$A^2$— $R^5$ [wherein $A^2$ is —C(=O)—, —C(=S)—, —C(=$NR^6$)— (wherein $R^6$ is a hydrogen atom; a ($C_1$–$C_6$)alkyl group; a ($C_1$–$C_6$)alkoxy group; a mono ($C_1$–$C_6$)alkylamino group; a di($C_1$–$C_6$)-alkylamino group wherein the two alkyl groups may be the same or different; a ($C_1$–$C_6$)alkoxycarbonyl group; a phenyl group; or a substituted phenyl group having one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$) alkylsulfinyl groups, halo($C_1$–$C_6$)alkylsulfinyl groups, ($C_1$–$C_6$)alkylsulfonyl groups, halo($C_1$–$C_6$) alkylsulfonyl groups, mono($C_1$–$C_6$)alkylamino groups, di($C_1$–$C_6$)alkylamino groups wherein the two alkyl groups may be the same or different, and ($C_1$–$C_6$) alkoxycarbonyl groups), a ($C_1$–$C_8$)alkylene group, a halo($C_1$–$C_8$)alkylene group, a ($C_3$–$C_6$)alkenylene group, a halo($C_3$–$C_6$)alkenylene group, a ($C_3$–$C_6$) alkynylene group or a halo($C_3$–$C_6$)alkynylene group;

(1) when $A^2$ is —C(=O)—, —C(=S)— or —C(=$NR^6$)— (wherein $R^6$ has the same definition as given above), $R^5$ is a hydrogen atom; a ($C_1$–$C_6$)alkyl group; a halo($C_1$–$C_6$)-alkyl group; a ($C_1$–$C_6$)alkoxy group; a ($C_3$–$C_6$)cycloalkyl group; a halo($C_3$–$C_6$) cycloalkyl group; a phenyl group; a substituted phenyl group having one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)-alkylsulfinyl groups, ($C_1$–$C_6$) alkylsulfonyl groups, halo($C_1$–$C_6$) alkylsulfonyl groups, mono($C_1$–$C_6$)alkylamino groups, di($C_1$–$C_6$)alkylamino groups wherein the two alkyl groups may be the same or different, and ($C_1$–$C_6$)-alkoxycarbonyl groups; a heterocyclic group; a substituted heterocyclic group having one or more same or different substituents selected from halogen atoms, cyano group, nitro group, ($C_1$–$C_6$)alkyl groups, halo ($C_1$–$C_6$)alkyl groups, ($C_1$–$C_6$)alkoxy groups, halo ($C_1$–$C_6$)alkoxy groups, ($C_1$–$C_6$)alkylthio groups, halo ($C_1$–$C_6$)alkylthio groups, ($C_1$–$C_6$)alkylsulfinyl groups, halo($C_1$–$C_6$)-alkylsulfinyl groups, ($C_1$–$C_6$) alkylsulfonyl groups, if halo($C_1$–$C_6$)alkylsulfonyl groups, mono($C_1$–$C_6$)alkylamino groups, di($C_1$–$C_6$) alkylamino groups wherein the two alkyl groups may be the same or different, and ($C_1$–$C_6$)-alkoxycarbonyl groups; or —$A^3$—$R^7$ (wherein $A^3$ is —O—, —S— or —N($R^8$)— (wherein $R^8$ is a hydrogen atom; a ($C_1$–$C_6$)- alkylcarbonyl group; a halo($C_1$–$C_6$)alkylcarbonyl group; a ($C_1$–$C_6$)alkoxycarbonyl group; a phenylcarbonyl group; a substituted phenylcarbonyl group having one or more same or different substituents selected from halogen atoms, cyano group, nitro group, ($C_1$–$C_6$) alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$) alkylsulfinyl groups, halo($C_1$–$C_6$)alkylsulfinyl groups, ($C_1$–$C_6$)alkylsulfonyl groups, halo($C_1$–$C_6$) alkylsulfonyl groups, mono($C_1$–$C_6$)-alkylamino groups, di($C_1$–$C_6$)alkylamino groups wherein the two alkyl groups may be the same or different, and ($C_1$–$C_6$) alkoxycarbonyl groups; a phenyl ($C_1$–$C_4$)- alkoxycarbonyl group; or a substituted phenyl($C_1$–$C_4$)- alkoxycarbonyl group having, on the ring, one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo ($C_1$–$C_6$)-alkoxy groups, ($C_1$–$C_6$)alkylthio groups, halo ($C_1$–$C_6$)alkylthio groups, ($C_1$–$C_6$)alkylsulfinyl groups, halo($C_1$–$C_6$)alkylsulfinyl groups, ($C_1$–$C_6$)alkylsulfonyl groups, halo($C_1$–$C_6$)alkylsulfonyl groups, mono ($C_1$–$C_6$)-alkylamino groups, di($C_1$–$C_6$)alkylamino groups wherein the two alkyl groups may be the same or different, and ($C_1$–$C_6$)alkoxycarbonyl groups); and $R^7$ is a ($C_1$–$C_6$)alkyl group; a halo($C_1$–$C_6$)alkyl group; a ($C_3$–$C_6$)alkenyl group; a halo($C_3$–$C_6$)alkenyl group; a ($C_3$–$C_6$)alkynyl group; a halo($C_3$–$C_6$)alkynyl group; a ($C_3$–$C_6$)cycloalkyl group; a halo($C_3$–$C_6$)cycloalkyl group; a ($C_1$–$C_6$)alkylcarbonyl group; a halo($C_1$–$C_6$) alkylcarbonyl group; a ($C_1$–$C_6$)-alkoxycarbonyl group; a phenyl group; a substituted phenyl group having one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$) alkylsulfinyl groups, halo($C_1$–$C_6$)alkylsulfinyl groups, ($C_1$–$C_6$)alkylsulfonyl groups, halo($C_1$–$C_6$)-alkylsulfonyl groups, mono($C_1$–$C_6$)alkylamino groups, di($C_1$–$C_6$)alkylamino groups wherein the two alkyl groups may be the same or different, and ($C_1$–$C_6$) alkoxycarbonyl groups; a phenyl($C_1$–$C_4$)alkyl group; a substituted phenyl($C_1$–$C_4$)alkyl group having, on the ring, one or more same or different substituents selected from halogen atoms, cyano group, nitro group, ($C_1$–$C_6$) alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$) alkylsulfinyl groups, halo($C_1$–$C_6$)alkylsulfinyl groups, ($C_1$–$C_6$)alkylsulfonyl groups, halo ($C_1$–$C_6$) alkylsulfonyl groups, mono ($C_1$–$C_6$)-alkylamino groups, di($C_1$–$C_6$)alkylamino groups wherein the two alkyl groups may be the same or different, and ($C_1$–$C_6$) alkoxycarbonyl groups; a heterocyclic group; or a substituted heterocyclic group having one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo ($C_1$–$C_6$)alkoxy groups, ($C_1$–$C_6$)alkylthio groups, halo ($C_1$–$C_6$)alkylthio groups, ($C_1$–$C_6$)alkylsulfinyl groups, halo($C_1$–$C_6$)-alkylsulfinyl groups, ($C_1$–$C_6$) alkylsulfonyl groups, halo($C_1$–$C_6$) alkylsulfonyl groups, mono($C_1$–$C_6$) alkylamino groups, di($C_1$–$C_6$) alkylamino groups wherein the two alkyl groups may be the same or different, and ($C_1$–$C_6$)-alkoxycarbonyl groups);

(2) when $A^2$ is a ($C_1$–$C_8$)alkylene group, a halo($C_1$–$C_8$) alkylene group, a ($C_3$–$C_6$)alkenylene group, a halo ($C_1$–$C_6$)alkenylene group, a ($C_3$–$C_6$)alkynylene group or a halo($C_3$–$C_6$)alkynylene group, $R^5$ is a hydrogen atom; a halogen atom; a cyano group; a nitro group; a ($C_3$–$C_6$)cycloalkyl group; a halo($C_3$–$C_6$)cycloalkyl group; a ($C_1$–$C_6$)alkoxycarbonyl group; a phenyl group; a substituted phenyl group having one or more same or different substituents selected from halogen atoms, cyano group, nitro group, ($C_1$–$C_6$)alkyl groups, halo($C_1$–$C_6$) alkyl groups, ($C_1$–$C_6$) alkoxy groups, halo ($C_1$–$C_6$) alkoxy groups, ($C_1$–$C_6$)alkylthio groups, halo ($C_1$–$C_6$)alkylthio groups, ($C_1$–$C_6$)alkylsulfinyl groups, halo($C_1$–$C_6$)-alkylsulfinyl groups, ($C_1$–$C_6$) alkylsulfonyl groups, halo($C_1$–$C_6$)alkylsulfonyl groups, mono ($C_1$–$C_6$) alkylamino groups, di($C_1$–$C_6$) alkylamino groups wherein the two alkyl groups may be the same or different, and ($C_1$–$C_6$)-alkoxycarbonyl groups; a heterocyclic group; a substituted heterocyclic group having one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)-alkylsulfinyl groups, ($C_1$–$C_6$)alkylsulfonyl groups, halo($C_1$–$C_6$) alkylsulfonyl groups, mono($C_1$–$C_6$)alkylamino groups, di($C_1$–$C_6$)alkylamino groups wherein the two alkyl groups may be the same or different, and ($C_1$–$C_6$)-alkoxycarbonyl groups; or —$A^4$—$R^9$ (wherein $A^4$ is —O—, —S—, —SO—, —SO$_2$—, —N($R^8$)— ($R^8$ has the same definition as given above), —C(=O)— or —C(=NOR$^4$)— ($R^4$ has the same definition as given above);

(i) when $A^4$ is —O—, —S—, —SO—, —SO$_2$— or —N($R^8$)—($R^8$ has the same definition as given above), $R^9$ is a hydrogen atom; a ($C_1$–$C_6$)alkyl group; a halo ($C_1$–$C_6$)alkyl group; a ($C_3$–$C_6$)alkenyl group; a halo ($C_3$–$C_6$)alkenyl group; a ($C_3$–$C_6$)alkynyl group; a halo ($C_3$–$C_6$)alkynyl group; a ($C_3$–$C_6$)cycloalkyl group; a halo($C_3$–$C_6$)cycloalkyl group; a ($C_1$–$C_6$)alkylcarbonyl group; a halo($C_1$–$C_6$)-alkylcarbonyl group; a ($C_1$–$C_6$) alkoxycarbonyl group; a phenyl group; a substituted phenyl group having one or more same or different substituents selected from halogen atoms, cyano group, nitro group, ($C_1$–$C_6$)alkyl groups, halo ($C_1$–$C_6$) alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$) alkylsulfinyl groups, ($C_1$–$C_6$)alkylsulfonyl groups, halo($C_1$–$C_6$)alkylsulfonyl groups, mono($C_1$–$C_6$)-alkylamino groups, di($C_1$–$C_6$)alkylamino groups wherein the two alkyl groups may be the same or different, and ($C_1$–$C_6$)alkoxycarbonyl groups; a phenyl ($C_1$–$C_4$)alkyl group; a substituted phenyl($C_1$–$C_4$)alkyl group having, on the ring, one or more same or different substituents selected from halogen atoms, cyano group, nitro group, ($C_1$–$C_6$)alkyl groups, halo($C_1$–$C_6$)alkyl groups, ($C_1$–$C_6$)-alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$) alkylsulfinyl groups, ($C_1$–$C_6$)-alkylsulfonyl groups, halo($C_1$–$C_6$)alkylsulfonyl groups, mono($C_1$–$C_6$) alkylamino groups, di($C_1$–$C_6$)alkylamino groups wherein the two alkyl groups may be the same or different, and ($C_1$–$C_6$)alkoxycarbonyl groups; a heterocyclic group; or a substituted heterocyclic group having one or more same or different substituents selected from halogen atoms, cyano group, nitro group, ($C_1$–$C_6$) alkyl groups, halo($C_1$–$C_6$)alkyl groups, ($C_1$–$C_6$)-alkoxy groups, halo($C_1$–$C_6$)alkoxy groups, ($C_1$–$C_6$) alkylthio groups, halo($C_1$–$C_6$)alkylthio groups, ($C_1$–$C_6$)alkylsulfinyl groups, halo($C_1$–$C_6$)alkylsulfinyl groups, ($C_1$–$C_6$)-alkylsulfonyl groups, halo($C_1$–$C_6$) alkylsulfonyl groups, mono($C_1$–$C_6$)alkylamino groups, di($C_1$–$C_6$)alkylamino groups wherein the two alkyl groups may be the same or different, and ($C_1$–$C_6$) alkoxycarbonyl groups;

(ii) when $A^4$ is —C(=O)— or —C(=N—OR$^4$)— ($R^4$ has the same definition as given above), $R^9$ is a hydrogen atom; a ($C_1$–$C_6$)alkyl group; a halo($C_1$–$C_6$) alkyl group; a ($C_2$–$C_6$)alkenyl group; a halo($C_2$–$C_6$) alkenyl group; a ($C_3$–$C_6$)cycloalkyl group; a halo ($C_3$–$C_6$)cycloalkyl group; a ($C_1$–$C_6$)alkoxy group; a halo($C_1$–$C_6$)alkoxy group; a ($C_1$–$C_6$)alkylthio group; a halo($C_1$–$C_6$)alkylthio group; a mono($C_1$–$C_6$) alkylamino group; a di($C_1$–$C_6$)alkylamino group wherein the two alkyl groups may be the same or different; a phenyl group; a substituted phenyl group having one or more same or different substituents selected from halogen atoms, cyano group, nitro group, ($C_1$–$C_6$)alkyl groups, halo($C_1$–$C_6$)alkyl groups, ($C_1$–$C_6$)-alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)alkylsulfinyl groups, ($C_1$–$C_6$)-alkylsulfonyl groups, halo($C_1$–$C_6$) alkylsulfonyl groups, mono($C_1$–$C_6$)alkylamino groups, di($C_1$–$C_6$)alkylamino groups wherein the two alkyl groups may be the same or different, and ($C_1$–$C_6$) alkoxycarbonyl groups; a phenylamino group; a substituted phenylamino group having, on the ring, one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)alkylsulfinyl groups, ($C_1$–$C_6$)alkylsulfonyl groups, halo($C_1$–$C_6$)-alkylsulfonyl groups, mono($C_1$–$C_6$)alkylamino groups, di($C_1$–$C_6$)alkylamino groups wherein the two alkyl groups may be the same or different, and ($C_1$–$C_6$) alkoxycarbonyl groups; a phenyloxy group; a substituted phenyloxy group having one or more same or different substituents selected from halogen atoms, cyano group, nitro group, ($C_1$–$C_6$)alkyl groups, halo ($C_1$–$C_6$)alkyl groups, ($C_1$–$C_6$)-alkoxy groups, halo ($C_1$–$C_6$)alkoxy groups, ($C_1$–$C_6$)alkylthio groups, halo ($C_1$–$C_6$)alkylthio groups, ($C_1$–$C_6$)alkylsulfinyl groups, halo($C_1$–$C_6$)alkylsulfinyl groups, ($C_1$–$C_6$)-alkylsulfonyl groups, halo($C_1$–$C_6$)alkylsulfonyl groups, mono($C_1$–$C_6$)alkylamino groups, di($C_1$–$C_6$) alkylamino groups wherein the two alkyl groups may be the same or different, and ($C_1$–$C_6$)alkoxycarbonyl groups; a phenylthio group; a substituted phenylthio group having, on the ring, one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$) alkylsulfinyl groups, ($C_1$–$C_6$)alkylsulfonyl groups, halo($C_1$–$C_6$)-alkylsulfonyl groups, mono($C_1$–$C_6$) alkylamino groups, di($C_1$–$C_6$)alkylamino groups wherein the two alkyl groups may be the same or different, and ($C_1$–$C_6$)alkoxycarbonyl groups; a heterocyclic group; or a substituted heterocyclic group having one or more same or different substituents selected from halogen atoms, cyano group, nitro group, ($C_1$–$C_6$) alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$) alkylsulfinyl groups, halo($C_1$–$C_6$)alkylsulfinyl groups, ($C_1$–$C_6$)alkylsulfonyl groups, halo($C_1$–$C_6$)-alkylsulfonyl groups, mono($C_1$–$C_6$)alkylamino groups, di($C_1$–$C_6$)alkylamino groups wherein the two alkyl groups may be the same or different, and ($C_1$–$C_6$) alkoxycarbonyl groups)];

$R^2$ may bond with $A^1$ or $R^1$ to form a 4- to 7-membered ring which may contain, as a ring-constituting atom(s), one or two same or different atoms selected from oxygen, sulfur and nitrogen atoms;

$Q_1$ to $Q_4$ may be the same or different and are each a nitrogen atom or a carbon atom which may be substituted with X, and X may be the same or different, and is a halogen atom; a cyano group; a nitro group; a ($C_3$–$C_6$)cycloalkyl group; a halo($C_3$–$C_6$)cycloalkyl group; a ($C_1$–$C_6$)alkoxycarbonyl group; a phenyl group; a substituted phenyl group having one or more same or different substituents selected from halogen atoms, cyano group, nitro group, ($C_1$–$C_6$)alkyl groups, halo ($C_1$–$C_6$)alkyl groups, ($C_1$–$C_6$)alkoxy groups, halo ($C_1$–$C_6$)alkoxy groups, ($C_1$–$C_6$)alkylthio groups, halo ($C_1$–$C_6$)alkylthio groups, ($C_1$–$C_6$)alkylsulfinyl groups, halo($C_1$–$C_6$)-alkylsulfinyl groups, ($C_1$–$C_6$) alkylsulfonyl groups, halo($C_1$–$C_6$)alkylsulfonyl groups, mono($C_1$–$C_6$)alkylamino groups, di($C_1$–$C_6$) alkylamino groups wherein the two alkyl groups may be the same or different, and ($C_1$–$C_6$)-alkoxycarbonyl groups; a heterocyclic group; a substituted heterocyclic group having one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)-alkylsulfinyl groups, ($C_1$–$C_6$)alkylsulfonyl groups, halo($C_1$–$C_6$) alkylsulfonyl groups, mono($C_1$–$C_6$)alkylamino groups, di($C_1$–$C_6$)alkylamino groups wherein the two alkyl groups may be the same or different, and ($C_1$–$C_6$)-alkoxycarbonyl groups; or —$A^5$—$R^{10}$ [wherein $A^5$ is —O—, —S—, —SO—, —$SO_2$—, —C(=O)—, —C(=$NOR^4$)— ($R^4$ has the same definition as given above), a ($C_1$–$C_6$)alkylene group, a halo($C_1$–$C_6$) alkylene group, a ($C_2$–$C_6$)alkenylene group, a halo ($C_2$–$C_6$)alkenylene group, a ($C_2$–$C_6$)alkynylene group or a halo($C_2$–$C_6$)alkynylene group;

(1) when $A^5$ is —O—, —S—, —SO— or —$SO_2$—, $R^{10}$ is a halo($C_3$–$C_6$)cycloalkyl group; a halo($C_3$–$C_6$) cycloalkenyl group; a phenyl group; a substituted phenyl group having one or more same or different substituents selected from halogen atoms, cyano group, nitro group, ($C_1$–$C_6$)alkyl groups, halo($C_1$–$C_6$)alkyl groups, ($C_1$–$C_6$)-alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$) alkylsulfinyl groups, ($C_1$–$C_6$)-alkylsulfonyl groups, halo($C_1$–$C_6$)alkylsulfonyl groups, mono($C_1$–$C_6$) alkylamino groups, di($C_1$–$C_6$)alkylamino groups wherein the two alkyl groups may be the same or different, and ($C_1$–$C_6$)alkoxycarbonyl groups; a heterocyclic group; a substituted heterocyclic group having one or more same or different substituents selected from halogen atoms, cyano group, nitro group, ($C_1$–$C_6$) alkyl groups, halo($C_1$–$C_6$)alkyl groups, ($C_1$–$C_6$)-alkoxy groups, halo($C_1$–$C_6$)alkoxy groups, ($C_1$–$C_6$) alkylthio groups, halo($C_1$–$C_6$)alkylthio groups, ($C_1$–$C_6$)alkylsulfinyl groups, halo($C_1$–$C_6$)alkylsulfinyl groups, ($C_1$–$C_6$)-alkylsulfonyl groups, halo($C_1$–$C_6$) alkylsulfonyl groups, mono($C_1$–$C_6$)alkylamino groups, di($C_1$–$C_6$)alkylamino groups wherein the two alkyl groups may be the same or different, and ($C_1$–$C_6$) alkoxycarbonyl groups; or —$A^6$—$R^{11}$(wherein $A^6$ is a ($C_1$–$C_6$)alkylene group, a halo($C_1$–$C_6$)-alkylene group, a ($C_3$–$C_6$)alkenylene group, a halo($C_3$–$C_6$)alkenylene group, a ($C_3$–$C_6$)alkynylene group or a halo($C_3$–$C_6$) alkynylene group, and $R^{11}$ is a hydrogen atom; a halogen atom; a ($C_3$–$C_6$)cycloalkyl group; a halo ($C_3$–$C_6$)cycloalkyl group; a ($C_1$–$C_6$)alkoxycarbonyl group; a phenyl group; a substituted phenyl group having one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)alkylsulfinyl groups, ($C_1$–$C_6$)alkylsulfonyl groups, halo($C_1$–$C_6$) alkylsulfonyl groups, mono($C_1$–$C_6$)-alkylamino groups, di($C_1$–$C_6$)alkylamino groups wherein the two alkyl groups may be the same or different, and ($C_1$–$C_6$) alkoxycarbonyl groups; or —$A^7$—$R^{12}$ (wherein $A^7$ is —O—, —S—, —SO— or —$SO_2$—, and $R^{12}$ is a ($C_1$–$C_6$)alkyl group; a halo($C_1$–$C_6$)alkyl group; a ($C_3$–$C_6$)alkenyl group; a halo($C_3$–$C_6$)alkenyl group; a ($C_3$–$C_6$)alkynyl group; a halo($C_3$–$C_6$)alkynyl group; a ($C_3$–$C_6$)cycloalkyl group; a halo($C_3$–$C_6$)cycloalkyl group; a phenyl group; a substituted phenyl group having one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)-alkylsulfinyl groups, ($C_1$–$C_6$)alkylsulfonyl groups, halo($C_1$–$C_6$) alkylsulfonyl groups, mono($C_1$–$C_6$)alkylamino groups, di($C_1$–$C_6$)alkylamino groups wherein the two alkyl groups may be the same or different, and ($C_1$–$C_6$)-alkoxycarbonyl groups; a heterocyclic group; or a substituted heterocyclic group having one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo ($C_1$–$C_6$)alkoxy groups, ($C_1$–$C_6$)alkylthio groups, halo ($C_1$–$C_6$)alkylthio groups, ($C_1$–$C_6$)alkylsulfinyl groups, halo($C_1$–$C_6$)-alkylsulfinyl groups, ($C_1$–$C_6$) alkylsulfonyl groups, halo($C_1$–$C_6$)alkylsulfonyl groups, mono($C_1$–$C_6$)alkylamino groups, di($C_1$–$C_6$) alkylamino groups wherein the two alkyl groups may be the same or different, and ($C_1$–$C_6$)-alkoxycarbonyl groups));

(2) when $A^5$ is —C(=O)— or —C(=NOR$^4$)—(R$^4$ has the same definition as given above), $R^{10}$ is a ($C_1$–$C_6$)-alkyl group; a halo($C_1$–$C_6$)alkyl group; a ($C_2$–$C_6$) alkenyl group; a halo($C_2$–$C_6$)alkenyl group; a ($C_3$–$C_6$) cycloalkyl group; a halo($C_3$–$C_6$)cycloalkyl group; a ($C_1$–$C_6$)alkoxy group; a ($C_1$–$C_6$)alkylthio group; a mono($C_1$–$C_6$)alkylamino group; a di($C_1$–$C_6$) alkylamino group wherein the two alkyl groups may be the same or different; a phenyl group; a substituted phenyl group having one or more same or different substituents selected from halogen atoms, cyano group, nitro group, ($C_1$–$C_6$)alkyl groups, halo($C_1$–$C_6$) alkyl groups, ($C_1$–$C_6$) alkoxy groups, halo ($C_1$–$C_6$) alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)-alkylsulfinyl groups, ($C_1$–$C_6$)alkylsulfonyl groups, halo($C_1$–$C_6$)alkylsulfonyl groups, mono($C_1$–$C_6$) alkylamino groups, di($C_1$–$C_6$)alkylamino groups wherein the two alkyl groups may be the same or different, and ($C_1$–$C_6$)-alkoxycarbonyl groups; a phenylamino group; a substituted phenylamino group having, on the ring, one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$) alkylsulfinyl groups, ($C_1$–$C_6$)alkylsulfonyl groups, halo($C_1$–$C_6$)alkylsulfonyl groups, mono($C_1$–$C_6$)-alkylamino groups, di($C_1$–$C_6$)alkylamino groups wherein the two alkyl groups may be the same or different, and ($C_1$–$C_6$)alkoxycarbonyl groups; a heterocyclic group; or a substituted heterocyclic group having one or more same or different substituents selected from halogen atoms, cyano group, nitro group, ($C_1$–$C_6$) alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$) alkylsulfinyl groups, halo($C_1$–$C_6$)-alkylsulfinyl groups, ($C_1$–$C_6$)alkylsulfonyl groups, halo($C_1$–$C_6$) alkylsulfonyl groups, mono($C_1$–$C_6$)alkylamino groups, di($C_1$–$C_6$)alkylamino groups wherein the two alkyl groups may be the same or different, and ($C_1$–$C_6$)-alkoxycarbonyl groups;

(3) when $A^5$ is a ($C_1$–$C_6$)alkylene group, a halo($C_1$–$C_6$) alkylene group, a ($C_2$–$C_6$)alkenylene group, a halo ($C_2$–$C_6$)alkenylene group, a ($C_2$–$C_6$)alkynylene group or a halo($C_2$–$C_6$)alkynylene group, $R^{10}$ is a hydrogen atom; a halogen atom; a ($C_3$–$C_6$)cycloalkyl group; a halo($C_3$–$C_6$)-cycloalkyl group; a ($C_1$–$C_6$) alkoxycarbonyl group; a phenyl group; a substituted phenyl group having one or more same or different substituents selected from halogen atoms, cyano group, nitro group, ($C_1$–$C_6$)alkyl groups, halo ($C_1$–$C_6$) alkyl groups, ($C_1$–$C_6$) alkoxy groups, halo($C_1$–$C_6$)alkoxy groups, ($C_1$–$C_6$)alkylthio groups, halo ($C_1$ –$C_6$) alkylthio groups, ($C_1$–$C_6$)alkylsulfinyl groups, halo ($C_1$–$C_6$)alkylsulfinyl groups, ($C_1$–$C_6$)alkylsulfonyl groups, halo($C_1$–$C_6$)alkylsulfonyl groups, mono ($C_1$–$C_6$)-alkylamino groups, di($C_1$–$C_6$)alkylamino groups wherein the two alkyl groups may be the same or different, and ($C_1$–$C_6$)alkoxycarbonyl groups; a heterocyclic group; a substituted heterocyclic group having one or more same or different substituents selected from halogen atoms, cyano group, nitro group, ($C_1$–$C_6$) alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$) alkylsulfinyl groups, halo($C_1$–$C_6$)-alkylsulfinyl groups, ($C_1$–$C_6$)alkylsulfonyl groups, halo($C_1$–$C_6$) alkylsulfonyl groups, mono($C_1$–$C_6$)alkylamino groups, di($C_1$–$C_6$)alkylamino groups wherein the two alkyl groups may be the same or different, and ($C_1$–$C_6$)-alkoxycarbonyl groups; or —A$^8$—R$^{13}$ (wherein A$^8$ is —O—, —S—, —SO— or —SO$_2$—, and R$^{13}$ is a ($C_3$–$C_6$)cycloalkyl group; a halo($C_3$–$C_6$)cycloalkyl group; a phenyl group; a substituted phenyl group having one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)-alkylsulfinyl groups, ($C_1$–$C_6$)alkylsulfonyl groups, halo($C_1$–$C_6$) alkylsulfonyl groups, mono($C_1$–$C_6$)alkylamino groups, di($C_1$–$C_6$)alkylamino groups wherein the two alkyl groups may be the same or different, and ($C_1$–$C_6$)-alkoxycarbonyl groups; a heterocyclic group; a substituted heterocyclic group having one or more same or different substituents selected from halogen atoms, cyano group, nitro group, ($C_1$–$C_6$)alkyl groups, halo ($C_1$–$C_6$)alkyl groups, ($C_1$–$C_6$)alkoxy groups, halo ($C_1$–$C_6$)alkoxy, groups, ($C_1$–$C_6$)alkylthio groups, halo ($C_1$–$C_6$)alkylthio groups, ($C_1$–$C_6$)alkylsulfinyl groups, halo($C_1$–$C_6$)-alkylsulfinyl groups, ($C_1$–$C_6$) alkylsulfonyl groups, halo($C_1$–$C_6$)alkylsulfonyl groups, mono($C_1$–$C_6$)alkylamino groups, di($C_1$–$C_6$) alkylamino groups wherein the two alkyl groups may be the same or different, and ($C_1$–$C_6$)-alkoxycarbonyl groups; or —A$^9$—R$^{14}$ (wherein A$^9$ is a ($C_1$–$C_6$) alkylene group, a halo($C_1$–$C_6$)alkylene group, a ($C_2$–$C_6$)alkenylene group, a halo($C_2$–$C_6$)alkenylene group, a ($C_2$–$C_6$) alkynylene group or a halo ($C_3$–$C_5$) alkynylene group, and R$^{14}$ is a hydrogen atom; a halogen atom; a ($C_3$–$C_6$)-cycloalkyl group; a halo ($C_3$–$C_6$)cycloalkyl group; a ($C_1$–$C_6$)alkoxy group; a halo ($C_1$–$C_6$) alkoxy group; a ($C_1$–$C_6$)alkylthio group; a halo($C_1$–$C_6$)alkylthio group; a ($C_1$–$C_6$)alkylsulfinyl group; a halo($C_1$–$C_6$)alkylsulfinyl group; a ($C_1$–$C_6$) alkylsulfonyl group; a halo($C_1$–$C_6$)alkylsulfonyl group; a phenyl group; a substituted phenyl group having one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)alkylsulfinyl groups, ($C_1$–$C_6$)alkylsulfonyl groups, halo($C_1$–$C_6$)alkylsulfonyl groups, mono($C_1$–$C_6$)alkylamino groups, di($C_1$–$C_6$)alkylamino groups wherein the two alkyl groups may be the same or different, and ($C_1$–$C_6$) alkoxycarbonyl groups; a phenyloxy group; a substituted phenyloxy group having one or more same or different substituents selected from halogen atoms, cyano group, nitro group, ($C_1$–$C_6$)alkyl groups, halo ($C_1$–$C_6$)alkyl groups, ($C_1$–$C_6$)alkoxy groups, halo ($C_1$–$C_6$)alkoxy groups, ($C_1$–$C_6$)alkylthio groups, halo ($C_1$–$C_6$)alkylthio groups, ($C_1$–$C_6$)alkylsulfinyl groups, halo($C_1$–$C_6$)alkylsulfinyl groups, ($C_1$–$C_6$)alkylsulfonyl groups, halo($C_1$–$C_6$)alkylsulfonyl groups, mono ($C_1$–$C_6$)alkylamino groups, di($C_1$–$C_6$)alkylamino groups wherein the two alkyl groups may be the same or different, and ($C_1$–$C_6$)alkoxycarbonyl groups; a phenylthio group; a substituted phenylthio group having one or more same or different substituents selected from halogen atoms, cyano group, nitro group, ($C_1$–$C_6$) alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$) alkylsulfinyl groups, halo($C_1$–$C_6$)-alkylsulfinyl groups, ($C_1$–$C_6$)alkylsulfonyl groups, halo($C_1$–$C_6$) alkylsulfonyl groups, mono($C_1$–$C_6$)alkylamino groups, di($C_1$–$C_6$)alkylamino groups wherein the two alkyl groups may be the same or different, and ($C_1$–$C_6$)-alkoxycarbonyl groups; a heterocyclic group; or a substituted heterocyclic group having one or more same or different substituents selected from halogen atoms, cyano group, nitro group, ($C_1$–$C_6$) alkyl groups, halo ($C_1$–$C_6$) alkyl groups, ($C_1$–$C_6$) alkoxy groups, halo ($C_1$–$C_6$) alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)-alkylsulfinyl groups, ($C_1$–$C_6$) alkylsulfonyl groups, halo($C_1$–$C_6$)alkylsulfonyl groups, mono($C_1$–$C_6$)alkylamino groups, di($C_1$–$C_6$) alkylamino groups wherein the two alkyl groups may be the same or different, and ($C_1$–$C_6$)-alkoxycarbonyl groups))];

the two Xs bonding to the adjacent two carbon atoms constituting the aromatic ring containing $Q^1$ to $Q^4$ may bond to each other to form a condensed ring; the condensed ring may have one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$) alkylthio groups, halo ($C_1$–$C_6$) alkylthio groups, ($C_1$–$C_6$)alkylsulfinyl groups, halo($C_1$–$C_6$) alkylsulfinyl groups, ($C_1$–$C_6$)alkylsulfonyl groups, halo($C_1$–$C_6$)-alkylsulfonyl groups, mono($C_1$–$C_6$) alkylamino groups, di($C_1$–$C_6$)alkylamino groups wherein the two alkyl groups may be the same or different, and ($C_1$–$C_6$)alkoxycarbonyl groups;

Qs is a nitrogen atom or a carbon atom;

Y may be the same or different, and is a halogen atom; a cyano group; a nitro group; a halo($C_3$–$C_6$)cycloalkyl group; a phenyl group; a substituted phenyl group having one or more same or different substituents selected from halogen atoms, cyano group, nitro group, ($C_1$–$C_6$) alkyl groups, halo ($C_1$–$C_6$) alkyl groups, ($C_1$–$C_6$)alkoxy groups, halo($C_1$–$C_6$)alkoxy groups, ($C_1$–$C_6$) alkylthio groups, halo ($C_1$–$C_6$) alkylthio groups, ($C_1$–$C_6$)alkylsulfinyl groups, halo($C_1$–$C_6$) alkylsulfinyl groups, ($C_1$–$C_6$)alkylsulfonyl groups, halo($C_1$–$C_6$)alkylsulfonyl groups, mono($C_1$–$C_6$) alkylamino groups, di($C_1$–$C_6$)alkylamino groups wherein the two alkyl groups may be the same or different, and ($C_1$–$C_6$)alkoxycarbonyl groups; a heterocyclic group; a substituted heterocyclic group having one or more same or different substituents selected from halogen atoms, cyano group, nitro group, ($C_1$–$C_6$) alkyl groups, halo($C_1$–$C_6$)alkyl groups, ($C_1$–$C_6$)alkoxy groups, halo($C_1$–$C_6$)alkoxy groups, ($C_1$–$C_6$) alkylthio groups, halo ($C_1$–$C_6$) alkylthio groups, ($C_1$–$C_6$) alkylsulfinyl groups, halo($C_1$–$C_6$)alkylsulfinyl groups, ($C_1$–$C_6$)alkylsulfonyl groups, halo($C_1$–$C_6$)- alkylsulfonyl groups, mono($C_1$–$C_6$)alkylamino groups, di($C_1$–$C_6$)alkylamino groups wherein the two alkyl groups may be the same or different, and ($C_1$–$C_6$) alkoxycarbonyl groups; or —$A^5$—$R^{10}$ ($A^5$ and $R^{10}$ each have the same definition as given above);

the two Ys bonding to the adjacent two carbon atoms constituting the aromatic ring containing $Q^5$ may bond to each other to form a condensed ring; the condensed ring may have one or more same or different substituents selected from halogen atoms, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$) alkylsulfinyl groups, halo ($C$—$C_6$)alkylsulfinyl groups, ($C_1$–$C_6$)alkylsulfonyl groups, halo($C_1$–$C_6$) alkylsulfonyl groups, phenyl group, substituted phenyl groups having one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$) alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)-alkylsulfinyl groups, ($C_1$–$C_6$)alkylsulfonyl groups, halo($C_1$–$C_6$) alkylsulfonyl groups, mono($C_1$–$C_6$)alkylamino groups, di($C_1$–$C_6$)alkylamino groups wherein the two alkyl groups may be the same or different, and ($C_1$–$C_6$)- alkoxycarbonyl groups, heterocyclic groups, and substituted heterocyclic groups having one or more same or different substituents selected from halogen atoms, cyano group, nitro group, ($C_1$–$C_6$)alkyl groups, halo ($C_1$–$C_6$)alkyl groups, ($C_1$–$C_6$)alkoxy groups, halo ($C_1$–$C_6$)alkoxy groups, ($C_1$–$C_6$)alkylthio groups, halo ($C_1$–$C_6$)alkylthio groups, ($C_1$–$C_6$)alkylsulfinyl groups, halo($C_1$–$C_6$)-alkylsulfinyl groups, ($C_1$–$C_6$) alkylsulfonyl groups, halo($C_1$–$C_6$)alkylsulfonyl groups, mono($C_1$–$C_6$)alkylamino groups, di($C_1$–$C_6$) alkylamino groups wherein the two alkyl groups may be the same or different, and ($C_1$–$C_6$)-alkoxycarbonyl groups;

m is an integer of 0 to 5;

$Z^1$ and $Z^2$ may be the same or different and are each an oxygen atom or a sulfur atom}.

MODE FOR CARRYING OUT THE INVENTION

In the definition of the aromatic diamide derivative represented by the general formula (I) or the salt thereof according to the present invention, "halogen atom" refers to chlorine atom, bromine atom, iodine atom or fluorine atom; "($C_1$–$C_6$)alkyl group" refers to a straight chain or branched chain alkyl group having 1 to 6 carbon atoms, such as methyl, ethyl, n-propyl, isopropyl, n-butyl, isobutyl, sec-butyl, tert-butyl, n-pentyl, n-hexyl or the like; "halo($C_1$–$C_6$) alkyl group" refers to a straight chain or branched chain alkyl group having 1 to 6 carbon atoms, substituted with one or more same or different halogen atoms; "$(C_1-C_8)$alkylene group" refers to a straight chain or branched chain alkylene group having 1 to 8 carbon atoms, such as methylene, ethylene, propylene, trimethylene, dimethylmethylene, tetramethylene, isobutylene, dimethylethylene, octamethylene or the like.

"$(C_3-C_6)$cycloalkyl group" refers to an alicyclic alkyl group having 3 to 6 carbon atoms, such as cyclopropyl, cyclobutyl, cyclopentyl, cyclohexyl or the like.

"The 4- to 7-membered ring which may contain one or two same or different atoms selected from oxygen, sulfur and nitrogen atoms, which is formed by bonding of $R^1$ to $A^1$ or by bonding of $R^2$ to $A^{1}$" can be exemplified by cyclobutane ring, cyclopentane ring, cyclohexane ring, azetidine ring, pyrrolidine ring, pyrroline ring, piperidine ring, imidazolidine ring, imidazoline ring, oxazolidine ring, thiazolidine ring, isoxazolidine ring, isothiazolidine ring, tetra-hydropyridine ring, piperazine ring, morpholine ring, thiomorpholine ring, dioxazine ring and dithiazine ring. "The 4- to 7-membered ring which may contain one or two same or different atoms selected form oxygen, sulfur and nitrogen atoms, which is formed by bonding of $R^2$ to $R^{1}$" can be exemplified by azetidine ring, pyrrolidine ring, pyrroline ring, piperidine ring, imidazolidine ring, imidazoline ring, oxazolidine ring, thiazolidine ring, isoxazolidine ring, isothiazolidine ring, tetrahydropyridine ring, piperazine ring, morpholine ring, thiomorpholine ring, dioxazine ring and dithiazine ring.

"Heterocyclic ring" can be exemplified by pyridyl group, pyridine-N-oxide group, pyrimidyl group, furyl group, tetrahydrofuryl group, thienyl group, tetrahydrothienyl group, tetrahydropyranyl group, tetrahydrothiopyranyl group, oxazolyl group, isoxazolyl group, oxadiazolyl group, thiazolyl group, isothiazolyl group, thiadiazolyl group, imidazolyl group, triazolyl group and pyrazolyl group. "Condensed ring" can be exemplified by naphthalene, tetrahydronaphthalene, indene, indane, quinoline, quinazoline, indole, indoline, coumarone, isocoumarone, benzodioxane, benzodioxole, benzofuran, dihydrobenzofuran, benzothiophene, dihydrobenzothiophene, benzoxazole, benzothiazole, benzimidazole and indazole.

"Salt" can be exemplified by inorganic acid salts such as hydrochloride, sulfate, nitrate, phosphate and the like; organic acid salts such as acetate, fumarate, maleate, oxalate, methanesultonate, benzenesulfonate, paratoluenesulfonate and the like; and salts with metal ions such as sodium ion, potassium ion, calcium ion and the like.

The aromatic diamide derivative represented by the general formula (I) or the salt thereof according to the present invention may contain, in the structural formula, one or more asymmetric carbon atoms or asymmetric centers, and may contain two or more kinds of optical isomers or diastereomers; and the present aromatic diamide derivative or salt thereof includes even these individual optical isomers and mixtures of any proportions of the optical isomers. Also, the aromatic diamide derivative represented by the general formula (I) or the salt thereof according to the present invention may contain, in the structural formula, two kinds of geometrical isomers owing to the carbon-to-carbon double bond or carbon-to-nitrogen double bond; and the present aromatic diamide derivative or salt thereof includes even these individual geometrical isomers and mixtures of any proportions of the geometrical isomers.

In a preferred embodiment of the aromatic diamide derivative represented by the general formula (I) or the salt thereof according to the present invention, $A^1$ is a $(C_1-C_4)$ alkylene group, a $(C_3-C_5)$-alkenylene group or a $(C_1-C_4)$ alkynylene group; B is —CO— or —C(=N—OR$^4$)— (R$^4$ is a hydrogen atom or a $(C_1-C_3)$alkyl group); $R^1$ is a $(C_1-C_3)$ alkyl group, a $(C_1-C_3)$alkoxy group, a mono$(C_1-C_3)$ alkylamino group or a di$(C_1-C_3)$alkylamino group wherein the two alkyl groups may be the same or different; $R^2$ and $R^3$ are each a hydrogen atom; $Q^1$ and $Q^2$ are each a carbon atom; X may be the same or different, and is a halogen atom, a nitro group, a halo$(C_1-C_6)$alkyl group or a halo$(C_1-C_6)$ alkoxy group; $Q^3$ and $Q^4$ are each a carbon atom; $Q^5$ is a nitrogen atom or a carbon atom; Y may be the same or different, and is a halogen atom, a $(C_1-C_6)$alkyl group, a halo$(C_1-C_6)$ alkyl group, a $(C_1-C_6)$ alkoxy group, a halo $(C_1-C_6)$-alkoxy group or a halo $(C_1-C_6)$ alkoxyhalo $(C_1-C_6)$ alkoxy group; m is an integer of 1 to 3; and $Z^1$ and $Z^2$ are each an oxygen atom.

The aromatic diamide derivative represented by the general formula (I) or the salt thereof according to the present invention can be produced, for example, by the processes shown in the following schemes. The present aromatic diamide derivative or salt thereof can also be produced, for example, by the process disclosed in Japanese Patent Application No. 10-350768. However, the processes for producing the present aromatic diamide derivative or salt thereof are not restricted to these processes.

Production process 1

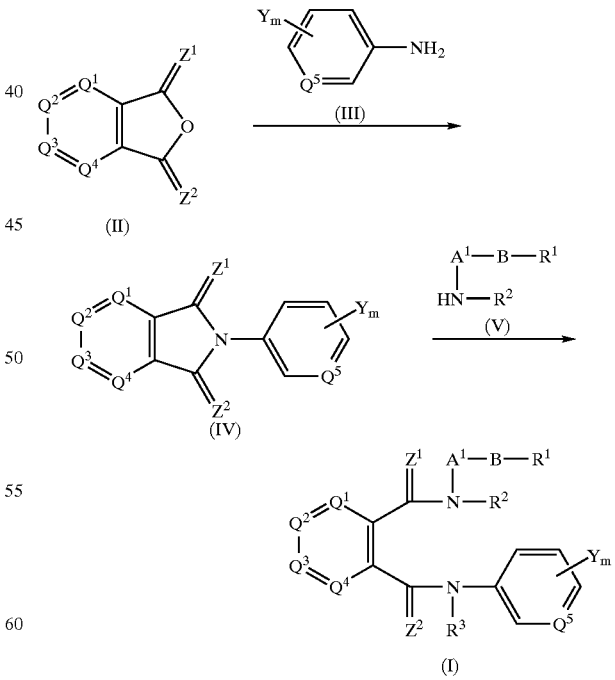

(wherein $R^1$, $R^2$, $A^1$, B, $Q^1$ to $Q^5$, Y, m, $Z^1$ and $Z^2$ each have the same definition as given above).

A carboxylic anhydride derivative represented by the general formula (II) is reacted with an amine represented by the general formula (III) in the presence of an inert solvent to obtain an imide derivative represented by the general formula (IV); the imide derivative (IV) is reacted, after being isolated or without being isolated, with an amine represented by the general formula (V); thereby, an aromatic diamide derivative represented by the general formula (I) can be produced.

(1) General Formula (II)→General Formula (IV)

The inert solvent usable in the present reaction can be any solvent as long as it does not impair the progress of the present reaction. It can be exemplified by aromatic hydrocarbons such as benzene, toluene, xylene and the like; halogenated hydrocarbons such as methylene chloride, chloroform, carbon tetrachloride and the like; chlorinated aromatic hydrocarbons such as chlorobenzene, dichlorobenzene and the like; chain or cyclic ethers such as diethyl ether, dioxane, tetrahydrofuran and the like; esters such as ethyl acetate and the like; amides such as dimethylformamide, dimethylacetamide and the like; acids such as acetic acid and the like; dimethyl sulfoxide; and 1,3-dimethyl-2-imidazolidinone. These inert solvents can be used singly or in admixture of two or more kinds.

Since the present reaction is an equimolar reaction, the individual reactants can be used by the same mole, but any reactant may be used in excess. The present reaction may be conducted under a dehydrating condition as necessary.

The reaction temperature can be room temperature to the refluxing temperature of the inert solvent used. The reaction time varies depending upon, for example, the size or temperature of reaction, but can appropriately be determined in a range of several minutes to 48 hours.

After the completion of the reaction, the reaction mixture containing an intended product is subjected to an isolation treatment according to an ordinary method and, as necessary, purification is conducted by recrystallization, column chromatography or the like, whereby the intended product can be obtained. The reaction mixture per se may be used in the next reaction without being subjected to the above isolation treatment for obtaining the intended product.

The carboxylic anhydride derivative represented by the general formula (II) can be produced by one of the processes described in J. Org. Chem., 52, 129 (1987); J. Am. Chem. Soc., L, 1865 (1929); ibidem, 6, 1542 (1941); etc. The amine represented by the general formula (III) can be produced by one of the processes described in J. Org. Chem., a, 1 (1964); Angew. Chem. Int. Ed. Engl., 24, 871 (1985); Synthesis, 1984, 667; Nippon Kagaku Kaishi, 1973, 2351; DE-2606982; JP-A-1-90163; etc. The amine represented by the general formula (V) can be produced by one of the processes described in Chem. Pharm. Bull., 30(5), 1921–1924 (1982); Jikken Kagaku Koza 22, Organic Synthesis IV (Amino Acids and Peptides) (1992); etc.

(2) General Formula (IV)→General Formula (I)

The inert solvent usable in the present reaction can be exemplified by those inert solvents usable in the above reaction (1).

Since the present reaction is an equimolar reaction, the individual reactants can be used by the same mole, but the amine represented by the general formula (V) may be used in excess.

The reaction temperature can be room temperature to the refluxing temperature of the inert solvent used. The reaction time varies depending upon, for example, the size or temperature of reaction, but can appropriately be determined in a range of several minutes to 48 hours.

After the completion of the reaction, the reaction mixture containing an intended product is subjected to an isolation treatment according to an ordinary method and, as necessary, purification is conducted by recrystallization, column chromatography or the like, whereby the intended product can be obtained.

Production process 2

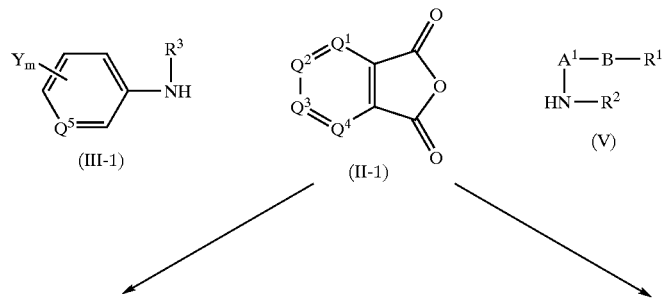

-continued

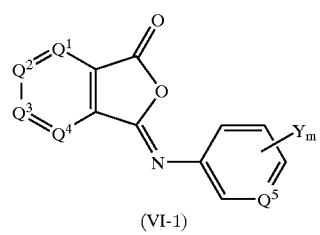
(VI-1)

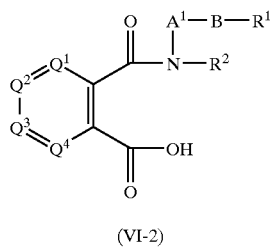
(VI-2)

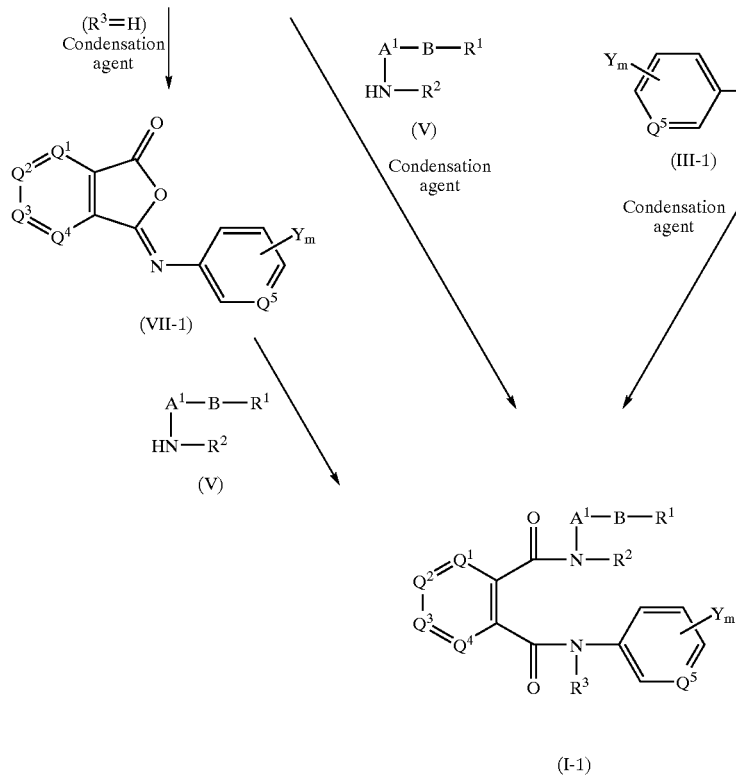

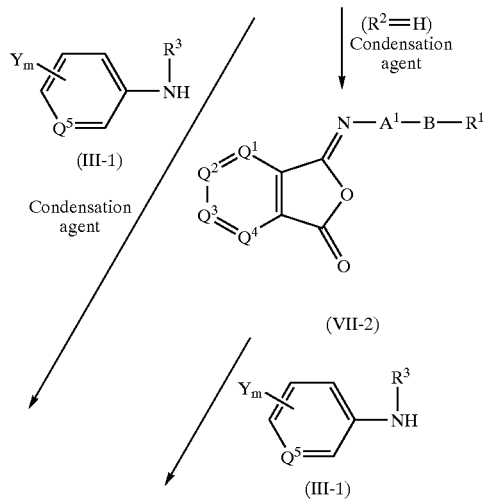

(I-1)

(wherein $R^1$, $R^2$, $R^3$, $A^1$, B, $Q^1$ to $Q^5$, Y and m each have the same definition as given above).

A carboxylic anhydride derivative represented by the general formula (II-1) is reacted with an amine represented by the general formula (V) in the presence of an inert solvent to obtain a carboxamide represented by the general formula (VI-2). This carboxamide (VI-2) is subjected to the following procedure after being isolated or without being isolated. That is, the carboxamide (VI-2), wherein $R^2$ is a hydrogen atom, is subjected to a condensation reaction in the presence of a condensation agent to obtain a compound represented by the general formula (VII-2); the compound (VII-2) is reacted, after being isolated or without being isolated, with an amine represented by the general formula (III-1) in the presence of an inert solvent; or, the carboxamide (VI-2), wherein $R^2$ is other than hydrogen atom, is condensed with an amine represented by the general formula (III-1) in the presence of a condensation agent; thereby, an aromatic diamide derivative represented by the general formula (I-1) can be produced.

Alternatively, a carboxylic anhydride derivative represented by the general formula (II-1) is reacted with an amine represented by the general formula (III-1) in the presence of an inert solvent to obtain a carboxamide represented by the general formula (VI-1). This carboxamide (VI-1) is subjected to the following procedure after being isolated or without being isolated. That is, the carboxamide (VI-1), wherein $R^3$ is a hydrogen atom, is subjected to a condensation reaction in the presence of a condensation agent to obtain a compound represented by the general formula (VII-1) and this compound (VII-1) is reacted, after being isolated or without being isolated, with an amine represented by the general formula. (V) in the presence of an inert solvent; or, the carboxamide (VI-1), wherein $R^3$ is other than hydrogen atom, is condensed with an amine represented by the general formula (V) in the presence of a condensation agent; thereby, an aromatic diamide derivative represented by the general formula (I-1) can be produced.

(1) General Formula (II-1)→General Formula (VI-1), or General Formula (II-1)→General Formula (VI-2)

The present reaction is conducted in the same manner as in the production process 1 (2), whereby an intended compound can be produced.

(2) General Formula (VII-1) or General Formula (VII-2) →General Formula (I-1)

The present reaction is conducted in the same manner as in the production process 1 (2), whereby an intended product can be produced.

(3) General Formula (VI-1)→General Formula (VII-1), or general formula (VI-2)→General Formula (VII-2)

The present reaction is conducted in the same manner as described in J. Med. Chem., 10, 982 (1967), whereby an intended compound can be produced.

(4) General formula (VI-1) or General Formula (VI-2) →General Formula (I-1)

A carboxamide derivative represented by the general formula (VI-1) or the general formula (VI-2) is reacted with an amine represented by the general formula (V) or the general formula (III-1) in the presence of a condensation agent and an inert solvent, whereby an intended compound can be produced. The present invention may be conducted in the presence of a base, as necessary.

The inert solvent used in the present reaction can be exemplified by tetrahydrofuran, diethyl ether, dioxane, methylene chloride and chloroform.

The condensation agent used in the present reaction can be any condensation agent used in ordinary amide production, and can be exemplified by Mukaiyama reagent (2-choro-N-methylpyridinium iodide), DCC (1,3-dicyclohexylcarbodiimide), CDI (carbonyl diimidazole) and DEPC (diethyl phosphoric cyanide). The amount of the condensation agent used can appropriately be determined at one or more moles per mole of the carboxamide represented by the general formula (VI-1) or the general formula (VI-2)

The base usable in the present reaction can be exemplified by organic bases (e.g. triethylamine and pyridine) and inorganic bases (e.g. potassium carbonate). The amount of the base used can appropriately be determined at one or more moles per mole of the carboxamide represented by the general formula (VI-1) or the general formula (VI-2).

The reaction temperature can be 0° C. to the boiling point of the inert solvent used. The reaction time varies depending upon, for example, the size or temperature of reaction, but is several minutes to 48 hours.

After the completion of the reaction, the reaction mixture containing an intended product is subjected to an isolation treatment according to an ordinary method and, as necessary, purification is conducted by recrystallization, column chromatography or the like, whereby the intended product can be obtained.

Representative compounds of the aromatic diamide derivative represented by the general formula (I) are shown below in Table 1, Table 2 and Table 3. However, the present aromatic diamide derivative is not restricted to these compounds. In the following tables, Me refers to methyl group; Et refers to ethyl group; Pr refers to propyl group; Bu refers to butyl group; Ph refers to phenyl group; Pyr refers to pyridyl group; c– refers to alicyclic hydrocarbon group; and Physical property refers to melting point (° C.).

In Table 1, with respect to $Q^1$ to $Q^4$ which are each C—X, $Q^1$ is at 3-position; $Q^2$ is at 4-position; $Q^3$ is at 5-position; and $Q^4$ is at 6-position.

TABLE 1

General formula (I)

($Q^1 = Q^2 = Q^3 = Q^4 = $ C—X, $Q^5 = $ C, $Z^1 = Z^2 = $ O, $R^3 = $ H)

| No. | —$A^1$—B—$R^1$ | $R^2$ | X | Ym | Physical property |
|---|---|---|---|---|---|
| 1 | $CH_2CO_2Et$ | H | 3-F | 2-Me-4-$CF(CF_3)_2$ | 120 |
| 2 | $CH_2CO_2Et$ | H | 3-Cl | 2-Me-4-$CF(CF_3)_2$ | 103 |
| 3 | $CH_2CO_2Et$ | H | 3-Br | 2-Me-4-$CF(CF_3)_2$ | 134 |
| 4 | $CH_2CO_2Et$ | H | 3-I | 2-Me-4-$CF(CF_3)_2$ | 120 |
| 5 | $CH(Me)CO_2Et$ | H | 3-F | 2-Me-4-$CF(CF_3)_2$ | 140 |
| 6 | $CH(Me)CO_2Et$ | H | 3-I | 2-Me-4-$CF(CF_3)_2$ | 145 |
| 7 | $CH(Me)CH_2CO_2Et$ | H | 3-F | 2-Me-4-$CF(CF_3)_2$ | 88 |
| 8 | $CH_2CH_2CO_2Et$ | H | 3-I | 2-Me-4-$CF_2CF_3$ | 112 |
| 9 | $CH_2CH_2CO_2Et$ | H | 3-I | 2-Me-4-$CF(CF_3)_2$ | 133 |
| 10 | $CH_2CH_2CO_2Et$ | H | 6-I | 2-Me-4-$CF(CF_3)_2$ | 164 |
| 11 | $CH(Me)CH_2CO_2Et$ | H | 3-I | 2-Me-4-$CF(CF_3)_2$ | paste |
| 12 | $CH(Me)CH_2CO_2Me$ | H | 3-I | 2-Me-4-$CF(CF_3)_2$ | |
| 13 | $CH(Me)CH_2CO_2Pr$-i | H | 3-I | 2-Me-4-$CF(CF_3)_2$ | |
| 14 | $CH(Me)CH_2CO_2Bu$-t | H | 3-I | 2-Me-4-$CF(CF_3)_2$ | |
| 15 | $CH(Me)CH_2CO_2Et$ | H | 4-I | 2-Me-4-$CF(CF_3)_2$ | |
| 16 | $CH(Me)CH_2CO_2Et$ | H | 3-$CF_3$ | 2-Me-4-$CF_2CF_3$ | |
| 17 | $CH(Me)CH_2CO_2Et$ | H | 3-$OCF_3$ | 2-Cl-4-$CF(CF_3)_2$ | |
| 18 | $CH(Me)CH_2CO_2Et$ | H | 3-I | 2-Et-4-$CF(CF_3)_2$ | |
| 19 | $CH(Me)CH_2CO_2Et$ | H | 3-I | 2-Me-4-CH=C(Cl)$CF_3$ | |
| 20 | $CH(Me)CH_2CO_2Et$ | H | 3-I | 2-Me-4-CH=$CBr_2$ | |
| 21 | $CH(Me)CH_2CO_2Et$ | H | 3-I | 4-$CO_2CH(CF_3)_2$ | |
| 22 | $CH(Me)CH_2CO_2Et$ | H | 3-I | 2-Me-4-C≡C-(2,4-$Cl_2$—Ph) | |
| 23 | $CH(Me)CH_2CO_2Et$ | H | 3-I | 2-Me-4-C≡C—Bu-t | |
| 24 | $CH(Me)CH_2CO_2Et$ | H | 3-$CF_3$ | 2-F-4-$CF_2CF_3$ | |
| 25 | $CH(Me)CH_2CO_2Et$ | H | 3-I | 2-OMe-4-$CF(CF_3)_2$ | |
| 26 | $CH(Me)CH_2CO_2Et$ | H | 3-I | 2-Me-4-C($CH_3$)=NOMe | |
| 27 | $CH(Me)CH_2CO_2Et$ | H | 3-I | 2-Me-4-C($CH_3$)=NO—$CH_2$—Ph | |
| 28 | $CH(Me)CH_2CO_2Et$ | H | 3-I | 3-$OCF_2CF_2O$-4 | |

TABLE 1-continued

General formula (I)

$(Q^1 = Q^2 = Q^3 = Q^4 = C-X, Q^5 = C, Z^1 = Z^2 = O, R^3 = H)$

| No. | —A¹—B—R¹ | R² | X | Ym | Physical property |
|---|---|---|---|---|---|
| 29 | CH(Me)CH₂CO₂Et | H | 3-I | 3-OCF₂CF₂-4 | |
| 30 | CH(Me)CH₂CO₂Et | H | 3-I | 2-Cl-3-OCF₂CF₂O-4 | |
| 31 | CH(Me)CH₂CO₂Et | H | 3-I | 3-OCF₂O-4 | |
| 32 | CH(Me)CH₂CO₂Et | H | 3-I | 3-OCHFCF₂O-4 | |
| 33 | CH(Me)CH₂CO₂Et | H | 3-I | 3-OCF₃CHFO-4 | |
| 34 | CH(Me)CH₂CO₂Et | H | 3-I | 2-Me-3-F-4-CF(CF₃)₂ | |
| 35 | CH(Me)CH₂CO₂Et | H | 3-I | 2-Me-5-F-4-CF(CF₃)₂ | |
| 36 | CH(Me)CH₂CO₂Et | H | 3-I | 2-Me-4-(4-CF₃—Ph) | |
| 37 | CH(Me)CH₂CO₂Et | H | 3-I | 2-Me-4-(4-Cl—Ph) | |
| 38 | CH(Me)CH₂CO₂Et | H | 3-I | 2-Me-4-(4-Cl—PhO) | |
| 39 | CH(Me)CO₂Et | H | 3-I | 2-Me-4-OCF₃ | |
| 40 | CH(Me)CO₂Et | H | 3-I | 2-Me-4-OCF₂CF₃ | |
| 41 | CH(Me)CO₂Et | H | 3-I | 2-Me-4-CF₃ | |
| 42 | CH(Me)CO₂Et | H | 3-I | 2-Me-3-CF₂CF₃ | |
| 43 | CH(Me)CO₂Et | H | 3-I | 2-Me-4-SCF₃ | |
| 44 | CH(Me)CO₂Et | H | 3-I | 2-Me-4-SOCF₃ | |
| 45 | CH(Me)CO₂Et | H | 3-I | 2-Me-4-SO₂CF₃ | |
| 46 | CH(Me)CH₂CO₂Et | H | 3-I | 2-Me-4-SCF₂CF₃ | |
| 47 | CH(Me)CO₂Et | H | 3-I | 2-Me-4-OCF₂CHFOCF₃ | |
| 48 | CH(Me)CO₂Et | H | 3-I | 2-Me-4-(5-CF₃-2-Pyr—O) | |
| 49 | CH(Me)CO₂Et | H | 3-Cl | 2-Me-4-(3-Cl-5-CF₃-2-Pyr—O) | |
| 50 | CH(Me)CH₂CO₂Et | H | 3-NO₂ | 2-Me-4-CF(CF₃)₂ | |
| 51 | CH(Me)CH₂CO₂Et | H | 3,4-Cl₂ | 2-Me-4-CF(CF₃)₂ | |
| 52 | CH(Me)CH₂CO₂Et | H | 3-SCF₃ | 2-Me-4-CF(CF₃)₂ | |
| 53 | CH(Me)CH₂CO₂Et | H | 3-SOCF₃ | 2-Me-4-CF(CF₃)₂ | |
| 54 | CH(Me)CH₂CO₂Et | H | 3-SO₂CF₃ | 2-Me-4-CF(CF₃)₂ | |
| 55 | CH(Me)CH₂CO₂Et | H | 3-Ph | 2-Me-4-CF(CF₃)₂ | |
| 56 | CH(Me)CH₂CO₂Et | H | 3-OPh | 2-Me-4-CF(CF₃)₂ | |
| 57 | CH(Me)CH₂CO₂Et | H | 3-(4-Cl—Pho) | 2-Me-4-CF(CF₃)₂ | |
| 58 | CH(Me)CO₂Et | H | 3-I | 2-Me-4-Cl | |
| 59 | CH(Me)CO₂Et | H | 3-CONHPr-i | 2-Me-4-Cl | |
| 60 | CH(Me)CH₂CO₂Et | H | 3-CH=CH—CH=CH-4 | 2-Me-4-Cl | |
| 61 | CH(Me)CH₂CO₂Et | Me | 3-I | 2-Me-4-CF(CF₃)₂ | |
| 62 | CH(Me)CH₂CO₂Et | Et | 3-I | 2-Me-4-CF(CF₃)₂ | |
| 63 | C(Me)₂C≡CCO₂Et | H | 3-I | 2-Me-4-CF(CF₃)₂ | |
| 64 | C(Me)₂CH=CHCO₂Et | H | 3-I | 2-Me-4-CF(CF₃)₂ | 250 |
| 65 | CH(CH₂SMe)CH₂CO₂Et | H | 3-I | 2-Me-4-CF(CF₃)₂ | |
| 66 | CH(CF₃)CH₂CO₂Et | H | 3-I | 2-Me-4-CF(CF₃)₂ | |
| 67 | CH(CH₂OMe)CH₂CO₂Et | H | 3-I | 2-Me-4-CF(CF₃)₂ | |
| 68 | CH(Ph)CH₂CO₂Et | H | 3-I | 2-Me-4-CF(CF₃)₂ | |
| 69 | CH(4-Cl—Ph)CH₂CO₂Et | H | 3-I | 2-Me-4-CF(CF₃)₂ | |
| 70 | CH(Me)CON(Me)₂ | H | 3-I | 2-Me-4-CF₂CF₃ | 122 |
| 71 | CH(Me)CON(Me)₂ | H | 3-I | 2-Me-4-CF(CF₃)₂ | 156 |
| 72 | CH(Me)CON(Et)₂ | H | 3-I | 2-Me-4-CF(CF₃)₂ | 133 |
| 73 | CH(Me)CH₂CONHMe | H | 3-I | 2-Me-4-CF(CF₃)₂ | 220 |
| 74 | CH(Me)CH₂CONHEt | H | 3-I | 2-Me-4-CF(CF₃)₂ | 208 |
| 75 | CH(Me)CH₂CON(Me)Ph | H | 3-I | 2-Me-4-CF(CF₃)₂ | 200 |
| 76 | CH(Me)CH₂CON(Me)₂ | H | 3-I | 2-Me-4-CF₂CF₃ | 102 |
| 77 | CH(Me)CH₂CON(Me)₂ | H | 3-I | 2-Me-4-CF(CF₃)₂ | 126 |
| 78 | CH(Me)CH₂CON(Et)₂ | H | 3-I | 2-Me-4-CF(CF₃)₂ | 137 |
| 79 | CH(Me)CH₂CONHEt | H | 4-I | 2-Me-4-CF(CF₃)₂ | |
| 80 | CH(Me)CH₂CONHEt | H | 3-CF₃ | 2-Me-4-CF₂CF₃ | |
| 81 | CH(Me)CH₂CONHEt | H | 3-OCF₃ | 2-Cl-4-CF(CF₃)₂ | |
| 82 | CH(Me)CH₂CONHEt | H | 3-I | 2-Et-4-CF(CF₃)₂ | |
| 83 | CH(Me)CH₂CONHEt | H | 3-I | 2-Me-4-CH=C(Cl)CF₃ | |
| 84 | CH(Me)CH₂CONHEt | H | 3-I | 2-Me-4-CH=CBr₂ | |
| 85 | CH(Me)CON(Et)₂ | H | 3-I | 4-CO₂CH(CF₃)₂ | |

TABLE 1-continued

General formula (I)

$(Q^1 = Q^2 = Q^3 = Q^4 = C-X, Q^5 = C, Z^1 = Z^2 = O, R^3 = H)$

| No. | —A¹—B—R¹ | R² | X | Ym | Physical property |
|---|---|---|---|---|---|
| 86 | CH(Me)CON(Et)₂ | H | 3-I | 2-Me-4-C≡C-(2,4-Cl₂—Ph) | |
| 87 | CH(Me)CH₂CONHEt | H | 3-I | 2-Me-4-C≡C—Bu-t | |
| 88 | CH(Me)CH₂CON(Et)₂ | H | 3-CF₃ | 2-F-4-CF₂CF₃ | |
| 89 | CH(Me)CH₂CON(Et)₂ | H | 3-I | 2-OMe-4-CF(CF₃)₂ | |
| 90 | CH(Me)CH₂CON(Et)₂ | H | 3-I | 2-Me-4-C(CH₃)=NOMe | |
| 91 | CH(Me)CH₂CON(Et)₂ | H | 3-I | 2-Me-4-C(CH₃)=NO—CH₂—Ph | |
| 92 | CH(Me)CH₂CON(Et)₂ | H | 3-I | 3-OCF₂CF₂O-4 | |
| 93 | CH(Me)CH₂CONHEt | H | 3-I | 3-OCF₂CF₂-4 | |
| 94 | CH(Me)CON(Et)₂ | H | 3-I | 2-Cl-3-OCF₂CF₂O-4 | |
| 95 | CH(Me)CH₂CON(Et)₂ | H | 3-I | 3-OCF₂O-4 | |
| 96 | CH(Me)CH₂CONHEt | H | 3-I | 3-OCHFCF₂O-4 | |
| 97 | CH(Me)CON(Et)₂ | H | 3-I | 3-OCF₂CHFO-4 | |
| 98 | CH(Me)CH₂CON(Et)₂ | H | 3-I | 2-Me-3-F-4-CF(CF₃)₂ | |
| 99 | CH(Me)CH₂CONHEt | H | 3-I | 2-Me-5-F-4-CF(CF₃)₂ | |
| 100 | CH(Me)CON(Et)₂ | H | 3-I | 2-Me-4-(4-CF₃—Ph) | |
| 101 | CH(Me)CH₂CON(Et)₂ | H | 3-I | 2-Me-4-(4-Cl—Ph) | |
| 102 | CH(Me)CH₂CONHEt | H | 3-I | 2-Me-4-(4-Cl—PhO) | |
| 103 | CH(Me)CON(Et)₂ | H | 3-I | 2-Me-4-OCF₃ | |
| 104 | CH(Me)CH₂CON(Et)₂ | H | 3-I | 2-Me-4-OCF₂CF₃ | |
| 105 | CH(Me)CH₂CONHEt | H | 3-I | 2-Me-4-CF₃ | |
| 106 | CH(Me)CH₂CONHEt | H | 3-I | 2-Me-3-CF₂CF₃ | |
| 107 | CH(Me)CON(Et)₂ | H | 3-I | 2-Me-4-SCF₃ | |
| 108 | CH(Me)CH₂CON(Et)₂ | H | 3-I | 2-Me-4-SOCF₃ | |
| 109 | CH(Me)CH₂CONHEt | H | 3-I | 2-Me-4-SO₂CF₃ | |
| 110 | CH(Me)CH₂CONHEt | H | 3-I | 2-Me-4-SCF₂CF₃ | |
| 111 | CH(Me)CON(Et)₂ | H | 3-I | 2-Me-4-OCF₂CHFOCF₃ | |
| 112 | CH(Me)CH₂CON(Et)₂ | H | 3-I | 2-Me-4-(5-CF₃-2-Pyr—O) | |
| 113 | CH(Me)CH₂CONHEt | H | 3-Cl | 2-Me-4-(3-Cl-5-CF₃-2-Pyr—O) | |
| 114 | CH(Me)CH₂CONHEt | H | 3-NO₂ | 2-Me-4-CF(CF₃)₂ | |
| 115 | CH(Me)CON(Et)₂ | H | 3,4-Cl₂ | 2-Me-4-CF(CF₃)₂ | |
| 116 | CH(Me)CH₂CON(Et)₂ | H | 3-SCF₃ | 2-Me-4-CF(CF₃)₂ | |
| 117 | CH(Me)CH₂CONHEt | H | 3-SOCF₃ | 2-Me-4-CF(CF₃)₂ | |
| 118 | CH(Me)CH₂CONHEt | H | 3-SO₂CF₃ | 2-Me-4-CF(CF₃)₂ | |
| 119 | CH(Me)CON(Et)₂ | H | 3-Ph | 2-Me-4-CF(CF₃)₂ | |
| 120 | CH(Me)CH₂CON(Et)₂ | H | 3-OPh | 2-Me-4-CF(CF₃)₂ | |
| 121 | CH(Me)CH₂CONHEt | H | 3-(4-Cl—PhO) | 2-Me-4-CF(CF₃)₂ | |
| 122 | CH(Me)CON(Et)₂ | H | 3-I | 2-Me-4-Cl | |
| 123 | CH(Me)CH₂CON(Et)₂ | H | 3-CONHPr-i | 2-Me-4-Cl | |
| 124 | CH(Me)CH₂CONHEt | H | 3-CH=CH—CH=CH-4 | 2-Me-4-Cl | |
| 125 | CH(Me)CON(Et)₂ | Me | 3-I | 2-Me-4-CF(CF₃)₂ | |
| 126 | CH(Me)CH₂CON(Et)₂ | Et | 3-I | 2-Me-4-CF(CF₃)₂ | |
| 127 | C(Me)₂C≡CCON(Et)₂ | H | 3-I | 2-Me-4-CF(CF₃)₂ | |
| 128 | C(Me)₂CH=CHCON(Et)₂ | H | 3-I | 2-Me-4-CF(CF₃)₂ | |
| 129 | CH(CH₂SMe)CH₂CON(Et)₂ | H | 3-I | 2-Me-4-CF(CF₃)₂ | |
| 130 | CH(CF₃)CH₂CONHEt | H | 3-I | 2-Me-4-CF(CF₃)₂ | |
| 131 | CH(CH₂OMe)—CH₂CONHEt | H | 3-I | 2-Me-4-CF(CF₃)₂ | |
| 132 | CH(Ph)CH₂CON(Et)₂ | H | 3-I | 2-Me-4-CF(CF₃)₂ | |
| 133 | CH(4-Cl—Ph)—CH₂CONHEt | H | 3-I | 2-Me-4-CF(CF₃)₂ | |
| 134 | CH(Me)COMe | H | 3-I | 2-Me-4-CF(CF₃)₂ | 189 |
| 135 | CH(Me)COPh | H | 3-I | 2-Me-4-CF(CF₃)₂ | 171 |

TABLE 1-continued

General formula (I)

$(Q^1 = Q^2 = Q^3 = Q^4 = C-X, Q^5 = C, Z^1 = Z^2 = O, R^3 = H)$

| No. | —A¹—B—R¹ | R² | X | Ym | Physical property |
|---|---|---|---|---|---|
| 136 | CH(Me)CH=NOMe | H | 3-I | 2-Me-4-CF(CF$_3$)$_2$ | 192 |
| 137 | CH(Me)CH=NOMe | H | 6-I | 2-Me-4-CF(CF$_3$)$_2$ | paste |
| 138 | CH(Me)CH=NOCH$_2$Ph | H | 3-I | 2-Me-4-CF(CF$_3$)$_2$ | paste |
| 139 | C(Me)$_2$CH=NOMe | H | 3-I | 2-Me-4-CF(CF$_3$)$_2$ | 126 |
| 140 | CH(Me)C(Me)=NOMe | H | 3-I | 2-Me-4-CF(CF$_3$)$_2$ | 107 |
| 141 | CH$_2$C(Ph)=NOMe | H | 3-I | 2-Me-4-CF(CF$_3$)$_2$ | 106 |
| 142 | CH(Me)CH=NOMe | H | 4-I | 2-Me-4-CF(CF$_3$)$_2$ | |
| 143 | CH(Me)C(Me)=NOMe | H | 3-CF$_3$ | 2-Me-4-CF$_2$CF$_3$ | |
| 144 | CH(Me)CH=NOMe | H | 3-OCF$_3$ | 2-Cl-4-CF(CF$_3$)$_2$ | |
| 145 | C(Me)$_2$CH=NOMe | H | 3-I | 2-Et-4-CF(CF$_3$)$_2$ | |
| 146 | CH(Me)CH=NOMe | H | 3-I | 2-Me-4-CH=C(Cl)CF$_3$ | |
| 147 | CH(Me)C(Me)=NOMe | H | 3-I | 2-Me-4-CH=CBr$_2$ | |
| 148 | CH(Me)CH=NOMe | H | 3-I | 4-CO$_2$CH(CF$_3$)$_2$ | |
| 149 | C(Me)$_2$CH=NOMe | H | 3-I | 2-Me-4-C≡C-(2,4-Cl$_2$—Ph) | |
| 150 | CH(Me)CH=NOMe | H | 3-I | 2-Me-4-C≡C—Bu-t | |
| 151 | CH$_2$C(Me)=NOMe | H | 3-CF$_3$ | 2-F-4-CF$_2$CF$_3$ | |
| 152 | CH(Me)CH=NOMe | H | 3-I | 2-OMe-4-CF(CF$_3$)$_2$ | |
| 153 | C(Me)$_2$CH=NOMe | H | 3-I | 2-Me-4-C(CH$_3$)=NOMe | |
| 154 | CH(Me)CH=NOMe | H | 3-I | 2-Me-4-C(CH$_3$)=NO—CH$_2$—Ph | |
| 155 | CH(Me)C(Me)=NOMe | H | 3-I | 3-OCF$_2$CF$_2$O-4 | |
| 156 | CH(Me)CH=NOMe | H | 3-I | 3-OCF$_2$CF$_2$-4 | |
| 157 | C(Me)$_2$CH=NOMe | H | 3-I | 2-Cl-3-OCF$_2$CF$_2$O-4 | |
| 158 | CH(Me)C(Me)=NOMe | H | 3-I | 3-OCF$_2$O-4 | |
| 159 | CH(Me)CH=NOMe | H | 3-I | 3-OCHFCF$_2$O-4 | |
| 160 | C(Me)$_2$CH=NOMe | H | 3-I | 3-OCF$_2$CHFO-4 | |
| 161 | CH(Me)CH=NOMe | H | 3-I | 2-Me-3-F-4-CF(CF$_3$)$_2$ | |
| 162 | CH(Me)C(Me)=NOMe | H | 3-I | 2-Me-5-F-4-CF(CF$_3$)$_2$ | |
| 163 | CH(Me)CH=NOMe | H | 3-I | 2-Me-4-(4-CF$_3$—Ph) | |
| 164 | C(Me)$_2$CH=NOMe | H | 3-I | 2-Me-4-(4-Cl—Ph) | |
| 165 | CH(Me)CH=NOMe | H | 3-I | 2-Me-4-(4-Cl—PhO) | |
| 166 | CH(Me)C(Me)=NOMe | H | 3-I | 2-Me-4-OCF$_3$ | |
| 167 | CH(Me)CH=NOMe | H | 3-I | 2-Me-4-OCF$_2$CF$_3$ | |
| 168 | C(Me)$_2$CH=NOMe | H | 3-I | 2-Me-4-CF$_3$ | |
| 169 | CH(Me)CH=NOMe | H | 3-I | 2-Me-3-CF$_2$CF$_3$ | |
| 170 | CH(Me)C(Me)=NOMe | H | 3-I | 2-Me-4-SCF$_3$ | |
| 171 | CH(Me)CH=NOMe | H | 3-I | 2-Me-4-SOCF$_3$ | |
| 172 | C(Me)$_2$CH=NOMe | H | 3-I | 2-Me-4-SO$_2$CF$_3$ | |
| 173 | CH(Me)CH=NOMe | H | 3-I | 2-Me-4-SCF$_2$CF$_3$ | |
| 174 | CH(Me)CH=NOMe | H | 3-I | 2-Me-4-OCF$_2$CHFOCF$_3$ | |
| 175 | C(Me)$_2$CH=NOMe | H | 3-I | 2-Me-4-(5-CF$_3$-2-Pyr—O) | |
| 176 | CH(Me)CH=NOMe | H | 3-Cl | 2-Me-4-(3-Cl-5-CF$_3$-2-Pyr—O) | |
| 177 | C(Me)$_2$CH=NOMe | H | 3-NO$_2$ | 2-Me-4-CF(CF$_3$)$_2$ | 149 |
| 178 | CH(Me)CH=NOMe | H | 3,4-Cl$_2$ | 2-Me-4-CF(CF$_3$)$_2$ | |
| 179 | CH(Me)CH=NOMe | H | 3-SCF$_3$ | 2-Me-4-CF(CF$_3$)$_2$ | |
| 180 | C(Me)$_2$CH=NOMe | H | 3-SOCF$_3$ | 2-Me-4-CF(CF$_3$)$_2$ | |
| 181 | CH(Me)CH=NOMe | H | 3-SO$_2$CF$_3$ | 2-Me-4-CF(CF$_3$)$_2$ | |
| 182 | C(Me)$_2$CH=NOMe | H | 3-Ph | 2-Me-4-CF(CF$_3$)$_2$ | |
| 183 | CH(Me)CH=NOMe | H | 3-OPh | 2-Me-4-CF(CF$_3$)$_2$ | |
| 184 | CH(Me)CH=NOMe | H | 3-(4-Cl—PhO) | 2-Me-4-CF(CF$_3$)$_2$ | |
| 185 | C(Me)$_2$CH=NOMe | H | 3-I | 2-Me-4-Cl | |
| 186 | CH(Me)CH=NOMe | H | 3-CONHPr-i | 2-Me-4-Cl | |
| 187 | CH(Me)CH=NOMe | H | 3-CH=CH—CH=CH-4 | 2-Me-4-Cl | |
| 188 | CH(Me)CH=NOMe | Me | 3-I | 2-Me-4-CF(CF$_3$)$_2$ | |
| 189 | CH(Me)CH=NOMe | Et | 3-I | 2-Me-4-CF(CF$_3$)$_2$ | |
| 190 | CH(CH$_2$SMe)CH=NOMe | H | 3-I | 2-Me-4-CF(CF$_3$)$_2$ | |
| 191 | CH(CF$_3$)CH=NOEt | H | 3-I | 2-Me-4-CF(CF$_3$)$_2$ | |

TABLE 1-continued

General formula (I)

($Q^1 = Q^2 = Q^3 = Q^4 = C-X$, $Q^5 = C$, $Z^1 = Z^2 = O$, $R^3 = H$)

| No. | —$A^1$—B—$R^1$ | $R^2$ | X | Ym | Physical property |
|---|---|---|---|---|---|
| 192 | CH(CH$_2$OMe)CH=NOMe | H | 3-I | 2-Me-4-CF(CF$_3$)$_2$ | |
| 193 | CH(Ph)CH=NOMe | H | 3-I | 2-Me-4-CF(CF$_3$)$_2$ | |
| 194 | CH(Me)CH$_2$CH=NOMe | H | 3-I | 2-Me-4-CF(CF$_3$)$_2$ | |
| 195 | CH(Me)CH=NOCH$_2$-(4-t-Bu—Ph) | H | 3-I | 2-Me-4-CF(CF$_3$)$_2$ | |
| 196 | CH(Me)CH=NOCH$_2$-(4-t-BuO$_2$C—Ph) | H | 3-I | 2-Me-4-CF(CF$_3$)$_2$ | |
| 197 | CH(Me)CO$_2$CH$_2$CH$_2$OEt | H | 3-I | 2-Me-4-CF(CF$_3$)$_2$ | |
| 198 | CH(Me)CO$_2$CH$_2$CH$_2$SEt | H | 3-I | 2-Me-4-CF(CF$_3$)$_2$ | |
| 199 | CH(Me)CO$_2$CH$_2$—Ph | H | 3-I | 2-Me-4-CF(CF$_3$)$_2$ | |
| 200 | CH$_2$CH=CHCO$_2$Et | H | 3-I | 2-Me-4-CF(CF$_3$)$_2$ | |
| 201 | CH$_2$C≡CCO$_2$Et | H | 3-I | 2-Me-4-CF(CF$_3$)$_2$ | |
| 202 | CH(Me)CH=CHCO$_2$Et | H | 3-I | 2-Me-4-CF(CF$_3$)$_2$ | |
| 203 | CH(Me)C≡CCO$_2$Et | H | 3-I | 2-Me-4-CF(CF$_3$)$_2$ | |
| 204 | CH(Me)CONHEt | H | 3-I | 2-Me-4-CF(CF$_3$)$_2$ | 210 |
| 205 | CH(Me)CONHPr-n | H | 3-I | 2-Me-4-CF(CF$_3$)$_2$ | 201 |
| 206 | CH(Me)CONHPr-c | H | 3-I | 2-Me-4-CF(CF$_3$)$_2$ | |
| 207 | CH(Me)CONHBu-n | H | 3-I | 2-Me-4-CF(CF$_3$)$_2$ | 214 |
| 208 | CH(Me)CONHCH$_2$CH=CH$_2$ | H | 3-I | 2-Me-4-CF(CF$_3$)$_2$ | |
| 209 | CH(Me)CONHCH$_2$C≡CH | H | 3-I | 2-Me-4-CF(CF$_3$)$_2$ | |
| 210 | CH(Me)CONHCH$_2$CF$_3$ | H | 3-I | 2-Me-4-CF(CF$_3$)$_2$ | |
| 211 | CH(Me)CONHCH$_2$CH$_2$SMe | H | 3-I | 2-Me-4-CF(CF$_3$)$_2$ | |
| 212 | CH(Me)CONHCH$_2$CH$_2$SOMe | H | 3-I | 2-Me-4-CF(CF$_3$)$_2$ | |
| 213 | CH(Me)CONHCH$_2$CH$_2$—SO$_2$Me | H | 3-I | 2-Me-4-CF(CF$_3$)$_2$ | |
| 214 | CH(Me)CONHCH$_2$CH$_2$OMe | H | 3-I | 2-Me-4-CF(CF$_3$)$_2$ | |
| 215 | CH(Me)CONHCH$_2$—Ph | H | 3-I | 2-Me-4-CF(CF$_3$)$_2$ | 212 |
| 216 | CH(Me)CON(n-Pr)$_2$ | H | 3-I | 2-Me-4-CF(CF$_3$)$_2$ | 142 |
| 217 | CH(Me)CON(CH$_2$CH$_2$)$_2$O | H | 3-I | 2-Me-4-CF(CF$_3$)$_2$ | 165 |
| 218 | CH(Me)CON(CH$_2$)$_5$ | H | 3-I | 2-Me-4-CF(CF$_3$)$_2$ | 170 |
| 219 | CH(Me)CON(CH$_2$)$_4$ | H | 3-I | 2-Me-4-CF(CF$_3$)$_2$ | 205 |
| 220 | C(Me)$_2$CONHEt | H | 3-I | 2-Me-4-CF(CF$_3$)$_2$ | |
| 221 | C(Me)$_2$CONHPr-n | H | 3-I | 2-Me-4-CF(CF$_3$)$_2$ | |
| 222 | CH(Me)CONHCH$_2$CH=CH$_2$ | H | 3-I | 2-Me-4-CF(CF$_3$)$_2$ | |
| 223 | CH(Me)CONHCH$_2$C≡CH | H | 3-I | 2-Me-4-CF(CF$_3$)$_2$ | |
| 224 | CH(Me)CH=CHCONHMe | H | 3-I | 2-Me-4-CF(CF$_3$)$_2$ | |
| 225 | CH(Me)C≡CCONHEt | H | 3-I | 2-Me-4-CF(CF$_3$)$_2$ | |
| 226 | C(Me)$_2$CH=CHCONHEt | H | 3-I | 2-Me-4-CF(CF$_3$)$_2$ | 245 |
| 227 | C(Me)$_2$C≡CCONHEt | H | 3-I | 2-Me-4-CF(CF$_3$)$_2$ | |
| 228 | CH(Me)C(=O)H | H | H | 2-Me-4-OCF$_3$ | 134 |
| 229 | C(Me)$_2$C(=O)H | H | H | 2-Me-4-OCF$_3$ | 150 |
| 230 | C(Me)$_2$C(=O)H | H | H | 2-Me-4-OCF$_2$CHFOC$_3$F$_7$-n | 159 |
| 231 | C(Me)$_2$C(=O)H | H | H | 2-Me-4-OCF$_2$CHFCF$_3$ | 171 |
| 232 | C(Me)$_2$C(=O)H | H | H | 2-Me-4-O-(3-Cl-5-CF$_3$-2-Pyr) | 159 |
| 233 | C(Me)$_2$C(=O)H | H | H | 2-Me-4-Cl | 229 |
| 234 | C(Me)$_2$C(=O)H | H | H | 2-Me-4-CF$_3$ | 87 |
| 235 | C(Me)$_2$C(=O)H | H | H | 2-Me-4-CF$_2$CF$_2$CF$_3$ | 143 |
| 236 | C(Me)$_2$C(=O)H | H | H | 2-Me-4-CF(CF$_3$)$_2$ | 214 |
| 237 | C(Me)$_2$C(=O)H | H | 3-NO$_2$ | 2-Me-4-CF(CF$_3$)$_2$ | 262 |
| 238 | C(Me)$_2$C(=O)H | H | 3-F | 2-Me-4-CF(CF$_3$)$_2$ | 146 |
| 239 | C(Me)$_2$C(=O)H | H | 3,4-Cl$_2$ | 2-Me-4-CF(CF$_3$)$_2$ | 166 |
| 240 | (CH$_2$)$_2$C(=O)H | H | 3-I | 2-Me-4-CF(CF$_3$)$_2$ | 128 |
| 241 | CH(CH$_2$SO$_2$Me)C(=O)H | H | 3-I | 2-Me-4-CF(CF$_3$)$_2$ | 106 |
| 242 | C(Me)(CH$_2$SO$_2$Me)—C(=O)H | H | 3-I | 2-Me-4-CF(CF$_3$)$_2$ | 118 |
| 243 | C(Me)(CH$_2$SO$_2$Et)—C(=O)H | H | 3-I | 2-Me-4-CF(CF$_3$)$_2$ | 103 |
| 244 | C(Me)$_2$CH=NOH | H | H | 2-Me-4-OCF$_2$CHFCF$_3$ | 150 |
| 245 | C(Me)$_2$CH=NOH | H | H | 2-Me-4-CF$_2$CF$_3$ | 182 |
| 246 | C(Me)$_2$CH=NOH | H | 3-I | 2-Me-4-CF$_2$CF$_3$ | 189 |

TABLE 1-continued

General formula (I)

$(Q^1 = Q^2 = Q^3 = Q^4 = C-X, Q^5 = C, Z^1 = Z^2 = O, R^3 = H)$

| No. | —A$^1$—B—R$^1$ | R$^2$ | X | Ym | Physical property |
|---|---|---|---|---|---|
| 247 | C(Me)$_2$CH=NOH | H | 3-F | 2-Me-4-CF(CF$_3$)$_2$ | 242 |
| 248 | C(Me)$_2$CH=NOH | H | 3-I | 2-Me-4-CF(CF$_3$)$_2$ | 218 |
| 249 | C(Me)(CH$_2$SO$_2$Me)CH=NOH | H | 3-I | 2-Me-4-CF(CF$_3$)$_2$ | 106 |
| 250 | C(Me)(CH$_2$SO$_2$Et)CH=NOH | H | 3-I | 2-Me-4-CF(CF$_3$)$_2$ | 112 |
| 251 | CH$_2$CH=NOMe | Me | H | 2-Me-4-CF(CF$_3$)$_2$ | 127 |
| 252 | CH(Me)CH=NOMe | H | H | 2-Me-4-OCF$_3$ | 133 |
| 253 | CH(Me)CH=NOMe | H | 3-I | 2-Me-4-OCF$_3$ | 159 |
| 254 | CH(Me)CH=NOMe | H | 3-Br | 2-Me-4-OCF$_3$ | 168 |
| 255 | CH(Me)CH=NOMe | H | H | 2-Me-4-CF$_2$CF$_3$ | 130 |
| 256 | CH(Me)CH=NOMe | H | 3-I | 2-Me-4-CF$_2$CF$_3$ | 110 |
| 257 | CH(Me)CH=NOMe | H | 3-Cl | 2-Me-4-CF$_2$CF$_3$ | 154 |
| 258 | CH(Me)CH=NOMe | H | 3-Br | 2-Me-4-CF$_2$CF$_3$ | 162 |
| 259 | CH(Me)CH=NOMe | H | H | 2-Me-4-CF(CF$_3$)$_2$ | 154 |
| 260 | CH(Me)CH=NOMe | H | 3-OCF$_3$ | 2-Me-4-CF(CF$_3$)$_2$ | 165 |
| 261 | C(Me)$_2$CH=NOMe | H | H | 2-Me-4-OCHF$_2$ | 170 |
| 262 | C(Me)$_2$CH=NOMe | H | 3-I | 2-Me-4-OCHF$_2$ | 184 (E-form) |
| 263 | C(Me)$_2$CH=NOMe | H | 3-I | 2-Me-4-OCHF$_2$ | 182 (Z-form) |
| 264 | C(Me)$_2$CH=NOMe | H | H | 2-Me-4-OCF$_3$ | 195 |
| 265 | C(Me)$_2$CH=NOMe | H | 3-I | 2-Me-4-OCF$_3$ | 191 |
| 266 | C(Me)$_2$CH=NOMe | H | 3-Cl | 2-Me-4-OCF$_3$ | 199 |
| 267 | C(Me)$_2$CH=NOMe | H | 3-Br | 2-Me-4-OCF$_3$ | 184 |
| 268 | C(Me)$_2$CH=NOMe | H | 3,4-Cl$_2$ | 2-Me-4-OCF$_3$ | 212 |
| 269 | C(Me)$_2$CH=NOMe | H | H | 2-Me-4-OCF$_2$CHF$_2$ | 174 |
| 270 | C(Me)$_2$CH=NOMe | H | 3-I | 2-Me-4-OCF$_2$CHF$_2$ | 185 |
| 271 | C(Me)$_2$CH=NOMe | H | H | 2-Me-4-OCF$_2$CHFCF$_3$ | 160 |
| 272 | C(Me)$_2$CH=NOMe | H | H | 2-Me-4-OCF$_2$CHFOC$_3$F$_7$-n | 140 |
| 273 | C(Me)$_2$CH=NOMe | H | H | 2-Me-4-O-(3-Cl-5-CF$_3$-2-Pyr) | 151 |
| 274 | C(Me)$_2$CH=NOMe | H | H | 2-Me-4-Cl | 178 |
| 275 | C(Me)$_2$CH=NOMe | H | H | 2-Me-4-CF$_2$CF$_3$ | 200 |
| 276 | C(Me)$_2$CH=NOMe | H | 3-I-4-Cl | 2-Me-4-CF$_2$CF$_3$ | 225 |
| 277 | C(Me)$_2$CH=NOMe | H | 3-I | 2-Me-4-CF$_2$CF$_3$ | 147 |
| 278 | C(Me)$_2$CH=NOMe | H | 3-Cl | 2-Me-4-CF$_2$CF$_3$ | 202 |
| 279 | C(Me)$_2$CH=NOMe | H | 3-Br | 2-Me-4-CF$_2$CF$_3$ | 207 |
| 280 | C(Me)$_2$CH=NOMe | H | H | 2-Me-4-CF$_2$CF$_2$CF$_3$ | 174 |
| 281 | C(Me)$_2$CH=NOMe | H | H | 2-Me-4-CF(CF$_3$)$_2$ | 178 |
| 282 | C(Me)$_2$CH=NOMe | H | 4-CF$_3$ | 2-Me-4-CF(CF$_3$)$_2$ | 155 |
| 283 | C(Me)$_2$CH=NOMe | H | 3-OCF$_3$ | 2-Me-4-CF(CF$_3$)$_2$ | 186 |
| 284 | C(Me)$_2$CH=NOMe | H | 3-F | 2-Me-4-CF(CF$_3$)$_2$ | 199 |
| 285 | C(Me)$_2$CH=NOMe | H | 3-Cl | 2-Me-4-CF(CF$_3$)$_2$ | 234 |
| 286 | C(Me)$_2$CH=NOMe | H | 3-Br | 2-Me-4-CF(CF$_3$)$_2$ | 243 |
| 287 | C(Me)$_2$CH=NOMe | H | 3,4-Cl$_2$ | 2-Me-4-CF(CF$_3$)$_2$ | 207 |
| 288 | C(Me)$_2$CH=NOMe | H | H | 2-Cl-4-CF$_3$ | 154 |
| 289 | C(Me)$_2$CH=NOMe | H | 3-I | 2-Cl-4-CF$_3$ | 167 |
| 290 | C(Me)$_2$CH=NOEt | H | H | 2-Me-4-CF(CF$_3$)$_2$ | 157 |
| 291 | C(Me)$_2$CH=NOEt | H | 3-I | 2-Me-4-CF(CF$_3$)$_2$ | 119 |
| 292 | CH(Me)CH=NOPr-n | H | H | 2-Me-4-CF(CF$_3$)$_2$ | 172 |
| 293 | CH(Me)CH=NOCH$_2$Pr-c | H | H | 2-Me-4-CF$_2$CF$_3$ | 91 |
| 294 | CH(Me)CH=NOCH$_2$CH$_2$SEt | H | H | 2-Me-4-CF$_2$CF$_3$ | paste |
| 295 | CH(Me)CH=NOCH$_2$CH$_2$OEt | H | H | 2-Me-4-CF$_2$CF$_3$ | paste |
| 296 | CH(Me)CH=NOCH$_2$CH=CH$_2$ | H | H | 2-Me-4-CF(CF$_3$)$_2$ | 172 |
| 297 | C(Me)$_2$CH=NOCH$_2$CO$_2$Et | H | 3-I | 2-Me-4-CF$_2$CF$_3$ | |
| 298 | C(Me)$_2$CH=NOCH$_2$CO$_2$Bu-t | H | H | 2-Me-4-OCF$_3$ | 153 |
| 299 | C(Me)$_2$CH=NOCH$_2$CONHEt | H | H | 2-Me-4-CF(CF$_3$)$_2$ | |

TABLE 1-continued

General formula (I)

(Q$^1$ = Q$^2$ = Q$^3$ = Q$^4$ = C—X, Q$^5$ = C, Z$^1$ = Z$^2$ = O, R$^3$ = H)

| No. | —A$^1$—B—R$^1$ | R$^2$ | X | Ym | Physical property |
|---|---|---|---|---|---|
| 300 | C(Me)$_2$CH=NOCH$_2$CONHEt | H | 3-I | 2-Me-4-CF(CF$_3$)$_2$ | |
| 301 | C(Me)$_2$CH=NOCH$_2$CON(Et)$_2$ | H | H | 2-Me-4-CF(CF$_3$)$_2$ | |
| 302 | C(Me)$_2$CH=NOCH$_2$CON(Et)$_2$ | H | H | 2-Me-4-OCF$_3$ | 131 |
| 303 | C(Me)$_2$CH=NOCH$_2$CON(Et)$_2$ | H | 3-I | 2-Me-4-CF(CF$_3$)$_2$ | |
| 304 | (CH$_2$)$_2$CH=NOMe | H | 3-I | 2-Me-4-CF(CF$_3$)$_2$ | 197 |
| 305 | (CH$_2$)$_3$CH=NOMe | H | H | 2-Me-4-OCF$_3$ | 108 |
| 306 | (CH$_2$)$_3$CH=NOEt | H | H | 2-Me-4-OCF$_3$ | 107 |
| 307 | (CH$_2$)$_4$CH=NOMe | H | H | 2-Me-4-OCF$_3$ | 110 |
| 308 | (CH$_2$)$_4$CH=NOEt | H | H | 2-Me-4-OCF$_3$ | 117 |
| 309 | CH(Me)CH$_2$CH=NOMe | H | 3-I | 2-Me-4-CF(CF$_3$)$_2$ | 170 |
| 310 | C(Me)$_2$CH=NOMe | H | 3-I | 2-Me-4-OCF$_2$CHFCF$_3$ | 188 |
| 311 | C(Me)$_2$CH=NOMe | H | H | 2-Me-4-O-(3-Cl-5-CF$_3$-2-Pyr) | 170 |
| 312 | C(Me)$_2$CH=NOMe | H | H | 3-OCF$_2$O-4 | 181 |
| 313 | C(Me)$_2$CH=NOMe | H | H | 3-OCF$_2$CF$_2$O-4 | 191 |
| 314 | CH(Me)CH=NOCH$_2$Pr-c | H | 3-I | 2-Me-4-CF(CF$_3$)$_2$ | 142 |
| 315 | CH(Me)CH=NOCH$_2$CH$_2$SEt | H | 3-I | 2-Me-4-CF(CF$_3$)$_2$ | 165 |
| 316 | CH(Me)CH=NOCH$_2$CH$_2$OEt | H | 3-I | 2-Me-4-CF(CF$_3$)$_2$ | 107 |
| 317 | CH(Me)CH=NOCH$_2$CH=CHOEt | H | 3-I | 2-Me-4-CF(CF$_3$)$_2$ | 103 |
| 318 | C(Me)$_2$CH=NOCH$_2$COOBu-t | H | 3-I | 2-Me-4-CF(CF$_3$)$_2$ | 101 |
| 319 | C(Me)$_2$CH=NOCH$_2$CONEt$_2$ | H | 3-I | 2-Me-4-CF(CF$_3$)$_2$ | 97 |
| 320 | CH(Me)CONHCH$_2$CH$_2$OMe | H | 3-I | 2-Me-4-CF(CF$_3$)$_2$ | 200 |
| 321 | CH(Me)CONHCH$_2$CH$_2$—CH$_2$SMe | H | 3-I | 2-Me-4-CF(CF$_3$)$_2$ | 203 |
| 322 | CH(Me)CONHCH$_2$CF$_3$ | H | 3-I | 2-Me-4-CF(CF$_3$)$_2$ | 236 |

TABLE 2

(Q$^1$=Q$^2$=Q$^3$=Q$^4$=Q$^5$=C, Z$^1$=S, Z$^2$=O, R$^3$=H)

| No. | —A$^1$—B—R$^1$ | R$^2$ | X | Ym | Physical property |
|---|---|---|---|---|---|
| II-1 | CH(Me)CH=NOMe | H | 3-Cl | 2-Me-4-CF(CF$_3$)$_2$ | |
| II-2 | CH(Me)C(Me)=NOMe | H | H | 2-Me-4-CF(CF$_3$)$_2$ | |
| II-3 | CH(Me)CH$_2$CO$_2$Et | H | 3-Cl | 2-Me-4-CF(CF$_3$)$_2$ | |
| II-4 | CH(Me)CON(Et)$_2$ | H | 3-Cl | 2-Me-4-CF(CF$_3$)$_2$ | |
| II-5 | CH(Me)CH$_2$CONHEt | H | 3-Cl | 2-Me-4-CF(CF$_3$)$_2$ | |

TABLE 3

(R$^2$=R$^3$=H, Z$^1$=Z$^2$=O)

| No. | —A$^1$—B—R$^1$ | Q$^1$ | Q$^2$ | Q$^3$ | Q$^4$ | Q$^5$ | Ym | Physical Property |
|---|---|---|---|---|---|---|---|---|
| III-1 | CH(Me)CONHMe | C-I | CH | CH | CH | N | 2-Me-6-OCF(CF$_3$)$_2$ | |
| III-2 | CH(Me)CON(Me)$_2$ | C-I | CH | CH | CH | N | 2-Me-6-OCF(CF$_3$)$_2$ | |
| III-3 | C(Me)$_2$CH=NOH | C-I | CH | CH | CH | N | 2-Me-6-OCF(CF$_3$)$_2$ | 192 |
| III-4 | C(Me)$_2$CH=NOMe | CH | CH | CH | CH | N | 2-Me-6-OCF(CF$_3$)$_2$ | |
| III-5 | C(Me)$_2$CH=NOMe | C-I | CH | CH | CH | N | 2-Me-6-OCF(CF$_3$)$_2$ | 198 |
| III-6 | CH(Me)CONHEt | CH | CH | CH | CH | N | 2-Me-6-OCF(CF$_3$)$_2$ | 220 |

TABLE 3-continued ($R^2=R^3=H$, $Z=Z^2=O$)

| No. | —$A^1$—B—$R^1$ | $Q^1$ | $Q^2$ | $Q^3$ | $Q^4$ | $Q^5$ | Ym | Physical Property |
|---|---|---|---|---|---|---|---|---|
| III-7 | CH(Me)CON(Et)$_2$ | CH | CH | CH | CH | N | 2-Me-6-OCF(CF$_3$)$_2$ | |
| III-8 | CH(Me)C(=O)H | CH | CH | CH | CH | N | 2-Me-6-OCF(CF$_3$)$_2$ | |
| III-9 | CH(Me)CH=NOH | CH | CH | CH | CH | N | 2-Me-6-OCF(CF$_3$)$_2$ | 101 |
| III-10 | CH(Me)CH=NOMe | CH | CH | CH | CH | N | 2-Me-6-OCF(CF$_3$)$_2$ | 105 |
| III-11 | CH(Me)CH=NOMe | C-I | CH | CH | CH | N | 2-Me-6-OCF(CF$_3$)$_2$ | 160 |
| III-12 | CH(Me)CONHEt | CH | CH | CH | CH | N | 2-Me-6-CF(CF$_3$)$_2$ | |
| III-13 | CH(Me)CON(Et)$_2$ | CH | CH | CH | CH | N | 2-Me-6-CF(CF$_3$)$_2$ | |
| III-14 | C(Me)$_2$CH=NOH | CH | CH | CH | CH | N | 2-Me-6-CF(CF$_3$)$_2$ | 208 |
| III-15 | C(Me)$_2$CH=NOMe | CH | CH | CH | CH | N | 2-Me-6-CF(CF$_3$)$_2$ | 162 |
| III-16 | C(Me)$_2$CH=NOMe | C-I | CH | CH | CH | N | 2-Me-6-CF(CF$_3$)$_2$ | |
| III-17 | CH(Me)CONHEt | CH | CH | CH | CH | N | 2-Me-6-CF(CF$_3$)$_2$ | |
| III-18 | CH(Me)CON(Et)$_2$ | CH | CH | CH | CH | N | 2-Me-6-CF(CF$_3$)$_2$ | |
| III-19 | CH(Me)C(=O)H | CH | CH | CH | CH | N | 2-Me-6-CF(CF$_3$)$_2$ | |
| III-20 | CH(Me)CH=NOH | CH | CH | CH | CH | N | 2-Me-6-CF(CF$_3$)$_2$ | |
| III-21 | CH(Me)CH=NOMe | CH | CH | CH | CH | N | 2-Me-6-CF(CF$_3$)$_2$ | |
| III-22 | CH(Me)CH=NOMe | C-I | CH | CH | CH | N | 2-Me-6-CF(CF$_3$)$_2$ | |
| III-23 | CH(Me)CONHEt | N | CH | CH | CH | CH | 2-Me-4-CF(CF$_3$)$_2$ | |
| III-24 | CH(Me)CH=NOMe | N | CH | CH | CH | CH | 2-Me-4-CF(CF$_3$)$_2$ | |
| III-25 | CH(Me)CON(Et)$_2$ | CH | N | CH | CH | CH | 2-Me-4-CF(CF$_3$)$_2$ | |
| III-26 | CH(Me)CH=NOMe | CH | N | CH | CH | CH | 2-Me-4-CF(CF$_3$)$_2$ | 180 |
| III-27 | CH(Me)CONHEt | CH | CH | N | CH | CH | 2-Me-4-CF(CF$_3$)$_2$ | |
| III-28 | CH(Me)CH=NOMe | CH | CH | N | CH | CH | 2-Me-4-CF(CF$_3$)$_2$ | |
| III-29 | CH(Me)CON(Et)$_2$ | CH | CH | CH | N | CH | 2-Me-4-CF(CF$_3$)$_2$ | |
| III-30 | CH(Me)CH=NOMe | CH | CH | CH | N | CH | 2-Me-4-CF(CF$_3$)$_2$ | 153 |
| III-31 | CH(Me)CH=NOMe | N | CH | N | CH | CH | 2-Me-4-CF(CF$_3$)$_2$ | |
| III-32 | CH(Me)CH=NOMe | CH | N | CH | N | CH | 2-Me-4-CF(CF$_3$)$_2$ | |
| III-33 | CH(Me)CON(Et)$_2$ | CH | CH | N | CH | N | 2-Me-6-OCF(CF$_3$)$_2$ | |
| III-34 | CH(Me)CH=NOMe | CH | CH | N | CH | N | 2-Me-6-OCF(CF$_3$)$_2$ | |
| III-35 | CH(Me)CON(Et)$_2$ | CH | CH | N | CH | N | 2-Me-6-CF(CF$_3$)$_2$ | |
| III-36 | CH(Me)CH=NOMe$_2$ | CH | CH | N | CH | N | 2-Me-6-CF(CF$_3$)$_2$ | |

Note:
In the Table 3, when $Q^5$ represents nitrogen atom, then said nitrogen atom is 1-position and the substituted position of Ym is determined thereby.

The agrohorticultural composition, particularly, agrohorticultural insecticides containing the aromatic diamide derivative represented by the formula (I) or salt thereof of the present invention as an active ingredient are suitable for controlling various insect pests such as agrohorticultural insect pests, stored grain insect pests, sanitary insect pests, nematodes, etc., which are injurious to paddy rice, fruit trees, vegetables, other crops, flowers, ornamental plants, etc. They have a marked insecticidal effect, for example, on LEPIDOPTERA including summer fruit tortrix (*Adoxophes orana fasciata*), smaller tea tortrix (*Adoxophyes sp.*), Manchurian fruit moth (*Grapholita inopinata*), oriental fruit moth (*Grapholita molesta*), soybean pod border (*Leguminovora glycinivorella*), mulberry leafroller (*Olethreutes mori*), tea leafroller (*Caloptilia thevivnra*), *Caloptilia sp.*(*Caloptilia zachrysa*), apple leafminer (*Phyllonorycter ringoniella*), pear barkminer (*Spulerrina astaurota*), common white (*Piers rapae crucivora*), tobacco budworm (*Heliothis sp.*), codling moth (*Laspey resia pomonella*), diamondback moth (*Plutella xylstella*), apple fruit moth (*Argyresthia conjugella*), peach fruit moth (*Carposina niponensis*), rice stem borer (*Chilo suppressalis*), rice leafroller (*Cnaphalocrocis medinalis*) tobacco moth (*Ephestia elutella*), mulberry pyralid (*Glyphodes pyloalis*), yellow rice borer (*Scirpophaga incertula*), rice skipper (*Parnara guttata*), rice armyworm (*Pseudaletia separata*), pink borer (*Sesamia inferens*), common cutworm (*Spodoptera litura*), beet armyworm (*Spodoptera exigua*), etc.; HEMIPTERA including aster leafhopper (*Macrosteles fascifrons*), green rice leafhopper (*Nephotettix cinctlcepts*), brown rice planthopper (*Nilaparvata lugens*), whitebacked rice planthopper (*Sogatella furcifera*), citrus psylla (*Diaphorina citri*), grape whitefly (*Aleurolitbus tanha*), sweetpotato whitefly (*Bemisia tahaci*), greenhouse whitefly (*Trialeurodes vaporariortum*), turnup aphid (*Lipaphis erysimi*), green peach aphid (*Myzus persicae*), Indian wax scale (*Ceroplastes ceriferus*), cottony citrus scale (*Pulvinarid aurantii*), camphor scale (*Pseudaonidia duplex*), san Jose scale (*Comstockaspis perniciosa*), arrowhead scale (*Unapsis yanonensis*), etc.; TYLENCHIDA including soybean beetle (*Anomala rufocuprea*), Japanese beetle (*Popillia japonica*), tobacco beetle (*Lasioderma serricorne*), powderpost beetle (*Lyctus brunneus*), twenty-eight-spotted ladybird (*Epilachna vigintiotopunctata*), azuki bean weevil (*Callosohruchus chinensis*) vegetable weevil (*Listroderes costirostris*), maize weevil (*Sitophilus zeamais*), boll weevil (*Anthonomus gradis gradis*), rice water weevil (*Lissorhoptrus oryzophilus*), cucurbit leaf beetle (*Aulacophora femoralis*), rice leaf beetle (*Oulema oryzae*), striped flea beetle (*Phyllotreta striolata*), pine shoot beetle (*Tomicus piniperda*), Colorado potato beetle (*Leptinotarsa decemlineata*), Mexican bean beetle (*Epilachna varivestis*), corn rootworm (*Diabrotica sp.*), etc.; DIPTERA including (*Dacus*(*Zeugodacus*)*cticirbitae*), oriental fruit fly (*Dacus*(*Bactrocera*)*dorsalis*), rice leafminer (*Agnomyza oryzae*), onion maggot (*Delia antiquia*), seedcorn maggot (*Delia platura*), soybean pod gall midge (*Asphondylia sp.*), muscid fly (*Musca domestica*), house mosquito (*Culex pipiens pipiens*), etc.; and TYLENCHIDA including root-lesion nematode (*Pratylenchus sp.*), coffee root-lesion nematode (*Pratylenchus coffeae*), potato cyst nematode (*Globodera rostochiensis*), root-knot nematode (*Meloidogyne sp.*), citrus nematode (*Tylenchulus semipenetrans*), *Aphelenchus sp.* (*Aphelenchus avenae*), chrysanthemum foliar (*Aphelenchoides ritzemabosi*), etc.

The agrohorticultural composition, particularly, agrohorticultural insecticides containing the aromatic diamide derivative represented by formula (I) or salt thereof of the present invention has a marked controlling effect on the above-exemplified insect pests, sanitary pests and/or nematodes, which are injurious to paddy field crops, upland crops, fruit trees, vegetables and other crops, flowers and ornament plants, and the like. Therefore, the desired effect of the agrohorticultural insecticide of the present invention can be exhibited by applying the insecticide to the paddy field water, stalks and leaves or soil of paddy field, upland field, fruit trees, vegetables, other crops or flowers and ornament plants at a season at which the insect pests, sanitary pests or nematodes are expected to appear, before their appearance or at the time when their appearance is confirmed.

In general, the agrohorticultural composition of the present invention is used after being prepared into conveniently usable forms according to ordinary manner for preparation of agrochemicals.

That is, the aromatic diamide derivative of formula (I) or salt thereof and an appropriate carrier are blended optionally together with an adjuvant in a proper proportion and prepared into a suitable preparation form such as suspension, emulsifiable concentrate, soluble concentrate, wettable powder, granules, dust or tablets through dissolution, separation, suspension, mixing, impregnation, adsorption or sticking.

The inert carrier used in the present invention may be either solid or liquid. As the solid carrier, soybean flour, cereal flour, wood flour, bark flour, saw dust, powdered tobacco stalks, powdered walnut shells, bran, powdered cellulose, extraction residues of vegetables, powdered synthetic polymers or resins, clay (e.g. kaolin, bentonite and acid clay), talc (e.g. talc and pyrophyllite), silica materials (e.g. diatomaceous earth, siliceous sand, mica, white carbon, i.e. synthetic high-dispersion silicic acid, also called finely divided hydrated silica or hydrated silicic acid, some of the commercially available products contain calcium silicate as the major component), activated carbon, powdered sulfur, pumice, calcined diatomaceous earth, ground brick, fly ash, sand, calcium carbonate, calcium phosphate and other inorganic or mineral powders, chemical fertilizers such as ammonium sulfate, ammonium phosphate, ammonium nitrate, urea, ammonium chloride and the like, and compost. These carriers may be used either alone or as a mixture of two or more carriers.

The liquid carrier is that which itself has a solubility or which is without such solubility but is capable of dispersing an active ingredient with the aid of an adjuvant. The following are typical examples of the liquid carrier and can be used alone or as a mixture thereof. Water; alcohols such as methanol, ethanol, isopropanol, butanol and ethylene glycol; ketones such as acetone, methyl ethyl ketone, methyl isobutyl ketone, diisobutyl ketone and cyclohexanone; ethers such as ethyl ether, dioxane, cellosolve, dipropyl ether and tetrahydrofuran; aliphatic hydrocarbons such as kerosene and mineral oil; aromatic hydrocarbons such as benzene, toluene, xylene, solvent naphtha and alkylnaphthalene; halogenated hydrocarbons such as dichlorethane, chloroform, carbon tetrachloride and chlorobenzene; esters such as ethyl acetate, diisopropyl phthalate, dibutyl phthalate and dioctyl phthalate; amides such as dimethylformamide, diethylformamide and dimethylacetamide; nitrites such as acetonitrile; and dimethyl sulfoxide.

The following are typical examples of the adjuvant, which are used depending upon purposes and used alone or in combination of two or more adjuvants in some cases, or need not to be used at all.

To emulsify, disperse, dissolve and/or wet an active ingredient, a surfactant is used. As the surfactant, there can be exemplified polyoxyethylene alkyl ethers, polyoxyethylene alkylaryl ethers, polyoxyethylene higher fatty acid esters, polyoxyethylene resinates, polyoxyethylene sorbitan monolaurate, polyoxyethylene sorbitan monooleate, alkylarylsulfonates, naphthalene-sulfonic acid condensation products, ligninsulfonates and higher alcohol sulfate esters.

Further, to stabilize the dispersion of an active ingredient, tackify it and/or bind it, there may be used adjuvants such as casein, gelatin, starch, 20, methyl cellulose, carboxymethyl cellulose, gum arabic, polyvinyl alcohols, turpentine, bran oil, bentonite and ligninsulfonates.

To improve the flowability of a solid product, there may be used adjuvants such as waxes, stearates and alkyl phosphates.

Adjuvants such as naphthalenesulfonic acid condensation products and polycondensates of phosphates may be used as a peptizer for dispersible products.

Adjuvants such as silicone oil may also be used as a defoaming agent.

The content of the active ingredient may be varied according to the need. For example, in dusts or granules, the suitable content thereof is from 0.01 to 50% by weight. In emulsifiable concentrate and flowable wettable powder, too, the suitable content is from 0.01 to 50% by weight.

The agrohorticultural composition, particularly agrohorticultural insecticide of the present invention is used to control a variety of insect pests in the following manner. That is, it is applied to a crop on which the insect pests are expected to appear or a site where appearance of the insect pests is undesirable, as it is or after being properly diluted with or suspended in water or the like, in an amount effective for control of the insect pests.

The agrohorticultural composition, particularly the agrohorticultural insecticide of the present invention can also be used to, for example, seeds of plants to be protected from pests, or to cultivation carriers in which the above seeds are to be sown (e.g. sowing soil, nursery mat, water, etc.); and can be used by a method such as application to rice nursery bed, seed dressing, seed disinfection or the like. When applied to pests which verminate in upland crops such as fruit trees, grains, vegetables and the like, it can be used by seed treatments such as dressing, soaking and the like, or by drenching or surface spraying/watering to, for example, seedling-raising carriers such as cultivation vessel, planting hole and the like to allow the crops to absorb the present insecticide, or by application to water culture solution for water culture.

The applying dosage of the agrohorticultural composition of the present invention is varied depending upon various factors such as a purpose, insect pests to be controlled, a growth state of a plant, tendency of insect pests appearance, weather, environmental conditions, a preparation form, an application method, an application site and an application time. It may be properly chosen in a range of 0.1 g to 10 kg (in terms of active ingredient compound) per 10 ares depending upon purposes.

The agrohorticultural composition of the present invention may be used in admixture with other agricultural and horticultural disease or pest controllers in order to expand both spectrum of controllable diseases and insect pest species and the period of time when effective applications are possible or to reduce the dosage.

Next, typical examples and test examples of the invention are presented below. The present invention is by no means limited by these examples.

EXAMPLES

Representative examples of the present invention are shown below. However, the present invention is not restricted to these examples.

Example 1

(1-1) Production of 3-iodo-1-N-(4-heptafluoro-isopropyl-2-methylphenyl)-phthalamic acid A solution of 3.5 g of 4-heptafluoro-isopropyl-2-methylaniline dissolved in 3 ml of acetonitrile was dropwise added slowly to a suspension of 3.5 g of 3-iodophthalic anhydride suspended in 30 ml of acetonitrile, with ice-cooling. After the completion of the dropwise addition, a reaction was conducted for 3 hours at room temperature, with stirring. After the completion of the reaction, the precipitated crystals were collected by filtration and washed with a small amount of acetonitrile to obtain 4.0 g of an intended compound.

Physical property: melting point=174–181° C.
Yield: 57%

(1-2) Production of 3-iodo-N-(4-heptafluoroisopropyl-2-methylphenyl)phthalisoimide 1.1 g of trifluoroacetic anhydride was added to a suspension of 2.0 g of 3-iodo-1-N-(4-hepta-fluoroisopropyl-2-methylphenyl)-phthalamic acid suspended in 10 ml of toluene. A reaction was conducted at room temperature for 30 minutes, with stirring. After the completion of the reaction, the solvent was removed by vacuum distillation to obtain 2.0 g of a crude intended compound. The compound was used in the next reaction without being purified.

$^1$H-NMR [CDCl$_3$/TMS, δ(ppm)]
2.4 (3H,s), 7.3 (1H,d), 7.4 (2H,m), 7.5 (1H,t), 8.1 (1H,d), 8.2 (1H,d)

(1-3) Production of 3-iodo-N$^1$-(4-heptafluoroisopropyl-2-methylphenyl)-N$^2$-[1-methyl-2-(N,N-dimethylcarbamoyl)-ethyl]phthalamide (compound No. 77)

1.0 g of 3-iodo-N-(4-heptafluoroisopropyl-2-methylphenyl) phthalisoimide was dissolved in 10 ml of acetonitrile. To the resulting solution were added 0.35 g of 3-amino-N,N-dimethylbutyramide hydrochloride and 0.21 g of triethylamine. The resulting mixture was stirred at room temperature for 10 hours to give rise to a reaction. After the completion of the reaction, the reaction mixture was poured into ice water, followed by extraction with ethyl acetate. The organic layer was washed with an aqueous sodium chloride solution and then dried over anhydrous magnesium sulfate. The solvent was removed by vacuum distillation, and the resulting residue was purified by silica gel column chromatography to obtain 0.4 g of an intended product.

Physical property: melting point=126° C.
Yield: 32%

Example 2

Production of 3-iodo-N$^1$-(4-heptafluoro-isopropyl-2-methylphenyl)-N$^2$-[1-methyl-2-(methoxyimino)-ethyl]phthalamide (compound No. 136)

0.9 g of 3-iodo-N-(4-heptafluoroisopropyl-2-methylphenyl)phthalisoimide was dissolved in 10 ml of acetonitrile. To the resulting solution were added 0.34 g of 1-methyl-2-(methoxyimino)ethylamine hydrochloride and 0.25 g of triethylamine. The resulting mixture was stirred at room temperature for 10 hours to give rise to a reaction. After the completion of the reaction, the reaction mixture was poured into ice water, followed by extraction with ethyl acetate. The organic layer was washed with an aqueous sodium chloride solution and then dried over anhydrous magnesium sulfate. The solvent was removed by vacuum distillation, and the resulting residue was purified by silica gel column chromatography to obtain 0.36 g of an intended product.

Physical property: melting point=192° C.
Yield: 36%

Example 3

(3-1) Production of 3-iodo-2-N-[1-methyl-2-(ethoxycarbonyl)ethyl]-phthalamic acid A solution of 1.4 g of ethyl 3-aminobutyrate dissolved in 3 ml of acetonitrile was dropwise added slowly to a suspension of 2.7 g of 3-iodophthalic anhydride suspended in 30 ml of acetonitrile, with ice-cooling. After the completion of the dropwise addition, a reaction was conducted for 3 hours at room temperature, with stirring. After the completion of the reaction, the precipitated crystals were collected by filtration and washed with a small amount of acetonitrile to obtain 3.8 g of an intended compound.

Yield: 97%

(3-2) Production of 6-iodo-N-[1-methyl-2-(ethoxycarbonyl)ethyl]phthalisoimide 1.1 g of trifluoroacetic anhydride was added to a suspension of 1.0 g of 3-iodo-2-N-[1-methyl-2-(ethoxycarbonyl)ethyl]phthalamic acid suspended in 10 ml of toluene. A reaction was conducted at room temperature for 30 minutes, with stirring. After the completion of the reaction, the solvent was removed by vacuum distillation to obtain 0.9 g of a crude intended compound. The compound was used in the next reaction without being purified.

(3-3) Production of 3-iodo-N'-(4-heptafluoroisopropyl-2-methylphenyl)-N-2-[1-methyl-2-(ethoxycarbonyl)-ethyl] phthalamide (compound No. 11)

0.90 g of 6-iodo-N-[1-methyl-2-(ethoxycarbonyl)ethyl] phthalisoimide was dissolved in 10 ml of acetonitrile. To the resulting solution were added 0.5 g of 4-heptafluoroisopropyl-2-methylaniline and two drops of trifluoroacetic acid. The resulting mixture was stirred at room temperature for 10 hours to give rise to a reaction. After the completion of the reaction, the reaction mixture was poured into ice water, followed by extraction with ethyl acetate. The organic layer was washed with an aqueous sodium chloride solution and then dried over anhydrous magnesium sulfate. The solvent was removed by vacuum distillation, and the resulting residue was purified by silica gel column chromatography to obtain 0.50 g of an intended product.

Physical property: paste-like
Yield: 31%
$^1$H-NMR [CDCl$_3$/TMS, δ(ppm)]
1.1–1.4 (5H,m), 2.4 (3H,s), 2.5–2.6 (2H,m), 4.1 (2H,q), 4.4–4.5 (1H,m), 6.8 (1H,d), 7.2 (1H,t), 7.4–7.5 (2H,m), 7.8 (1H,d), 7.9 (1H,d), 8.3 (1H,d), 8.5 (1H,s)

Example 4

Production of 3-iodo-N$^1$-(4-heptafluoro-isopropyl-2-methylphenyl)-N$^2$-(3-oxobutan-2-yl)-phthalamide (compound No. 134)

1.5 g of 3-iodo-N-(4-heptafluoroisopropyl-2-methylphenyl)phthalisoimide was dissolved in 10 ml of acetonitrile. To the resulting solution were added 0.35 g of 3-aminobutanone hydrochloride and 0.29 g of triethylamine. The resulting mixture was stirred at room temperature for 10 hours to give rise to a reaction. After the completion of the reaction, the reaction mixture was poured into ice water, followed by extraction with ethyl acetate. The organic layer was washed with an aqueous sodium chloride solution and then dried over anhydrous magnesium sulfate. The solvent was removed by vacuum distillation, and the resulting residue was purified by silica gel column chromatography to obtain 0.70 g of an intended product.

Physical property: melting point=189° C.

Yield: 41%

Next, typical formulation examples and test examples of the invention are presented below. The present invention is by no means limited by these examples.

In the formulation examples, the term "parts" means "parts by weight".

Formulation Example 1

| | |
|---|---|
| Each compound listed in Tables 1 to 3 | 50 parts |
| Xylene | 40 parts |
| Mixture of polyoxyethylene nonylphenyl ether and calcium alkylbenzenesulfonate | 10 parts |

An emulsifiable concentrate was prepared by mixing uniformly the above ingredients to effect dissolution.

Formulation Example 2

| | |
|---|---|
| Each compound listed in Tables 1 to 3 | 3 parts |
| Clay powder | 82 parts |
| Diatomaceous earth powder | 15 parts |

A dust was prepared by mixing uniformly and grinding the above ingredients.

Formulation Example 3

| | |
|---|---|
| Each compound listed in Tables 1 to 3 | 5 parts |
| Mixed powder of bentonite and clay | 90 parts |
| Calcium ligninsulfonate | 5 parts |

Granules were prepared by mixing the above ingredients uniformly, and kneading the resulting mixture together with a suitable amount of water, followed by granulation and drying.

Formulation Example 4

| | |
|---|---|
| Each compound listed in Tables 1 to 3 | 20 parts |
| Mixture of kaolin and synthetic high-dispersion silicic acid | 75 parts |
| Mixture of polyoxyethylene nonylphenyl ether and calcium alkylbenzenesulfonate | 5 parts |

A wettable powder was prepared by mixing uniformly and grinding the above ingredients.

Formulation Example 5

| | |
|---|---|
| Each compound listed in Tables 1 to 3 | 20 parts |
| Sodium alkylnapthalenesulfonate | 3 parts |
| Propylene glycol | 5 parts |
| Dimethylpolysiloxane | 0.25 part |
| p-Chloro-m-xylenol | 0.10 part |
| Xanthan gum | 0.30 part |
| Water | 71.35 part |

A wettable powder or wettable suspension was prepared by mixing uniformly and wet-grinding the above ingredients.

Test Example 1

Insecticidal Effect on Diamond Back Moth (*Pluitepla xylostellg*)

Adult diamond back moths were released and allowed to oviposit on a Chinese cabbage seedling. Two days after the release, the seedling having the eggs deposited thereon was immersed for about 30 seconds in a liquid chemical prepared by diluting a preparation containing each compound listed in Tables 1 to 3 as an active ingredient to adjust the concentration to 50 ppm. After air-dryness, it was allowed to stand in a room thermostatted at 25° C. Six days after the immersion, the hatched insects were counted. The mortality was calculated according to the following equation and the insecticidal effect was judged according to the criterion shown below. The test was carried out with triplicate groups of 10 insects.

$$\text{Corrected mortality}(\%) = \frac{\text{Number of hatched insects in untreated group} - \text{Number of hatched insects in treated group}}{\text{Number of hatched insects in untreated group}} \times 100.$$

Criterion:

A—Mortality 100%

B—Mortality 99–90%

C—Mortality 89–80%

D—Mortality 79–50%

Test Example 2

Insecticidal Effect on Common Cutworm (*Spodoptera litura*)

A piece of cabbage leaf (cultivar; Shikidori) was immersed for about 30 seconds in a liquid chemical prepared by diluting a preparation containing each compound listed in Tables 1 to 3 as an active ingredient to adjust the concentration to 500 ppm. After air-dryness, it was placed in a plastic Petri dish with a diameter of 9 cm and inoculated with second-instar larvae of common cutworm, after which the dish was closed and then allowed to stand in a room thermostatted at 25° C. Eight days after the inoculation, the dead and alive were counted. The mortality was calculated according to the following equation and the insecticidal effect was judged according to the criterion shown in Test Example 1. The test was carried out with triplicate groups of 10 insects.

$$\text{Corrected mortality}(\%) = \frac{\text{Number of alive larvae in untreated group} - \text{Number of alive larvae in treated group}}{\text{Number of alive larvae in untreated group}} \times 100$$

Test Example 3

Insecticidal Effect on Smaller Tea Tortrix (*Adxophyes sp.*)

Tea leaves were immersed for about 30 seconds in a liquid chemical prepared by diluting a preparation containing each compound listed in Tables 1 to 3 as an active ingredient to adjust the concentration to 50 ppm. After air-dryness, the tea leaves were placed in a plastic Petri dish with a diameter of 9 cm and inoculated with larvae of smaller tea tortrix, after which the dish was allowed to stand in a room thermostatted at 259 and having a humidity of 70%. Eight days after the inoculation, the dead and alive were counted and the insecticidal effect was judged according to the criterion shown in Test Example 1. The test was carried out with triplicate groups of 10 insects.

In the test mentioned above, the compounds which exhibited an activity ranking B or higher against diamond back moth (*Pluitella xyvlstplla*) were as follows:
2~11, 70~78, 134, 136~141, 177, 204, 205, 207, 215~219, 226, 229, 230~237, 239, 241~296, 298, 302, 304, 306, 309, III-3, III-5, III-91~II-11, III-14, III-15, III-26 and III-30.

Further, the compounds which exhibited an activity ranking B or higher against Common cutworm (*Spodoptera litura*) were as follows:
11, 71~74, 77, 78, 136~140, 204, 205, 207, 216, 226, 246, 248, 256, 258, 260, 263, 265, 272, 275, 277~279, 284~286, 291, 292, 309, III-3, III-5 and III-11.

Furthermore, the compounds which exhibited an activity ranking B or higher against smaller tea tortrix (*Adxophyes sp.*) were as follows:
7, 11, 70~72, 74~78, 134, 136~140, 204, 205, 207, 216, 218, 219, 226, 246~250, 253, 254, 256, 258, 259, 263, 265, 266, 271~273, 275~279, 281, 283, 285, 286, 290, 291, 296, 298, 304, 309, III-3, III-5, III-10, III-11, III-15 and III-26.

What is claimed is:
1. An aromatic diamide compound represented by the following general formula (I) or a salt thereof:

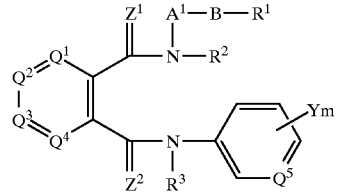

{wherein $A^1$ is a $(C_1-C_8)$alkylene group; a substituted $(C_1-C_8)$ alkylene group having one or more same or different substituents selected from halogen atoms, cyano group, nitro group, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_5)$alkylsulfonyl groups, $(C_1-C_6)$alkylthio$(C_1-C_6)$alkyl groups, $(C_1-C_6)$-alkoxycarbonyl groups and phenyl group; a $(C_3-C_8)$-alkenylene group; a substituted $(C_3-C_8)$alkenylene group having one or more same or different subsbtuents selected from halogen atoms, cyano group, nitro group, halo$(C_1-C_8)$ alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$ alkylsulfinyl groups, $(C_1-C_6)$alkylsulfonyl groups, halo $(C_1-C_6)$alkylsulfonyl groups, $(C_1-C_6)$-alkylthio$(C_1-C_6)$ alkyl groups, $(C_1-C_6)$alkoxycarbonyl groups and phenyl group; a $(C_3-C_8)$alkynylene group; or a substituted $(C_3-C_8)$ alkynylene group having one or more same or different substituents selected from halogen atoms, cyano group, nitro group, halo$(C_1-C_6)$alkyl groups, $(C_1-C_6)$alkoxy groups, halo$(C_1-C_6)$alkoxy groups, $(C_1-C_6)$-alkylthio groups, halo($C_1-C_6)$alkylthio groups, $(C_1-C_6)$alkylsulfinyl groups, halo $(C_1-C_6)$alkylsulfinyl groups, $(C_1-C_6)$alkylsulfonyl groups, halo$(C_1-C_6)$alkylsulfonyl groups, $(C_1-C_6)$alkylthio$(C_1-C_6)$ alkyl groups, $(C_1-C_6)$alkoxycarbonyl groups and phenyl group;

in the $(C_1-C_8)$alkylene group, the substituted $(C_1-C_8)$ alkylene group, the $(C_3-C_8)$alkenylene group, the substituted $(C_3-C_8)$ alkenylene group, the $(C_3-C_8)$- alkynylene group or the substituted $(C_3-C_8)$alkynylene group, any saturated carbon atom may be substituted with a $(C_2-C_5)$alkylene group to form a $(C_3-C_6)$ cycloalkane ring; further in the $(C_1-C_6)$alkylene group, the substituted $(C_1-C_8)$ alkylene group, the $(C_3-C_8)$ alkenylene group or the substituted $(C_3-C_8)$ alkenylene group, any two carbon atoms may be combined with an alkylene group or an alkenylene group to form a $(C_3-C_6)$cycloalkane ring or a $(C_3-C_6)$cycloalkene ring;

B is —C(=N—OR$^4$)— (wherein R$^4$ is a hydrogen atom; a $(C_1-C_6)$alkyl group; a halo$(C_1-C_6)$alkyl group; a $(C_3-C_6)$alkenyl group; a halo$(C_3-C_6)$alkenyl group; a $(C_3-C_6)$alkynyl group; a $(C_3-C_6)$cycloalkyl group; a phenyl$(C_1-C_4)$alkyl group; or a substituted phenyl $(C_1-C_4)$alkyl group having, on the ring, one or more same or different substituents selected from halogen atoms, cyano group, nitro group, $(C_1-C_6)$alkyl groups, halo$(C_1-C_6)$alkyl groups, $(C_1-C_6)$alkoxy groups, halo $(C_1-C_6)$alkoxy groups, $(C_1-C_6)$alkylthio groups, halo $(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono $(C_1-C_6)$alkylamino groups, di$(C_1-C_6)$alkylamino groups wherein the two alkyl groups may be the same or different, and $(C_1-C_6)$-alkoxycarbonyl groups);

R$^1$ is a hydrogen atom; a $(C_1-C_6)$alkyl group; a halo $(C_1-C_6)$alkyl group; a $(C_2-C_6)$alkenyl group; a halo $(C_2-C_6)$alkenyl group; a $(C_3-C_6)$cycloalkyl group; a halo$(C_3-C_6)$cycloalkyl group; a $(C_1-C_6)$alkoxy group; a halo$(C_1-C_6)$alkoxy group; a $(C_1-C_6)$alkylthio group; a halo$(C_1-C_6)$alkylthio group; a mono$(C_1-C_6)$ alkylamino group; a di$(C_1-C_6)$alkylamino group wherein the two alkyl groups may be the same or different; a phenyl group; a substituted phenyl group having one or more same or different substituents selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$ alkylsulfonyl groups, mono$(C_1-C_6)$alkylamino groups, di$(C_1-C_6)$alkylamino groups wherein the two alkyl groups may be the same or different, and $(C_1-C_6)$ alkoxycarbonyl groups; a phenylamino group; a substituted phenylamino group having, on the ring, one or more same or different substituents selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups wherein the two alkyl groups may be the same or different, and $(C_1-C_6)$alkoxycarbonyl groups; a phenyloxy group; a substituted phenyloxy group having one or more same or different substituents selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups wherein the two alkyl groups may be the same or different, and $(C_1-C_6)$-alkoxycarbonyl groups; a phenylthio group; a substituted phenylthio group having one or more same or different substituents selected from halogen atoms, cyano group, nitro group, $(C_1-C_6)$ alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$ alkylsulfinyl groups, halo$(C_1-C_6)$alkylsulfinyl groups, $(C_1-C_6)$alkylsulfonyl groups, halo$(C_1-C_6)$ alkylsulfonyl groups, mono$(C_1-C_6)$alkylamino groups, di$(C_1-C_6)$alkylamino groups wherein the two alkyl groups may be the same or different, and $(C_1-C_6)$-alkoxycarbonyl groups; a heterocyclic group; or a substituted heterocyclic group having one or more same or different substituents selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups wherein the two alkyl groups may be the same or different, and $(C_1-C_6)$alkoxycarbonyl groups;

$R^1$ may bond with $A^1$ to form a 4- to 7-membered ring which may contain, as a ring-constituting atom(s), one or two same or different atoms selected from oxygen, sulfur and nitrogen atoms;

$R^2$ and $R^3$ may be the same or different and are each a hydrogen atom, a $(C_3-C_6)$cycloalkyl group or —$A^2$— $R^5$ [wherein $A^2$ is —C(=O)—, —C(=S)—, —C(=NR$^6$)— (wherein $R^6$ is a hydrogen atom; a $(C_1-C_6)$alkyl group; a $(C_1-C_6)$alkoxy group; a mono$(C_1-C_6)$alkylamino group; a di$(C_1-C_6)$-alkylamino group wherein the two alkyl groups may be the same or different; a $(C_1-C_6)$alkoxycarbonyl group; a phenyl group; or a substituted phenyl group having one or more same or different substituents selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$ alkylsulfinyl groups, halo$(C_1-C_6)$alkylsulfinyl groups, $(C_1-C_6)$alkylsulfonyl groups, halo$(C_1-C_6)$ alkylsulfonyl groups, mono$(C_1-C_6)$alkylamino groups, di$(C_1-C_6)$alkylamino groups wherein the two alkyl groups may be the same or different, and $(C_1-C_6)$ alkoxycarbonyl groups), a $(C_1-C_8)$alkylene group, a halo$(C_1-C_8)$alkylene group, a $(C_3-C_6)$alkenylene group, a halo$(C_3-C_6)$alkenylene group, a $(C_3-C_6)$ alkynylene group or a halo$(C_3-C_6)$alkynylene group;

(1) when $A^2$ is —C(=O)—, —C(=S)— or —C(=NR$^6$)— (wherein $R^6$ has the same definition as given above), $R^5$ is a hydrogen atom; a $(C_1-C_6)$alkyl group; a halo$(C_1-C_6)$-alkyl group; a $(C_1-C_6)$alkoxy group; a $(C_3-C_6)$cycloalkyl group; a halo$(C_3-C_6)$ cycloalkyl group; a phenyl group; a substituted phenyl group having one or more same or different substituents selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$ alkylsulfonyl groups, mono$(C_1-C_6)$alkylamino groups, di$(C_1-C_6)$alkylamino groups wherein the two alkyl groups may be the same or different, and $(C_1-C_6)$-alkoxycarbonyl groups; a heterocyclic group; a substituted heterocyclic group having one or more same or different substituents selected from halogen atoms, cyano group, nitro group, $(C_1-C_6)$alkyl groups, halo $(C_1-C_6)$alkyl groups, $(C_1-C_6)$alkoxy groups, halo $(C_1-C_6)$alkoxy groups, $(C_1-C_6)$alkylthio groups, halo $(C_1-C_6)$alkylthio groups, $(C_1-C_6)$alkylsulfinyl groups, halo$(C_1-C_6)$-alkylsulfinyl groups, $(C_1-C_6)$ alkylsulfonyl groups, halo$(C_1-C_6)$alkylsulfonyl groups, mono$(C_1-C_6)$alkylamino groups, di$(C_1-C_6)$ alkylamino groups wherein the two alkyl groups may be the same or different, and $(C_1-C_6)$-alkoxycarbonyl groups; or —$A^3$—$R^7$ (wherein $A^3$ is —O—, —S— or —N(R$^8$)— (wherein $R^8$ is a hydrogen atom; a $(C_1-C_6)$-alkylcarbonyl group; a halo$(C_1-C_6)$alkylcarbonyl group; a $(C_1-C_6)$alkoxycarbonyl group; a phenylcarbonyl group; a substituted phenylcarbonyl group having one or more same or different substituents selected from halogen atoms, cyano group, nitro group, $(C_1-C_6)$ alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$-alkylthio groups, $(C_1-C_6)$ alkylsulfinyl groups, halo$(C_1-C_6)$alkylsulfinyl groups, $(C_1-C_6)$alkylsulfonyl groups, halo$(C_1-C_6)$ alkylsulfonyl groups, mono$(C_1-C_6)$alkylamino groups, di$(C_1-C_6)$alkylamino groups wherein the two alkyl groups may be the same or different, and $(C_1-C_6)$-alkoxycarbonyl groups; a phenyl$(C_1-C_4)$ alkoxycarbonyl group; or a substituted phenyl$(C_1-C_4)$ alkoxycarbonyl group having, on the ring, one or more same or different substituents selected from halogen atoms, cyano group, nitro group, $(C_1-C_6)$alkyl groups, halo$(C_1-C_6)$alkyl groups, $(C_1-C_6)$alkoxy groups, halo $(C_1-C_5)$alkoxy groups, $(C_1-C_6)$alkylthio groups, halo $(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono $(C_1-C_6)$alkylamino groups, di$(C_1-C_6)$alkylamino groups wherein the two alkyl groups may be the same or different, and $(C_1-C_6)$alkoxycarbonyl groups); and $R^7$ is a $(C_1-C_6)$alkyl group; a halo$(C_1-C_6)$alkyl group; a $(C_3-C_6)$alkenyl group; a halo$(C_3-C_6)$alkenyl group; a $(C_3-C_6)$alkynyl group; a halo$(C_3-C_6)$alkynyl group; a $(C_3-C_6)$cycloalkyl group; a halo$(C_3-C_6)$cycloalkyl group; a $(C_1-C_6)$alkylcarbonyl group; a halo$(C_1-C_6)$ alkylcarbonyl group; a $(C_1-C_6)$-alkoxycarbonyl group; a phenyl group; a substituted phenyl group having one or more same or different substituents selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$ alkylsulfinyl groups, halo$(C_1-C_6)$alkylsulfinyl groups, $(C_1-C_6)$alkylsulfonyl groups, halo$(C_1-C_6)$ alkylsulfonyl groups, mono$(C_1-C_6)$alkylamino groups, di$(C_1-C_6)$alkylamino groups wherein the two alkyl groups may be the same or different, and $(C_1-C_6)$ alkoxycarbonyl groups; a phenyl$(C_1-C_4)$alkyl group; a substituted phenyl$(C_1-C_4)$alkyl group having, on the ring, one or more same or different substituents selected from halogen atoms, cyano group, nitro group, $(C_1-C_6)$ alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$ alkylsulfinyl groups, halo$(C_1-C_6)$alkylsulfinyl groups, $(C_1-C_6)$alkylsulfonyl groups, halo$(C_1-C_6)$ alkylsulfonyl groups, mono$(C_1-C_6)$alkylamino groups, di$(C_1-C_6)$alkylamino groups wherein the two alkyl groups may be the same or different, and $(C_1-C_6)$ alkoxycarbonyl groups; a heterocyclic group; or a substituted heterocyclic group having one or more same or different substituents selected from halogen atoms, cyano group, nitro group, $(C_1-C_6)$alkyl groups, halo$(C_1-C_6)$alkyl groups, $(C_1-C_6)$alkoxy groups, halo $(C_1-C_6)$alkoxy groups, $(C_1-C_6)$alkylthio groups, halo $(C_1-C_6)$alkylthio groups, $(C_1-C_6)$alkylsulfinyl groups, halo$(C_1-C_6)$alkylsulfinyl groups, $(C_1-C_8)$alkylsulfonyl groups, halo$(C_1-C_6)$alkylsulfonyl groups, mono $(C_1-C_6)$alkylamino groups, di$(C_1-C_6)$alkylamino groups wherein the two alkyl groups may be the same or different, and $(C_1-C_6)$alkoxycarbonyl groups);

(2) when $A^2$ is a $(C_1-C_8)$alkylene group, a halo$(C_1-C_8)$ alkylene group, a $(C_3-C_6)$alkenylene group, a halo $(C_3-C_6)$alkenylene group, a $(C_3-C_6)$alkynylene group or a halo$(C_3-C_6)$alkynylene group, $R^5$ is a hydrogen atom; a halogen atom; a cyano group; a nitro group; a $(C_3-C_6)$-Cycloalkyl group; a halo$(C_3-C_6)$cycloalkyl group; a $(C_1-C_6)$alkoxycarbonyl group; a phenyl group; a substituted phenyl group having one or more same or different substituents selected from halogen atoms, cyano group, nitro group, $(C_1-C_6)$alkyl groups, halo$(C_1-C_6)$alkyl groups, $(C_1-C_6)$alkoxy groups, halo $(C_1-C_6)$alkoxy groups, $(C_1-C_6)$alkylthio groups, halo $(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono $(C_1-C_6)$alkylamino groups, di$(C_1-C_6)$alkylamino groups wherein the two alkyl groups may be the same or different, and $(C_1-C_6)$alkoxycarbonyl groups; a heterocyclic group; a substituted heterocyclic group having one or more same or different substituents selected from halogen atoms, cyano group, nitro group, $(C_1-C_6)$ alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$ alkylsulfinyl groups, halo$(C_1-C_6)$alkylsulfinyl groups, $(C_1-C_6)$alkylsulfonyl groups, halo$(C_1-C_6)$ alkylsulfonyl groups, mono$(C_1-C_6)$alkylamino groups, di$(C_1-C_6)$alkylamino groups wherein the two alkyl groups may be the same or different, and $(C_1-C_6)$ alkoxycarbonyl groups; or —$A^4$—$R^9$—(wherein $A^4$ is —O—, —S—, —SO—, —SO$_2$—, —N($R^8$)— ($R^8$ has the same definition as given above), —C(=O)— or —C(=NOR$^4$)— ($R^4$ has the same definition as given above);

(i) when $A^4$ is —O—, —S—, —SO—, —SO$_2$— or —N($R^8$)— ($R^8$ has the same definition as given above), $R^9$ is a hydrogen atom; a $(C_1-C_6)$alkyl group; a halo $(C_1-C_6)$alkyl group; a $(C_3-C_6)$alkenyl group; a halo $(C_3-C_6)$alkenyl group; a $(C_3-C_6)$alkynyl group; a halo $(C_3-C_6)$alkynyl group; a $(C_3C_6)$cycloalkyl group; a halo$(C_3-C_6)$cycloalkyl group; a $(C_1-C_6)$alkylcarbonyl group; a halo$(C_1-C_6)$-alkylcarbonyl group; a $(C_1-C_6)$ alkoxycarbonyl group; a phenyl group; a substituted phenyl group having one or more same or different substituents selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$ alkylsulfinyl groups, $(C_1-C_6)$alkylsulfonyl groups, halo$(C_1-C_6)$alkylsulfonyl groups, mono$(C_1-C_6)$ alkylamino groups, di$(C_1-C_6)$alkylamino groups wherein the two alkyl groups may be the same or different, and $(C_1-C_6)$alkoxycarbonyl groups; a phenyl $(C_1-C_4)$alkyl group; a substituted phenyl$(C_1-C_4)$alkyl group having, on the ring, one or more same or different substituents selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$ alkylsulfinyl groups, $(C_1-C_6)$alkylsulfonyl groups, halo$(C_1-C_6)$alkylsulfonyl groups, mono$(C_1-C_6)$ alkylamino groups, di$(C_1-C_6)$alkylamino groups wherein the two alkyl groups may be the same or different, and $(C_1-C_6)$alkoxycarbonyl groups; a heterocyclic group; or a substituted heterocyclic group having one or more same or different substituents selected from halogen atoms, cyano group, nitro group, $(C_1-C_6)$ alkyl groups, halo$(C_1-C_8)$alkyl groups, $(C_1-C_6)$ alkoxy groups, halo$(C_1-C_6)$alkoxy groups, $(C_1-C_6)$alkylthio groups, halo$(C_1-C_6)$alkylthio groups, $(C_1-C_6)$ alkylsulfinyl groups, halo$(C_1-C_6)$alkylsulfinyl groups, $(C_1-C_6)$-alkylsulfonyl groups, halo$(C_1-C_6)$ alkylsulfonyl groups, mono$(C_1-C_6)$alkylamino groups, di$(C_1-C_6)$alkylamino groups wherein the two alkyl groups may be the same or different, and $(C_1-C_6)$ alkoxycarbonyl groups;

(ii) when $A^4$ is —C(=O)— or —C(=N—OR$^4$)— ($R^4$ has the same definition as given above), $R^9$ is a hydrogen atom; a $(C_1-C_6)$alkyl group; a halo$(C_1-C_6)$ alkyl group; a $(C_2-C_6)$alkenyl group; a halo$(C_2-C_6)$ alkenyl group; a $(C_3-C_6)$cycloalkyl group; a halo $(C_3-C_6)$cycloalkyl group; a $(C_1-C_6)$alkoxy group; a halo$(C_1-C_6)$alkoxy group; a $(C_1-C_6)$alkylthio group; a halo$(C_1-C_6)$alkylthio group; a mono$(C_1-C_6)$ alkylamino group; a di$(C_1-C_6)$alkylamino group wherein the two alkyl groups may be the same or different; a phenyl group; a substituted phenyl group having one or more same or different substituents selected from halogen atoms, cyano group, nitro group, $(C_1-C_6)$alkyl groups, halo$(C_1-C_6)$alkyl groups, $(C_1-C_6)$-alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$ alkylsulfonyl groups, mono$(C_1-C_6)$alkylamino groups, di$(C_1-C_6)$alkylamino groups wherein the two alkyl groups may be the same or different, and $(C_1-C_6)$ alkoxycarbonyl groups; a phenylamino group; a substituted phenylamino group having, on the ring, one or more same or different substituents selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, di$(C_1-C_6)$alkylamino groups wherein the two alkyl groups may be the same or different, and $(C_1-C_6)$ alkoxycarbonyl groups; a phenyloxy group; a substituted phenyloxy group having one or more same or different substituents selected from halogen atoms, cyano group, nitro group, $(C_1-C_6)$alkyl groups, halo $(C_1-C_6)$alkyl groups, $(C_1-C_6)$alkoxy groups, halo $(C_1-C_6)$alkoxy groups, $(C_1-C_6)$alkylthio groups, halo $(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono $(C_1-C_6)$alkylamino groups, di$(C_1-C_6)$alkylamino groups wherein the two alkyl groups may be the same or different, and $(C_1-C_6)$alkoxycarbonyl groups; a phenylthio group; a substituted phenylthio group having, on the ring, one or more same or different substituents selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$ alkylsulfonyl groups, mono$(C_1-C_6)$alkylamino groups, di$(C_1-C_6)$alkylamino groups wherein the two alkyl groups may be the same or different, and $(C_1-C_6)$ alkoxycarbonyl groups; a heterocyclic group; or a substituted heterocyclic group having one or more same or different substituents selected from halogen atoms, cyano group, nitro group, $(C_1-C_6)$alkyl groups, halo$(C_1-C_6)$alkyl groups, $(C_1-C_6)$alkoxy groups, halo $(C_1-C_6)$alkoxy groups, $(C_1-C_6)$alkylthio groups, halo $(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono $(C_1-C_6)$alkylamino groups, di$(C_1-C_6)$alkylamino groups wherein the two alkyl groups may be the same or different, and $(C_1-C_6)$alkoxycarbonyl groups)];

$R^2$ may bond with $A^1$ or $R^1$ to form a 4- to 7-membered ring which may contain, as a ring-constituting atom(s), one or two same or different atoms selected from oxygen, sulfur and nitrogen atoms;

$Q^1$ to $Q^4$ are each a carbon atom which may be substituted with X, and X may be the same or different, and is a halogen atom; a cyano group; a nitro group; a $(C_3-C_6)$ cycloalkyl group; a halo$(C_3-C_6)$cycloalkyl group; a $(C_1-C_6)$alkoxycarbonyl group; a phenyl group; a substituted phenyl group having one or more same or different substituents selected from halogen atoms, cyano group, nitro group, $(C_1-C_6)$alkyl groups, halo $(C_1-C_6)$alkyl groups, $(C_1-C_6)$alkoxy groups, halo $(C_1-C_6)$alkoxy groups, $(C_1-C_6)$alkylthio groups, halo $(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono $(C_1-C_6)$alkylamino groups, di$(C_1-C_6)$alkylamino groups wherein the two alkyl groups may be the same or different, and $(C_1-C_6)$alkoxycarbonyl groups; a heterocyclic group; a substituted heterocyclic group having one or more same or different substituents selected from halogen atoms, cyano group, nitro group, $(C_1-C_6)$ alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$ alkylsulfinyl groups, halo$(C_1-C_6)$-alkylsulfinyl groups, $(C_1-C_6)$alkylsulfonyl groups, halo$(C_1-C_6)$ alkylsulfonyl groups, mono$(C_1-C_6)$alkylamino groups, di$(C_1-C_6)$alkylamino groups wherein the two alkyl groups may be the same or different, and $(C_1-C_6)$- alkoxycarbonyl groups; or —$A^5$—$R^{10}$ [wherein $A^5$ is —O—, —S—, —SO—, —SO$_2$—, —C(=O)—, —C(=NOR$^4$) ($R^4$ has the same definition as given above), a $(C_1-C_6)$alkylene group, a halo$(C_1-C_6)$ alkylene group, a $(C_2-C_6)$alkenylene group, a halo $(C_2-C_6)$alkenylene group, a $C_2-C_6$)alkynylene group or a halo$(C_2-C_6)$alkynylene group;

(1) when $A^5$ is —O—, —S—, —SO— or —SO$_2$—, $R^{10}$ is a halo$(C_3-C_6)$cycloalkyl group; a halo$(C_3-C_6)$ cycloalkenyl group; a phenyl group; a substituted phenyl group having one or more same or different subsbtuents selected from halogen atoms, cyano group, nitro group, $(C_1-C_6)$alkyl groups, halo$(C_1-C_6)$alkyl groups, $(C_1-C_6)$-alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$ alkylsulfinyl groups, $(C_1-C_6)$-alkylsulfonyl groups, halo$(C_1-C_6)$alkylsulfonyl groups, mono$(C_1-C_6)$ alkylamino groups, di$(C_1-C_6)$alkylamino groups wherein the two alkyl groups may be the same or different, and $(C_1-C_6)$alkoxycarbonyl groups; a heterocyclic group; a substituted heterocyclic group having one or more same or different substituents selected from halogen atoms, cyano group, nitro group, $(C_1-C_6)$ alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$ alkylsulfinyl groups, halo$(C_1-C_6)$alkylsulfinyl groups, $(C_1-C_6)$alkylsulfonyl groups, halo$(C_1-C_6)$ alkylsulfonyl groups, mono$(C_1-C_6)$alkylamino groups, di$(C_1-C_6)$alkylamino groups wherein the two alkyl groups may be the same or different, and $(C_1-C_6)$ alkoxycarbonyl groups; or —$A^6$—$R^{11}$ (wherein $A^6$ is a $(C_1-C_6)$alkylene group, a halo$(C_1-C_6)$-alkylene group, a $(C_3-C_6)$alkenylene group, a halo$(C_3-C_6)$-alkenylene group, a $(C_3-C_6)$alkynylene group or a halo$(C_3-C_6)$ alkynylene group, and $R^{11}$ is a hydrogen atom; a halogen atom; a $(C_3-C_6)$cycloalkyl group; a halo $(C_3-C_6)$-cycloalkyl group; a $(C_1-C_6)$alkoxycarbonyl group; a phenyl group; a substituted phenyl group having one or more same or different substituents selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$ alkylsulfonyl groups, mono$(C_1-C_6)$alkylamino groups, di$(C_1-C_6)$alkylamino groups wherein the two alkyl groups may be the same or different, and $(C_1-C_6)$ alkoxycarbonyl groups; or —$A^7$—$R^{12}$ (wherein $A^7$ is —O—, —S—, —SO— or —SO$_2$—, and $R^{12}$ is a $(C_1-C_6)$alkyl group; a halo$(C_1-C_6)$alkyl group; a $(C_3-C_6)$alkenyl group; a halo$(C_3-C_6)$alkenyl group; a $(C_3-C_6)$alkynyl group; a halo$(C_3-C_6)$alkynyl group; a $(C_3-C_6)$cycloalkyl group; a halo$(C_3-C_6)$cycloalkyl group; a phenyl group; a substituted phenyl group having one or more same or different substituents selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$-alkylsulfinyl groups, $(C_1-C_6)$alkylsulfonyl groups, halo$(C_1-C_6)$ alkylsulfonyl groups, mono$(C_1-C_6)$alkylamino groups, di$(C_1-C_6)$alkylamino groups wherein the two alkyl groups may be the same or different, and $(C_1-C_6)$ alkoxycarbonyl groups; a heterocyclic group; or a substituted heterocyclic group having one or more same or different substituents selected from halogen atoms, cyano group, nitro group, $(C_1-C_6)$alkyl groups, halo$(C_1-C_6)$alkyl groups, $(C_1-C_6)$alkoxy groups, halo $(C_1-C_6)$alkoxy groups, $(C_1-C_6)$alkylthio groups, halo $(C_1-C_6)$alkylthio groups, $(C_1-C_6)$alkylsulfinyl groups, halo$(C_1-C_6)$-alkylsulfinyl groups, $(C_1-C_6)$ alkylsulfonyl groups, halo$(C_1-C_6)$alkylsulfonyl groups, mono$(C_1-C_6)$alkylamino groups, di$(C_1-C_6)$ alkylamino groups wherein the two alkyl groups may be the same or different, and $(C_1-C_6)$-alkoxycarbonyl groups));

(2) when $A^5$ is —C(=O)— or —C(=NOR$^4$)— (R$^4$ has the same definition as given above), $R^{10}$ is a $(C_1-C_6)$-alkyl group; a halo$(C_1-C_6)$alkyl group; a $(C_2-C_6)$ alkenyl group; a halo$(C_2-C_6)$alkenyl group; a $(C_3-C_6)$ cycloalkyl group; a halo$(C_3-C_6)$cycloalkyl group; a $(C_1-C_6)$alkoxy group; a $(C_1-C_6)$alkylthio group; a mono$(C_1-C_6)$alkylamino group; a di$(C_1-C_6)$ alkylamino group wherein the two alkyl groups may be the same or different; a phenyl group; a substituted phenyl group having one or more same or different substituents selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$- alkylsulfinyl groups, $(C_1-C_6)$alkylsulfonyl groups, halo$(C_1-C_6)$alkylsulfonyl groups, mono$(C_1-C_6)$ alkylamino groups, di$(C_1-C_6)$alkylamino groups wherein the two alkyl groups may be the same or different, and $(C_1-C_6)$-alkoxycarbonyl groups; a phenylamino group; a substituted phenylamino group having, on the ring, one or more same or different substituents selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$ alkylsulfinyl groups, $(C_1-C_6)$alkylsulfonyl groups, halo$(C_1-C_6)$alkylsulfonyl groups, mono$(C_1-C_6)$- alkylamino groups, di$(C_1-C_6)$alkylamino groups wherein the two alkyl groups may be the same or different, and $(C_1-C_6)$alkoxycarbonyl groups; a heterocyclic group; or a substituted heterocyclic group having one or more same or different substituents selected from halogen atoms, cyano group, nitro group, $(C_1-C_6)$ alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$ alkylsulfinyl groups, halo$(C_1-C_6)$-alkylsulfinyl groups, $(C_1-C_6)$alkylsulfonyl groups, halo$(C_1-C_6)$ alkylsulfonyl groups, mono$(C_1-C_6)$alkylamino groups, di$(C_1-C_6)$alkylamino groups wherein the two alkyl groups may be the same or different, and $(C_1-C_6)$- alkoxycarbonyl groups;

(3) when $A^5$ is a $(C_1-C_6)$alkylene group, a halo$(C_1-C_6)$ alkylene group, a $(C_2-C_6)$alkenylene group, a halo $(C_2-C_6)$alkenylene group, a $(C_2-C_6)$alkynylene group or a halo$(C_2-C_6)$alkynylene group, $R^{10}$ is a hydrogen atom; a halogen atom; a $(C_3-C_6)$cycloalkyl group; a halo$(C_3-C_6)$cycloalkyl group; a $(C_1-C_6)$ alkoxycarbonyl group; a phenyl group; a substituted phenyl group having one or more same or different substituents selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$ alkylsulfinyl groups, $(C_1-C_6)$alkylsulfonyl groups, halo$(C_1-C_6)$alkylsulfonyl groups, mono$(C_1-C_6)$ alkylamino groups, di$(C_1-C_6)$alkylamino groups wherein the two alkyl groups may be the same or different, and $(C_1-C_6)$alkoxycarbonyl groups; a heterocyclic group; a substituted heterocyclic group having one or more same or different substituents selected from halogen atoms, cyano group, nitro group, $(C_1-C_6)$ alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$ alkylsulfinyl groups, halo$(C_1-C_6)$alkylsulfinyl groups, $(C_1-C_6)$alkylsulfonyl groups, halo$(C_1-C_6)$ alkylsulfonyl groups, mono$(C_1-C_6)$alkylamino groups, di$(C_1-C_6)$alkylamino groups wherein the two alkyl groups may be the same or different, and $(C_1-C_6)$ alkoxycarbonyl groups; or —A$^8$—R$^{13}$ (wherein A$^8$ is —O—, —S—, —SO— or —SO$_2$—, and R$^{13}$ is a $(C_3-C_6)$cycloalkyl group; a halo$(C_3-C_6)$cydoalkyl group; a phenyl group; a substituted phenyl group having one or more same or different substituents selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$ alkylsulfonyl groups, mono$(C_1-C_6)$alkylamino groups, di$(C_1-C_6)$alkylamino groups wherein the two alkyl groups may be the same or different, and $(C_1-C_6)$ alkoxycarbonyl groups; a heterocyclic group; a substituted heterocyclic group having one or more same or different substituents selected from halogen atoms, cyano group, nitro group, $(C_1-C_6)$alkyl groups, halo $(C_1-C_6)$alkyl groups, $(C_1-C_6)$alkoxy groups, halo $(C_1-C_6)$alkoxy groups, $(C_1-C_6)$alkylthio groups, halo $(C_1-C_6)$alkylthio groups, $(C_1-C_6)$alkylsulfinyl groups, halo$(C_1-C_6)$-alkylsulfinyl groups, $(C_1-C_6)$ alkylsulfonyl groups, halo$(C_1-C_6)$alkylsulfonyl groups, mono$(C_1-C_6)$alkylamino groups, di$(C_1-C_6)$ alkylamino groups wherein the two alkyl groups may be the same or different, and $(C_1-C_6)$alkoxycarbonyl groups; or —A$^9$—R$^{14}$ (wherein A$^9$ is a $(C_1-C_6)$ alkylene group, a halo$(C_1-C_6)$alkylene group, a $(C_2-C_6)$alkenylene group, a halo$(C_2-C_6)$alkenylene group, a $(C_2-C_6)$alkynylene group or a halo$(C_3-C_5)$ alkynylene group, and R$^{14}$ is a hydrogen atom; a halogen atom; a $(C_3-C_6)$Cycloalkyl group; a halo $(C_3-C_6)$cycloalkyl group; a $(C_1-C_6)$alkoxy group; a halo$(C_1-C_6)$alkoxy group; a $(C_1-C_6)$alkylthio group; a halo$(C_1-C_6)$alkylthio group; a $(C_1-C_6)$alkylsulfinyl group; a halo$(C_1-C_6)$alkylsulfinyl group; a $(C_1-C_6)$alkylsulfonyl group; a halo$(C_1-C_6)$ alkylsulfonyl group; a phenyl group; a substituted phenyl group having one or more same or different substituents selected from halogen atoms, cyano group, nitro group, ($C_1$–$C_6$)alkyl groups, halo($C_1$–$C_6$)alkyl groups, ($C_1$–$C_6$)-alkoxy groups, halo($C_1$–$C_6$)alkoxy groups, ($C_1$–$C_6$) alkylthio groups, halo($C_1$–$C_6$)alkylthio groups, ($C_1$–$C_6$) alkylsulfinyl groups, halo($C_1$–$C_6$)alkylsulfinyl groups, ($C_1$–$C_6$)-alkylsulfonyl groups, halo($C_1$–$C_6$)alkylsulfonyl groups, mono($C_1$–$C_6$)alkylamino groups, di($C_1$–$C_6$) alkylamino groups wherein the two alkyl groups may be the same or different, and ($C_1$–$C_6$)alkoxycarbonyl groups; a phenyloxy group; a substituted phenyloxy group having one or more same or different substituents selected from halogen atoms, cyano group, nitro group, ($C_1$–$C_6$)alkyl groups, halo ($C_1$–$C_6$)alkyl groups, ($C_1$–$C_6$)alkoxy groups, halo($C_1$–$C_5$) alkoxy groups, ($C_1$–$C_6$)alkylthio groups, halo($C_1$–$C_6$) alkylthio groups, ($C_1$–$C_6$)alkylsulfinyl groups, halo($C_1$–$C_6$) alkylsulfinyl groups, ($C_1$–$C_6$)alkylsulfonyl groups, halo ($C_1$–$C_6$)alkylsulfonyl groups, mono($C_1$–$C_6$)-alkylamino groups, di($C_1$–$C_6$)alkylamino groups wherein the two alkyl groups may be the same or different, and ($C_1$–$C_6$) alkoxycarbonyl groups; a phenylthio group; a substituted phenylthio group having one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$) alkylthio groups, halo($C_1$–$C_6$)alkylthio groups, ($C_1$–$C_6$) alkylsulfinyl groups, halo($C_1$–$C_6$)-alkylsulfinyl groups, ($C_1$–$C_6$)alkylsulfonyl groups, halo($C_1$–$C_6$)alkylsulfonyl groups, mono($C_1$–$C_6$)alkylamino groups, di($C_1$–$C_6$) alkylamino groups wherein the two alkyl groups may be the same or different, and ($C_1$–$C_6$)-alkoxycarbonyl groups; a heterocyclic group; or a substituted heterocyclic group having one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo ($C_1$–$C_6$)alkylthio groups, ($C_1$–$C_6$)alkylsulfinyl groups, halo ($C_1$–$C_6$)-alkylsulfinyl groups, ($C_1$–$C_6$)alkylsulfonyl groups, halo($C_1$–$C_6$)alkylsulfonyl groups, mono($C_1$–$C_6$)alkylamino groups, di($C_1$–$C_6$)alkylamino groups wherein the two alkyl groups may be the same or different, and ($C_1$–$C_6$)-alkoxycarbonyl groups)];

the two Xs bonding to the adjacent two carbon atoms constituting the aromatic ring containing $Q^1$ to $Q^4$ may bond to each other to form a condensed ring; the condensed ring may have one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$) alkylsulfinyl groups, ($C_1$–$C_6$)alkylsulfonyl groups, halo($C_1$–$C_6$)-alkylsulfonyl groups, mono($C_1$–$C_6$) alkylamino groups, di($C_1$–$C_6$)alkylamino groups wherein the two alkyl groups may be the same or different, and ($C_1$–$C_6$)alkoxycarbonyl groups;

$Q^5$ is a nitrogen atom or a carbon atom;

Y may be the same or different, and is a halogen atom; a cyano group; a nitro group; a halo($C_3$–$C_6$)cycloalkyl group; a phenyl group; a substituted phenyl group having one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)alkylsulfinyl groups, ($C_1$–$C_6$)alkylsulfonyl groups, halo($C_1$–$C_6$)-alkylsulfonyl groups, mono($C_1$–$C_6$)alkylamino groups, di($C_1$–$C_6$)alkylamino groups wherein the two alkyl groups may be the same or different, and ($C_1$–$C_6$) alkoxycarbonyl groups; a heterocyclic group; a substituted heterocyclic group having one or more same or different substituents selected from halogen atoms, cyano group, nitro group, ($C_1$–$C_6$)alkyl groups, halo ($C_1$–$C_6$)alkyl groups, ($C_1$–$C_6$)alkoxy groups, halo ($C_1$–$C_6$)alkoxy groups, ($C_1$–$C_6$)alkylthio groups, halo ($C_1$–$C_6$)alkylthio groups, ($C_1$–$C_6$)alkylsulfinyl groups, halo($C_1$-Cr)alkylsulfinyl groups, ($C_1$–$C_6$)alkylsulfonyl groups, halo($C_1$–$C_6$)-alkylsulfonyl groups, mono ($C_1$–$C_6$)alkylamino groups, di($C_1$–$C_6$)alkylamino groups wherein the two alkyl groups may be the same or different, and ($C_1$–$C_6$)alkoxycarbonyl groups; or —$A^5$—$R^{10}$ ($A^5$ and $R^{10}$ each have the same definition as given above);

the two Ys bonding to the adjacent two carbon atoms constituting the aromatic ring containing $Q^5$ may bond to each other to form a condensed ring; the condensed ring may have one or more same or different substituents selected from halogen atoms, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$) alkylsulfinyl groups, halo($C_1$–$C_6$)alkylsulfinyl groups, ($C_1$–$C_6$)alkylsulfonyl groups, halo($C_1$–$C_6$) alkylsulfonyl groups, phenyl group, substituted phenyl groups having one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)-alkylsulfinyl groups, ($C_1$–$C_6$)alkylsulfonyl groups, halo($C_1$–$C_6$) alkylsulfonyl groups, mono($C_1$–$C_6$)alkylamino groups, di($C_1$–$C_6$)alkylamino groups wherein the two alkyl groups may be the same or different, and ($C_1$–$C_6$)-alkoxycarbonyl groups, heterocyclic groups, and substituted heterocyclic groups having one or more same or different substituents selected from halogen atoms, cyano group, nitro group, ($C_1$–$C_6$)alkyl groups, halo ($C_1$–$C_6$)alkyl groups, ($C_1$–$C_6$)alkoxy groups, halo ($C_1$–$C_6$)alkoxy groups, ($C_1$–$C_6$)alkylthio groups, halo ($C_1$–$C_6$)alkylthio groups, ($C_1$–$C_6$)alkylsulfinyl groups, halo($C_1$–$C_6$)-alkylsulfinyl groups, ($C_1$–$C_6$) alkylsulfonyl groups, halo($C_1$–$C_6$)alkylsulfonyl groups, mono($C_1$–$C_6$)alkylamino groups, di($C_1$–$C_6$) alkylamino groups wherein the two alkyl groups may be the same or different, and ($C_1$–$C_6$)-alkoxycarbonyl groups;

m is an integer of 0 to 5;

$Z^1$ and $Z^2$ may be the same or different and are each an oxygen atom or a sulfur atom.

2. An aromatic diamide compound or a salt thereof according to claim 1, wherein $A^1$ is a ($C_1$–$C_8$)alkylene group; a substituted ($C_1$–$C_8$) alkylene group having one or more same or different substituents selected from halogen atoms, cyano group, nitro group, halo($C_1$–$C_6$)alkyl groups, ($C_1$–$C_8$)alkoxy groups, halo($C_1$–$C_6$)alkoxy groups, ($C_1$–$C_6$) alkylthio groups, halo($C_1$–$C_6$)alkylthio groups, ($C_1$–$C_6$) alkylsulfinyl groups, halo($C_1$–$C_6$)alkylsulfinyl groups, ($C_1$–$C_6$)alkylsulfonyl groups, halo($C_1$–$C_6$)alkylsulfonyl groups, ($C_1$–$C_5$)alkylthio($C_1$–$C_6$)alkyl groups, ($C_1$–$C_6$) alkoxycarbonyl groups and phenyl group; a ($C_3$–$C_8$) alkenylene group; a substituted ($C_3$–$C_8$)alkenylene group having one or more same or different substituents selected form halogen atoms, cyano group, nitro group, halo($C_1$–$C_6$) alkyl groups, ($C_1$–$C_6$)alkoxy groups, halo($C_1$–$C_6$)alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$-alkylsulfonyl groups, halo$(C_1-C_6)$alkylsulfonyl groups, $(C_1-C_6)$alkylthio$(C_1-C_6)$alkyl groups, $(C_1-C_6)$alkoxycarbonyl groups and phenyl group; a $(C_3-C_8)$alkynylene group; or a substituted $(C_3-C_8)$ alkynylene group having one or more same or different substituents selected form halogen atoms, cyano group, nitro group, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$-alkylsulfonyl groups, $(C_1-C_6)$alkylthio$(C_1-C_6)$alkyl groups, $(C_1-C_6)$alkoxycarbonyl groups and phenyl group;

- in the $(C_1-C_8)$alkylene group, the substituted $(C_1-C_8)$ alkylene group, the $(C_3-C_8)$alkenylene group, the substituted $(C_3-C_8)$alkenylene group, the $(C_3-C_8)$-alkynylene group or the substituted $(C_3-C_8)$alkynylene group, any saturated carbon atom may be substituted with a $(C_2-C_5)$alkylene group to form a $(C_3-C_6)$ cycloalkane ring; further in the $(C_1-C_8)$alkylene group, the substituted $(C_1-C_8)$ alkylene group, the $(C_3-CB)$ alkenylene group or the substituted $(C_3-C_8)$ alkenylene group, any two carbon atoms may be combined with an alkylene group or an alkenylene group to form a $(C_3-C_6)$cycloalkane ring or a $(C_3-C_6)$cycloalkene ring;
- B is —C(=N—OR$^4$)— (wherein R$^4$ is a hydrogen atom; a $(C_1-C_6)$alkyl group; a halo$(C_1-C_6)$alkyl group; a $(C_3-C_6)$alkenyl group; a halo$(C_3-C_6)$alkenyl group; a $(C_3-C_6)$alkynyl group; a $(C_3-C_6)$cycloalkyl group; a phenyl$(C_1-C_4)$alkyl group; or a substituted phenyl $(C_1-C_4)$alkyl group having, on the ring, one or more same or different substituents selected from halogen atoms, cyano group, nitro group, $(C_1-C_6)$alkyl groups, halo$(C_1-C_6)$alkyl groups, $(C_1-C_6)$alkoxy groups, halo $(C_1-C_6)$alkoxy groups, $(C_1-C_6)$alkylthio groups, halo $(C_1-C_6)$alkylthio groups, $(C_1-C_6)$alkylsulfinyl groups, halo$(C_1-C_6)$-alkylsulfinyl groups, $(C_1-C_6)$ alkylsulfonyl groups, halo$(C_1-C_6)$alkylsulfonyl groups, mono$(C_1-C_6)$alkylamino groups, di$(C_1-C_6)$ alkylamino groups wherein the two alkyl groups may be the same or different, and $(C_1-C_6)$alkoxycarbonyl groups);
- R$^1$ is a hydrogen atom; a $(C_1-C_6)$alkyl group; a halo $(C_1-C_6)$alkyl group; a $(C_2-C_6)$alkenyl group; a halo $(C_2-C_6)$alkenyl group; a $(C_3-C_6)$cycloalkyl group; a halo$(C_3-C_6)$cycloalkyl group; a $(C_1-C_6)$alkoxy group; a halo$(C_1-C_6)$alkoxy group; a $(C_1-C_6)$alkylthio group; a halo$(C_1-C_6)$alkylthio group; a mono$(C_1-C_6)$ alkylamino group; a di$(C_1-C_6)$alkylamino group wherein the two alkyl groups may be the same or different; a phenyl group; a substituted phenyl group having one or more same or different substituents selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$-alkylsulfinyl groups, $(C_1-C_6)$alkylsulfonyl groups, halo$(C_1-C_6)$ alkylsulfonyl groups, mono$(C_1-C_6)$alkylamino groups, di$(C_1-C_6)$alkylamino groups wherein the two alkyl groups may be the same or different, and $(C_1-C_6)$-alkoxycarbonyl groups; a phenylamino group; a substituted phenylamino group having, on the ring, one or more same or different substituents selected from halogen atoms, cyano group, nitro group, $(C_1-C_8)$alkyl groups, halo$(C_1-C_6)$alkyl groups, $(C_1-C_6)$alkoxy groups, halo$(C_1-Ce)$alkoxy groups, $(C_1-C_6)$alkylthio groups, halo$(C_1-C_6)$alkylthio groups, $(C_1-C_6)$ alkylsulfinyl groups, halo$(C_1-C_6)$alkylsulfinyl groups, $(C_1-C_6)$alkylsulfonyl groups, halo$(C_1-C_6)$ alkylsulfonyl groups, mono$(C_1-C_6)$-alkylamino groups, di$(C_1-C_6)$alkylamino groups wherein the two alkyl groups may be the same or different, and $(C_1-C_6)$ alkoxycarbonyl groups; a phenyloxy group; a substituted phenyloxy group having one or more same or different substituents selected from halogen atoms, cyano group, nitro group, $(C_1-C_6)$alkyl groups, halo $(C_1-C_6)$alkyl groups, $(C_1-C_6)$alkoxy groups, halo $(C_1-C_6)$alkoxy groups, $(C_1-C_6)$alkylthio groups, halo $(C_1-C_6)$alkylthio groups, $(C_1-C_6)$alkylsulfinyl groups, halo$(C_1-C_6)$-alkylsulfinyl groups, $(C_1-C_6)$ alkylsulfonyl groups, halo$(C_1-C_6)$alkylsulfonyl groups, mono$(C_1-C_6)$alkylamino groups, di$(C_1-C_6)$ alkylamino groups wherein the two alkyl groups may be the same or different, and $(C_1-C_6)$-alkoxycarbonyl groups; a phenylthio group; a substituted phenylthio group having one or more same or different substituents selected from halogen atoms, cyano group, nitro group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$-alkylsulfinyl groups, $(C_1-C_6)$alkylsulfonyl groups, halo$(C_1-C_6)$ alkylsulfonyl groups, mono$(C_1-C_6)$alkylamino groups, di$(C_1-C_6)$alkylamino groups wherein the two alkyl groups may be the same or different, and $(C_1-C_6)$-alkoxycarbonyl groups; a heterocyclic group; or a substituted heterocyclic group having one or more same or different substituents selected from halogen atoms, cyano group, nitro group, $(C_1-C_6)$alkyl groups, halo$(C_1-C_6)$alkyl groups, $(C_1-C_6)$alkoxy groups, halo $(C_1-C_6)$alkoxy groups, $(C_1-C_6)$alkylthio groups, halo $(C_1-C_6)$alkylthio groups, $(C_1-C_6)$alkylsulfinyl groups, halo$(C_1-C_6)$-alkylsulfinyl groups, $(C_1-C_6)$ alkylsulfonyl groups, halo$(C_1-C_6)$alkylsulfonyl groups, mono$(C_1-C_6)$alkylamino groups, di$(C_1-C_6)$ alkylamino groups wherein the two alkyl groups may be the same or different, and $(C_1-C_6)$-alkoxycarbonyl groups;
- R$^1$ may bond with A$^1$ to form a 4- to 7-membered ring which may contain, as a ring-constituting atom(s), one or two same or different atoms selected from oxygen, sulfur and nitrogen atoms;
- R$^2$ and R$^3$ may be the same or different and are each a hydrogen atom or a $(C_1-C_6)$alkyl group;
- Q$^1$ to Q$^4$ are each a carbon atom which may be substituted with X; X may be the same or different, and is a halogen atom, a nitro group, a $(C_1-C_6)$alkyl group, a halo$(C_1-C_6)$alkyl group, a $(C_2C_6)$alkenyl group, a halo $(C_2-C_6)$alkenyl group, a $(C_2C_6)$alkynyl group, a halo $(C_2-C_6)$alkynyl group, a halo$(C_1-C_6)$alkoxy group or a halo$(C_1-C_6)$alkylthio group; the two Xs bonding to the adjacent two carbon atoms constituting the aromatic ring containing Q$^1$ to Q$^4$ may bond to each other to form a condensed ring; the condensed ring may have one or more same or different substituents selected from halogen atoms, $(C_1-C_6)$alkyl groups, halo$(C_1-C_6)$ alkyl groups, $(C_1-C_6)$alkoxy groups, halo$(C_1-C_6)$ alkoxy groups, $(C_1-C_6)$alkylthio groups, halo$(C_1-C_6)$ alkylthio groups, $(C_1-C_6)$alkylsulfinyl groups, halo $(C_1-C_6)$alkylsulfinyl groups, $(C_1-C_6)$alkylsulfonyl groups and halo$(C_1-C_6)$-alkylsulfonyl groups;

$Q^5$ is a nitrogen atom or a carbon atom;

Y may be the same or different when it is more than one, and is a halogen atom; a cyano group; a nitro group; a halo($C_3$–$C_6$)cycloalkyl group; a phenyl group; a substituted phenyl group having one or more same or different substituents selected from halogen atoms, cyano group, nitro group, ($C_1$–$C_6$)alkyl groups, halo ($C_1$–$C_6$)alkyl groups, ($C_1$–$C_6$)alkoxy groups, halo ($C_1$–$C_6$)alkoxy groups, ($C_1$–$C_6$)alkylthio groups, halo ($C_1$–$C_6$)alkylthio groups, ($C_1$–$C_6$)alkylsulfinyl groups, halo($C_1$–$C_6$)alkylsulfinyl groups, ($C_1$–$C_6$)alkylsulfonyl groups, halo($C_1$–$C_6$)alkylsulfonyl groups, mono ($C_1$–$C_6$)-alkylamino groups, di($C_1$–$C_6$)alkylamino groups wherein the two alkyl groups may be the same or different, and ($C_1$–$C_6$)alkoxycarbonyl groups; a heterocyclic group; a substituted heterocyclic group having one or more same or different substituents selected from halogen atoms, cyano group, nitro group, ($C_1$–$C_6$) alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$) alkylsulfinyl groups, halo($C_1$–$C_6$) alkylsulfinyl groups, ($C_1$–$C_6$)alkylsulfonyl groups, halo($C_1$–$C_6$) alkylsulfonyl groups, mono($C_1$–$C_6$)alkylamino groups, di($C_1$–$C_6$)alkylamino groups wherein the two alkyl groups may be the same or different, and ($C_1$–$C_6$)-alkoxycarbonyl groups; or —$A^5$—$R^{10}$ ($A^5$ and $R^{10}$ each have the same definition as given in claim 1);

the two Ys bonding to the adjacent two carbon atoms constituting the aromatic ring containing $Q^5$ may bond to each other to form a condensed ring; the condensed ring may have one or more same or different substituents selected from halogen atoms, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$) alkylsulfinyl groups, halo($C_1$–$C_6$)alkylsulfinyl groups, ($C_1$–$C_6$)alkylsulfonyl groups, halo($C_1$–$C_6$) alkylsulfonyl groups, phenyl group, substituted phenyl groups having one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)-alkylsulfinyl groups, ($C_1$–$C_6$)alkylsulfonyl groups, halo($C_1$–$C_6$) alkylsulfonyl groups, mono($C_1$–$C_6$)alkylamino groups, di($C_1$–$C_6$)alkylamino groups wherein the two alkyl groups may be the same or different, and ($C_1$–$C_6$)-alkoxycarbonyl groups, heterocyclic groups, and substituted heterocyclic groups having one or more same or different substituents selected from halogen atoms, cyano group, nitro group, ($C_1$–$C_6$)alkyl groups, halo ($C_1$–$C_6$)alkyl groups, ($C_1$–$C_6$)alkoxy groups, halo ($C_1$–$C_6$)alkoxy groups, ($C_1$–$C_6$)alkylthio groups, halo ($C_1$–$C_6$)alkylthio groups, ($C_1$–$C_6$)alkylsulfinyl groups, halo($C_1$–$C_6$)-alkylsulfinyl groups, ($C_1$–$C_6$) alkylsulfonyl groups, halo($C_1$–$C_6$)alkylsulfonyl groups, mono($C_1$–$C_6$)alkylamino groups, di($C_1$–$C_6$) alkylamino groups wherein the two alkyl groups may be the same or different, and ($C_1$–$C_6$)-alkoxycarbonyl groups;

m is an integer of 0 to 5;

$Z^1$ and $Z^2$ are each an oxygen atom.

3. An aromatic diamide compound or a salt thereof according to claim 2, wherein $A^1$ is a ($C_1$–$C_8$)-alkylene group; a substituted ($C_1$–$C_8$) alkylene group having one or more same or different substituents selected form halogen atoms, cyano group, nitro group, halo($C_1$–$C_6$)alkyl groups, ($C_1$–$C_6$)alkoxy groups, halo($C_1$-Cr)alkoxy groups, ($C_1$–$C_6$) alkylthio groups, halo($C_1$–$C_6$)alkylthio groups, ($C_1$–$C_6$) alkylsulfinyl groups, halo($C_1$–$C_6$)alkylsulfinyl groups, ($C_1$–$C_6$)alkylsulfonyl groups, halo($C_1$–$C_6$)alkylsulfonyl groups, ($C_1$–$C_6$)-alkylthio($C_1$–$C_6$)alkyl groups, ($C_1$–$C_6$) alkoxycarbonyl groups and phenyl group; a ($C_3$–$C_8$) alkenylene group; a substituted ($C_3$–$C_8$)alkenylene group having one or more same or different substituents selected form halogen atoms, cyano group, nitro group, halo($C_1$–$C_6$) alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_8$)alkylsulfinyl groups, halo($C_1$–$C_6$) alkylsulfinyl groups, ($C_1$–$C_6$)alkylsulfonyl groups, halo ($C_1$–$C_6$)-alkylsulfonyl groups, ($C_1$–$C_6$)alkylthio($C_1$–$C_6$) alkyl groups, ($C_1$–$C_6$)alkoxycarbonyl groups and phenyl group; a ($C_3$–$C_8$)alkynylene group; or a substituted ($C_3$–$C_8$) alkynylene group having one or more same or different substituents selected form halogen atoms, cyano group, nitro group, halo($C_1$–$C_6$)alkyl groups, ($C_1$–$C_6$)alkoxy groups, halo($C_1$–$C_6$)alkoxy groups, ($C_1$–$C_6$)alkylthio groups, halo ($C_1$–$C_6$)alkylthio groups, ($C_1$–$C_6$)alkylsulfinyl groups, halo ($C_1$–$C_6$)alkylsulfinyl groups, ($C_1$–$C_6$)alkylsulfonyl groups, halo($C_1$–$C_6$)alkylsulfonyl groups, ($C_1$–$C_6$)alkylthio($C_1$–$C_6$) alkyl groups, ($C_1$–$C_6$)alkoxycarbonyl groups and phenyl group;

in the ($C_1$–$C_8$)alkylene group, the substituted ($C_1$–$C_8$) alkylene group, the ($C_3$–$C_8$)alkenylene group, the substituted ($C_3$–$C_8$) alkenylene group, the ($C_3$–$C_8$)-alkynylene group or the substituted ($C_3$–$C_8$)alkynylene group, any saturated carbon atom may be substituted with a ($C_2$–$C_5$)alkylene group to form a ($C_3$–$C_6$) cycloalkane ring; further in the ($C_1$–$C_8$)alkylene group, the substituted ($C_1$–$C_8$) alkylene group, the ($C_3$–$C_8$) alkenylene group or the substituted ($C_3$–$C_8$) alkenylene group, any two carbon atoms may be combined with an alkylene group or an alkenylene group to form a ($C_3$–$C_6$)cycloalkane ring or a ($C_3$–$C_6$)cycloalkene ring;

B is —C(=N—$OR^4$)— (wherein $R^4$ is a hydrogen atom; a ($C_1$–$C_6$)alkyl group; a halo($C_1$–$C_6$)alkyl group; a ($C_3$–$C_6$)alkenyl group; a halo($C_3$–$C_6$)alkenyl group; a ($C_3$–$C_6$)alkynyl group; a ($C_3$–$C_6$)cycloalkyl group; a phenyl($C_1$–$C_4$)alkyl group; or a substituted phenyl ($C_1$–$C_4$)alkyl group having, on the ring, one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo ($C_1$–$C_6$)alkoxy groups, ($C_1$–$C_6$)alkylthio groups, halo ($C_1$–$C_6$)alkylthio groups, ($C_1$–$C_6$)alkylsulfinyl groups, halo($C_1$–$C_6$)-alkylsulfinyl groups, ($C_1$–$C_6$) alkylsulfonyl groups, halo($C_1$–$C_6$)alkylsulfonyl groups, mono($C_1$–$C_6$)alkylamino groups, di($C_1$–$C_6$) alkylamino groups wherein the two alkyl groups may be the same or different, and ($C_1$–$C_6$)-alkoxycarbonyl groups);

$R^1$ is a hydrogen atom; a ($C_1$–$C_6$)alkyl group; a halo ($C_1$–$C_6$)alkyl group; a ($C_2$–$C_6$)alkenyl group; a halo ($C_2$–$C_6$)alkenyl group; a ($C_3$–$C_6$)cycloalkyl group; a halo($C_3$–$C_6$)cycloalkyl group; a ($C_1$–$C_6$)alkoxy group; a halo($C_1$–$C_6$)alkoxy group; a ($C_1$–$C_6$)alkylthio group; a halo($C_1$–$C_6$)alkylthio group; a mono($C_1$–$C_6$) alkylamino group; a di($C_1$–$C_6$)alkylamino group wherein the two alkyl groups may be the same or different; a phenyl group; a substituted phenyl group having one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)-alkylsulfinyl groups, ($C_1$–$C_6$)alkylsulfonyl groups, halo($C_1$–$C_6$)

alkylsulfonyl groups, mono($C_1$–$C_6$)alkylamino groups, di($C_1$–$C_6$)alkylamino groups wherein the two alkyl groups may be the same or different, and ($C_1$–$C_6$)-alkoxycarbonyl groups; a phenylamino group; a substituted phenylamino group having, on the ring, one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)alkylsulfinyl groups, ($C_1$–$C_6$)alkylsulfonyl groups, halo($C_1$–$C_6$)alkylsulfonyl groups, mono($C_1$–$C_6$)-alkylamino groups, di($C_1$–$C_6$)alkylamino groups wherein the two alkyl groups may be the same or different, and ($C_1$–$C_6$) alkoxycarbonyl groups; a phenyloxy group; a substituted phenyloxy group having one or more same or different substituents selected from halogen atoms, cyano group, nitro group, ($C_1$–$C_6$)alkyl groups, halo ($C_1$–$C_6$)alkyl groups, ($C_1$–$C_6$)alkoxy groups, halo ($C_1$–$C_6$)alkoxy groups, ($C_1$–$C_6$)alkylthio groups, halo ($C_1$–$C_6$)alkylthio groups, ($C_1$–$C_6$)alkylsulfinyl groups, halo($C_1$–$C_6$)-alkylsulfinyl groups, ($C_1$–$C_6$) alkylsulfonyl groups, halo($C_1$–$C_6$)alkylsulfonyl groups, mono($C_1$–$C_6$)alkylamino groups, di($C_1$–$C_6$) alkylamino groups wherein the two alkyl groups may be the same or different, and ($C_1$–$C_6$)-alkoxycarbonyl groups; a phenylthio group; a substituted phenylthio group having one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)-alkylsulfinyl groups, ($C_1$–$C_6$)alkylsulfonyl groups, halo($C_1$–$C_6$) alkylsulfonyl groups, mono($C_1$–$C_6$)alkylamino groups, di($C_1$–$C_6$)alkylamino groups wherein the two alkyl groups may be the same or different, and ($C_1$–$C_6$)-alkoxycarbonyl groups; a heterocyclic group; or a substituted heterocyclic group having one or more same or different substituents selected from halogen atoms, cyano group, nitro group, ($C_1$–$C_6$)alkyl groups, halo($C_1$–$C_6$)alkyl groups, ($C_1$–$C_6$)alkoxy groups, halo ($C_1$–$C_6$)alkoxy groups, ($C_1$–$C_6$)alkylthio groups, halo ($C_1$–$C_6$)alkylthio groups, ($C_1$–$C_6$)alkylsulfinyl groups, halo($C_1$–$C_6$)-alkylsulfinyl groups, ($C_1$–$C_6$) alkylsulfonyl groups, halo($C_1$–$C_6$)alkylsulfonyl groups, mono($C_1$–$C_6$)alkylamino groups, di($C_1$–$C_6$) alkylamino groups wherein the two alkyl groups may be the same or different, and ($C_1$–$C_6$)-alkoxycarbonyl groups;

$R^1$ may bond with $A^1$ to form a 4- to 7-membered ring which may contain, as a ring-constituting atom(s), one or two same or different atoms selected from oxygen, sulfur and nitrogen atoms;

$R^2$ and $R^3$ may be the same or different and are each a hydrogen atom or a ($C_1$–$C_6$)alkyl group;

$Q^1$ to $Q^4$ are each a carbon atom which may be substituted with X; X may be the same or different when it is more than one, and is a halogen atom, a nitro group, a ($C_1$–$C_6$)alkyl group, a halo($C_1$–$C_6$)alkyl group, a ($C_2$–$C_6$)alkenyl group, a halo($C_2$–$C_6$)alkenyl group, a ($C_2$–$C_6$)alkynyl group, a halo($C_2$–$C_6$)alkynyl group, a halo($C_1$–$C_6$)alkoxy group or a halo($C_1$–$C_6$)alkylthio group; the two Xs bonding to the adjacent two carbon atoms constituting the aromatic ring containing $Q^1$ to $Q^4$ may bond to each other to form a condensed ring; the condensed ring may have one or more same or different substituents selected from halogen atoms, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)alkylsulfinyl groups, ($C_1$–$C_6$)alkylsulfonyl groups and halo($C_1$–$C_6$) alkylsulfonyl groups;

$Q^5$ is a nitrogen atom or a carbon atom;

Y may be the same or different when it is more than one, and is a halogen atom; a ($C_1$–$C_6$)alkyl group; a halo ($C_1$–$C_6$)alkyl group; a ($C_1$–$C_6$)alkoxy group; a halo ($C_1$–$C_6$)alkoxy group; a ($C_1$–$C_6$)alkylthio group; a halo ($C_1$–$C_6$)alkylthio group; a ($C_1$–$C_6$)alkylsulfinyl group; a halo($C_1$–$C_6$)alkylsulfinyl group; a ($C_1$–$C_6$) alkylsulfonyl group; a halo($C_1$–$C_6$)alkylsulfonyl group; a halo($C_1$–$C_6$)alkoxy halo($C_1$–$C_6$)alkoxy group; a phenyl group; a substituted phenyl group having one or more same or different substituents selected from halogen atoms, cyano group, halo($C_1$–$C_6$)alkyl groups, halo($C_1$–$C_6$)alkoxy groups, halo($C_1$–$C_6$)alkylthio groups, halo($C_1$–$C_6$)-alkylsulfinyl groups and halo ($C_1$–$C_6$)alkylsulfonyl groups; a phenyloxy group; a substituted phenyloxy group having one or more same or different substituents selected from halogen atoms, cyano group, halo($C_1$–$C_6$)-alkyl groups, halo($C_1$–$C_6$) alkoxy groups, halo($C_1$–$C_6$)-alkylthio groups, halo ($C_1$–$C_6$)alkylsulfinyl groups and halo($C_1$–$C_6$) alkylsulfonyl groups; a pyridyloxy group; or a substituted pyridyloxy group having one or more same or different substituents selected from halogen atoms, cyano group, halo($C_1$–$C_6$)alkyl groups, halo($C_1$–$C_6$) alkoxy groups, halo($C_1$–$C_6$)alkylthio groups, halo ($C_1$–$C_6$)-alkylsulfinyl groups and halo($C_1$–$C_6$) alkylsulfonyl groups;

the two Ys bonding to the adjacent two carbon atoms constituting the aromatic ring containing $Q^5$ may bond to each other to form a condensed ring; the condensed ring may have one or more same or different substituents selected from halogen atoms; ($C_1$–$C_6$)alkyl groups; halo($C_1$–$C_6$)alkyl groups; ($C_1$–$C_6$)alkoxy groups; halo($C_1$–$C_6$)alkoxy groups; ($C_1$–$C_6$)alkylthio groups; halo($C_1$–$C_6$)alkylthio groups; ($C_1$–$C_6$) alkylsulfinyl groups; halo($C_1$–$C_6$)alkylsulfinyl groups; ($C_1$–$C_6$)alkylsulfonyl groups; halo($C_1$–$C_6$) alkylsulfonyl groups; phenyl group; and substituted phenyl groups having one or more same or different substituents selected from halogen atoms, halo($C_1$–$C_6$) alkyl groups, halo($C_1$–$C_6$)alkoxy groups, halo($C_1$–$C_6$) alkylthio groups, halo($C_1$–$C_6$)alkylsulfinyl groups and halo($C_1$–$C_6$)alkylsulfonyl groups;

m is an integer of 1 to 5;

$Z^1$ and $Z^2$ are each an oxygen atom.

4. An agrohorticultural composition characterised by containing, as an effective ingredient, an aromatic diamide compound of a salt thereof according to claim 1 and an inert carrier.

5. A method for using an agrohorticultural composition according to claim 4, characterized by applying the agrohorticultural composition to a target crop or soil in an effective amount to protect the crop or soil from pests.

* * * * *